United States Patent
Buffa et al.

(10) Patent No.: US 10,221,181 B2
(45) Date of Patent: Mar. 5, 2019

(54) 6-AMINO-7-BICYCLO-7-DEAZA-PURINE DERIVATIVES AS PROTEIN KINASE INHIBITORS

(71) Applicant: NERVIANO MEDICAL SCIENCES S.r.l., Nerviano (MI) (IT)

(72) Inventors: Laura Buffa, Rossiglione (IT); Maria Menichincheri, Milan (IT); Ilaria Motto, Nerviano (IT); Francesca Quartieri, Arona (IT)

(73) Assignee: NERVIANO MEDICAL SCIENCES S.r.l., Nerviano (MI) (IT)

( * ) Notice: Subject to any disclaimer, the term of this patent is extended or adjusted under 35 U.S.C. 154(b) by 0 days.

(21) Appl. No.: 15/526,642

(22) PCT Filed: Nov. 12, 2015

(86) PCT No.: PCT/EP2015/076411
§ 371 (c)(1),
(2) Date: May 12, 2017

(87) PCT Pub. No.: WO2016/075224
PCT Pub. Date: May 19, 2016

(65) Prior Publication Data
US 2017/0327506 A1    Nov. 16, 2017

(30) Foreign Application Priority Data
Nov. 14, 2014 (EP) ..................... 14193197

(51) Int. Cl.
C07D 487/04 (2006.01)
A61K 31/519 (2006.01)
A61P 35/04 (2006.01)
A61P 35/02 (2006.01)

(52) U.S. Cl.
CPC .......... *C07D 487/04* (2013.01); *A61K 31/519* (2013.01)

(58) Field of Classification Search
CPC ........................ C07D 487/04; A61K 31/519
See application file for complete search history.

(56) References Cited

U.S. PATENT DOCUMENTS

| | | |
|---|---|---|
| 2006/0235031 A1 | 10/2006 | Arnold et al. |
| 2007/0112005 A1 | 5/2007 | Chen et al. |
| 2009/0118499 A1 | 5/2009 | Arnold et al. |
| 2009/0163468 A1 | 6/2009 | Chen et al. |
| 2009/0325928 A1 | 12/2009 | Arnold et al. |
| 2010/0099679 A1 | 4/2010 | Chen et al. |
| 2011/0172228 A1 | 7/2011 | Ren et al. |
| 2011/0190496 A1 | 8/2011 | Chen et al. |
| 2011/0218183 A1 | 9/2011 | Chen et al. |
| 2012/0077979 A1 | 3/2012 | Arnold et al. |
| 2012/0196847 A1 | 8/2012 | Arnold et al. |
| 2013/0165651 A1 | 6/2013 | Chen et al. |
| 2013/0190496 A1 | 7/2013 | Mulvihill et al. |

FOREIGN PATENT DOCUMENTS

| | | |
|---|---|---|
| WO | WO 2005/097800 A1 | 10/2005 |
| WO | WO 2007/061737 A2 | 5/2007 |
| WO | WO 2010/006086 A2 | 1/2010 |

OTHER PUBLICATIONS

International Search Report and Written Opinion dated Dec. 14, 2015 in PCT/EP2015/076411 filed Nov. 12, 2015.

*Primary Examiner* — Susanna Moore
(74) *Attorney, Agent, or Firm* — Oblon, McClelland, Maier & Neustadt, L.L.P.

(57) ABSTRACT

6-Amino-7-bicyclo-7-deaza-purine derivatives of formula (I):

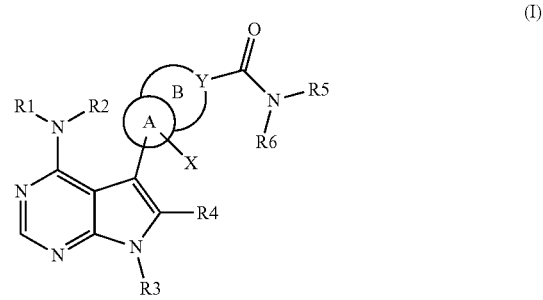

modulate the activity of protein kinases and are therefore useful in treating diseases caused by dysregulated protein kinase activity, in particular RET family kinases. The present invention also provides methods for preparing these compounds, pharmaceutical compositions comprising these compounds, and methods of treating diseases utilizing pharmaceutical compositions containing these compounds.

11 Claims, No Drawings

6-AMINO-7-BICYCLO-7-DEAZA-PURINE DERIVATIVES AS PROTEIN KINASE INHIBITORS

CROSS REFERENCE TO RELATED APPLICATIONS

This application is a 371 of International Patent Application No. PCT/EP2015/076411, filed on Nov. 12, 2015, and claims priority to European Patent Application No. 14193197.2, filed on Nov. 14, 2014, both of which are incorporated herein by reference in their entireties.

The present invention relates to certain 6-amino-7-bicyclo-7-deaza-purine derivatives, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

RET is a single-pass transmembrane receptor belonging to the tyrosine kinase superfamily (reviewed in Arighi et al., Cytokine Growth Factor Rev, 2005, 16, 441-67). The extracellular portion of the RET protein contains four calcium-dependent cadherin-like repeats involved in ligand binding and a juxtamembrane cysteine-rich region necessary for the correct folding of RET extracellular domain, while the cytoplasmic portion of the receptor includes two tyrosine kinase subdomains. RET is the signaling component of a multiprotein complex: binding of RET to the glial-derived neurotrophic factor (GDNF) family ligands (GDNF, artemin, neurturin and persephin) through ligand-specific GDNF-family receptor alpha co-receptors (GFRα1-4) induces the formation of active RET dimers and the autophosphorylation of specific tyrosine residues in the cytoplasmic domain. These phosphorylated tyrosines function as docking sites for effector/adaptor proteins such as PLC-γ, PI3K, Shc, Grb2, Src, Enigma, STAT3, which in turn activate downstream signaling pathways, including Ras/Raf/ERK, PI3K/Akt/mTOR and PLC-γ/PKC. During embryogenesis RET signaling is critical for development of the enteric nervous system and for kidney organogenesis (Schuchardt et al., Nature, 1994, 367, 380-3). In adults RET is expressed in neural crest-derived cell types, such as neuroendocrine cells (thyroid parafollicular cells and adrenal medullary cells), peripheral ganglia, urogenital tract cells and spermatogonia.

Aberrant RET expression and/or activity have been demonstrated in different human cancers.

The oncogenic role of RET was firstly described in papillary thyroid carcinoma (PTC) (Grieco et al., Cell, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (reviewed in Greco et al., Q. J. Nucl. Med. Mol. Imaging, 2009, 53, 440-54), therefore driving its ectopic expression in thyroid cells. To date, twelve different fusion partners have been identified, all providing a protein/protein interaction domain that induces ligand-independent RET dimerization and constitutive kinase activity. The role of RET-PTC rearrangements in the pathogenesis of PTC has been confirmed in transgenic mice (Santoro et al., Oncogene, 1996, 12, 1821-6). Recently, a 10.6 Mb pericentric inversion in chromosome 10, where RET gene maps, has been identified in about 2% of lung adenocarcinoma patients, generating different variants of the chimeric gene KIF5B-RET (Ju et al., Genome Res., 2012, 22, 436-45; Kohno et al., 2012, Nature Med., 18, 375-7; Takeuchi et al., Nature Med., 2012, 18, 378-81; Lipson et al., 2012, Nature Med., 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what observed with RET-PTC fusion proteins, KIF5B-RET is constitutively phosphorylated and induces NIH-3T3 transformation and IL-3 independent growth of BA-F3 cells. However other RET fusion proteins have been identified in lung adenocarcinoma patients, such as the CCDC6-RET protein, which has been found to play a key role in the proliferation of the human lung adenocarcinoma cell line LC-2/ad (Journal of Thoracic Oncology, 2012, 7(12):1872-1876).

Besides rearrangements of the RET sequence, gain of function point mutations of RET proto-oncogene are also driving oncogenic events, as shown in medullary thyroid carcinoma (MTC), which arises from parafollicular calcitonin-producing cells (reviewed in: de Groot et al., Endocrine Rev., 2006, 27, 535-60; Wells and Santoro, Clin. Cancer Res., 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., Science, 2007, 318, 1108-13) and small cell lung carcinoma (Jpn. J. Cancer Res., 1995, 86, 1127-30).

RET signaling components have been found to be expressed in primary breast tumors and to functionally interact with estrogen receptor-α pathway in breast tumor cell lines (Boulay et al., Cancer Res. 2008, 68, 3743-51; Plaza-Menacho et al., Oncogene, 2010, 29, 4648-57), while RET expression and activation by GDNF family ligands could play an important role in perineural invasion by different types of cancer cells (Ito et al., Surgery, 2005, 138, 788-94; Gil et al., J Natl Cancer Inst., 2010, 102, 107-18; Iwahashi et al., Cancer, 2002, 94, 167-74).

Very recently the identification of RET rearrangements has been reported in a subset of (patient-derived xenograft) PDX established from colorectal cancer. Although the frequency of such event in colorectal cancer patients remains to be defined, these data suggest a role of RET as a target in this indication (Gozgit at al, AACR Annual Meeting 2014).

Given the relevant role of RET in human cancer, RET tyrosine kinase inhibitors could be of high therapeutic value. Novel 7-substituted-7-deazaadenosines, useful in the treatment of cancer, have been disclosed in WO2010/121576 in the name of Institute of Organic Chemistry and Biochemistry ASCR, V.V.I.

Pyrrolo[2,3-d]pyrimidine derivatives as CGRP receptor antagonists have been disclosed in WO2009/080682 in the name of Glaxo Group Limited.

Indoline derivatives have been disclosed as inhibitors of PERK in WO2011/119663 in the name of Glaxo Smithkline, LLC.

4-Aminopyrrolopyrimidines have been disclosed ad kinase inhibitors in the name of Basf Aktiengesellschaft (WO00/17202).

Pyrrolopyrimidine derivative have been disclosed in WO2004/056830 in the name of Pfizer Products Inc., useful for the treatment of hyperproliferative diseases such as cancer.

Novel 4-(substituted amino)-7H-pyrrolo[2,3-d] pyrimidines have been disclosed in US2014/0005183 as LRRK2 inhibitors in the name of Pfizer Inc.

EGFR kinase inhibitors in combination with agents that sentisize tumor cells to the effects of an EGFR kinase inhibitors have been disclosed in U.S. Pat. No. 8,586,546 in the name of OSI Pharmaceuticals, LLC.

A series of naphthamides have been published as VEGFR kinase inhibitors in Med. Chem. Lett. 2014, 5, 592-597. Despite these developments, there is still need for effective agents for the treatment of diseases as cancer.

The present inventors have now discovered that compounds of formula (I), described below, are kinase inhibitors and are thus useful in therapy as antitumor agents.

Accordingly, a first object of the present invention is to provide a substituted 6-amino-7-bicyclo-7-deaza-purine compound represented by formula (I)

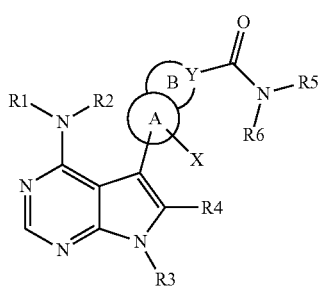

(I)

wherein

R1 and R2 are independently hydrogen or an optionally substituted group selected from straight or branched ($C_1$-$C_6$) alkyl, ($C_3$-$C_6$) cycloalkyl and COR', wherein R' is an optionally substituted group selected from straight or branched ($C_1$-$C_6$) alkyl and ($C_3$-$C_6$) cycloalkyl;

R3 is hydrogen or an optionally substituted group selected from straight or branched ($C_1$-$C_6$) alkyl, ($C_2$-$C_6$) alkenyl, ($C_2$-$C_6$) alkynyl, ($C_3$-$C_6$) cycloalkyl, aryl, heteroaryl and a 3- to 7-membered heterocyclyl ring;

R4 is hydrogen or an optionally substituted group selected from straight or branched ($C_1$-$C_6$) alkyl, ($C_2$-$C_6$) alkenyl, aryl, heteroaryl or heterocyclyl;

A is a 5- or 6-membered heteroaryl ring or a phenyl ring;

B is a 5- or 6-membered ring selected from heteroaryl, ($C_5$-$C_6$) cycloalkyl and heterocyclyl ring or a phenyl ring;

wherein ring A and ring B are fused together to form a bicyclic system comprising a 6-membered aromatic or 5- to 6-membered heteroaromatic ring fused with a 6-membered aromatic or 5- to 6-membered heteroaromatic, ($C_5$-$C_6$) cycloalkyl or heterocyclyl ring;

Y is carbon or nitrogen;

X is hydrogen, halogen, hydroxyl, cyano or an optionally substituted group selected from straight or branched ($C_1$-$C_6$) alkyl and ($C_1$-$C_6$) alkoxyl;

R5 and R6 are independently hydrogen or an optionally substituted group selected from straight or branched ($C_1$-$C_6$) alkyl, ($C_3$-$C_6$) cycloalkyl, heterocyclyl, aryl and heteroaryl;

or pharmaceutically acceptable salts thereof.

The present invention also provides methods of preparing the substituted 6-amino-7-bicyclo-7-deaza-purine compounds, represented by formula (I), prepared through a process consisting of standard synthetic transformations. The present invention also provides a method for treating diseases caused by and/or associated with dysregulated protein kinase activity, particularly RET, RAF family, protein kinase C in different isoforms, Abl, Aurora A, Aurora B, Aurora C, EphA, EphB, FLT3, KIT, LCK, LYN, EGF-R, PDGF-R, FGF-R, PAK-4, P38 alpha, TRKA, TRKB, VEGFR, more particularly RET family kinases, which comprises administering to a mammal in need thereof, more particularly a human, an effective amount of a substituted 6-amino-7-bicyclo-7-deaza-purine compound represented by formula (I) as defined above.

A preferred method of the present invention is to treat a disease caused by and/or associated with dysregulated protein kinase activity selected from the group consisting of cancer, cell proliferative disorders, viral infections, immune-related disorders and neurodegenerative disorders.

Another preferred method of the present invention is to treat specific types of cancer including but not limited to: carcinoma such as bladder, breast, colon, kidney, liver, lung, including small cell lung cancer, esophagus, gallbladder, ovary, pancreas, stomach, cervix, thyroid, prostate and skin, including squamous cell carcinoma; hematopoietic tumors of lymphoid lineage including leukaemia, acute lymphocitic leukaemia, acute lymphoblastic leukaemia, B-cell lymphoma, T-cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid cancers, such as papillary thyroid carcinoma and medullary thyroid carcinoma, and Kaposi's sarcoma.

Another preferred method of the present invention is to treat specific cellular proliferation disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, comprising the prevention of AIDS development in HIV-infected individuals.

Another preferred method of the present invention is to treat immune-related disorders including but not limited to: transplant rejection, skin disorders like psoriasis, allergies, asthma and autoimmune-mediated diseases such as rheumatoid arthritis (RA), systemic lupus erythematosus (SLE), Crohn's disease and amyotrophic lateral sclerosis. Another preferred method of the present invention is to treat neurodegenerative disorders including but not limited to: Alzheimer's disease, degenerative nerve diseases, encephalitis, Stroke, Parkinson's Disease, Multiple Sclerosis, Amyotrophic Lateral Sclerosis (ALS or Lou Gehrig's Disease), Huntington's Disease and Pick's Disease.

In addition, the method of the present invention also provides tumor angiogenesis and metastasis inhibition as well as the treatment of organ transplant rejection and host versus graft disease.

Moreover, the method of the present invention further comprises subjecting the mammal in need thereof to a radiation therapy or chemotherapy regimen in combination with at least one cytostatic or cytotoxic agent.

The present invention also provides a pharmaceutical composition comprising a therapeutically effective amount of a compound of formula (I) or a pharmaceutically acceptable salt thereof, as defined above, and at least one pharmaceutically acceptable excipient, carrier and/or diluent.

The present invention further provides a pharmaceutical composition of a compound of the formula (I) further comprising one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Moreover the invention provides an in vitro method for inhibiting the RET family protein activity which comprises contacting the said protein with an effective amount of a compound of formula (I) as defined above.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides a compound of formula (I) or a pharmaceutically acceptable salt thereof, as defined above, for use in a method of treating cancer.

Finally, the invention provides the use of a compound of formula (I) or a pharmaceutically acceptable salt thereof, as defined above, in the manufacture of a medicament with anticancer activity.

Unless otherwise specified, when referring to the compounds of formula (I) per se as well as to any pharmaceutical composition thereof or to any therapeutic treatment comprising them, the present invention includes all of the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

If a stereogenic center or another form of an asymmetric center is present in a compound of the present invention, all forms of such isomer or isomers, including enantiomers and diastereomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Pharmaceutically acceptable salts of the compounds of formula (I) include the salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines.

With the term "straight or branched ($C_1$-$C_6$) alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "($C_3$-$C_6$) cycloalkyl" we intend, unless otherwise provided, 3- to 6-membered all-carbon monocyclic ring, which may contain one or more double bonds but does not have a completely conjugated 7-electron system. Examples of cycloalkyl groups, without limitation, are cyclopropane, cyclobutane, cyclopentane, cyclopentene, cyclohexane, cyclohexene and cyclohexadiene. The ($C_3$-$C_6$) cycloalkyl ring can be optionally further fused or linked to aromatic and non-aromatic carbocyclic and heterocyclic rings.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, tetrahydropyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like. The heterocyclyl ring can be optionally further fused or linked to aromatic and non-aromatic carbocyclic and heterocyclic rings.

With the term "($C_2$-$C_6$) alkenyl" we intend an aliphatic ($C_2$-$C_6$) hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "($C_2$-$C_6$) alkynyl" we intend an aliphatic ($C_2$-$C_6$) hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated 7-electron bond system. Non limiting examples of such aryl groups are phenyl, α- or β-naphthyl, α- or β-tetrahydronaphthalenyl, biphenyl, and indanyl groups. The aryl ring can be optionally further fused or linked to aromatic and non-aromatic carbocyclic and heterocyclic rings.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, pyrrolyl, phenyl-pyrrolyl, furyl, phenyl-furyl, oxazolyl, isoxazolyl, pyrazolyl, thienyl, thiadiazolyl, isoxazolyl, isothiazolyl, oxadiazolyl, indazolyl, cinnolinyl, benzo[1,3]dioxolyl, benzo[1,4]dioxinyl, benzothiazolyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

According to the present invention and unless otherwise provided, any of the above R1, R2, R3, R4, R5, R6 may be optionally substituted, in any of their free positions, by one or more groups, for instance 1 to 6 groups, independently selected from: halogen, nitro, oxo groups (=O), cyano, ($C_1$-$C_6$) alkyl, polyfluorinated alkyl, polyfluorinated alkoxy, ($C_2$-$C_6$) alkenyl, ($C_2$-$C_6$) alkynyl, hydroxyalkyl, aryl, arylalkyl, alkylaryl, heteroaryl, heteroarylalkyl, alkylheteroaryl, heterocyclyl, heterocyclylalkyl, alkylheterocyclyl, alkylheterocyclylalkyl, ($C_3$-$C_6$) cycloalkyl, hydroxy, polyhydroxyalkyl, alkoxy, aryloxy, heterocyclyloxy, methylenedioxy, alkylcarbonyloxy, arylcarbonyloxy, cycloalkenyloxy, heterocyclylcarbonyloxy, al kylideneaminooxy, carboxy, alkoxycarbonyl, aryloxycarbonyl, cycloalkyloxycarbonyl, amino, heterocyclylalkyloxycarbonylamino, ureido, alkylamino, aminoalkyl, dialkylamino, arylamino, diarylamino, heterocyclylamino, formylamino, alkylcarbonylamino, arylcarbonylamino, heterocyclylcarbonylamino, aminocarbonyl, al kylaminocarbonyl, dialkylaminocarbonyl, arylaminocarbonyl, heterocyclylaminocarbonyl, al koxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term "halogen" we intend a fluorine, chlorine, bromine or iodine atom.

With the term "polyfluorinated alkyl" or "polyfluorinated alkoxy" we intend any of the above straight or branched ($C_1$-$C_6$) alkyl or ($C_1$-$C_6$) alkoxy groups which are substituted by more than one fluorine atom such as, for instance, trifluoromethyl, trifluoroethyl, 1,1,1,3,3,3-hexafluoropropyl, trifluoromethoxy and the like.

With the term "hydroxyalkyl" we intend any of the above ($C_1$-$C_6$) alkyl, bearing a hydroxyl group such as, for instance, hydroxymethyl, 2-hydroxyethyl, 3-hydroxypropyl and the like.

From all of the above, it is clear to the skilled person that any group which name is a composite name such as, for instance, "arylamino" has to be intended as conventionally constructed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, al koxycarbonylamino, heterocyclylcarbonyl, heterocyclylcarbonylamino, cycloalkyloxycarbonyl and the like, include groups wherein the alkyl, alkoxy, aryl, ($C_3$-$C_6$) cycloalkyl and heterocyclyl moieties are as above defined.

A preferred class of compounds of formula (I) are the compounds wherein:
R1 is hydrogen;
R2 is hydrogen, methyl, cyclopropyl or COR' wherein R' is methyl;
R3 is hydrogen or an optionally substituted group selected from straight or branched ($C_1$-$C_6$) alkyl, ($C_3$-$C_6$) cycloalkyl, aryl, heteroaryl and a 3- to 7-membered heterocyclyl ring; and
R4 is hydrogen or an optionally substituted straight or branched ($C_1$-$C_6$) alkyl.

A more preferred class of compounds of formula (I) are the compounds wherein:
R1, R2 and R4 are hydrogen;
R3 is hydrogen or an optionally substituted group selected from straight or branched ($C_1$-$C_6$) alkyl, ($C_3$-$C_6$) cycloalkyl, aryl, heteroaryl and a 3- to 7-membered heterocyclyl ring;
B is a 5- or 6-membered heteroaryl, heterocyclyl ring or phenyl ring;
X is hydrogen, halogen, cyano or an optionally substituted straight or branched ($C_1$-$C_3$) alkyl; and
R5 is hydrogen.

Preferred specific compounds (cmpd) of formula (I) or a pharmaceutically acceptable salt thereof are the compounds listed below:
6-(4-Amino-7-isopropyl-7H-pyrrolo[2,3-d]pyrimidin-5-yl)-naphthalene-1-carboxylic acid cyclopropylamide (cmpd 1),
6-(4-Amino-7-isopropyl-7H-pyrrolo[2,3-d]pyrimidin-5-yl)-naphthalene-2-carboxylic acid cyclopropylamide (cmpd 2)
6-(4-Amino-7-cyclopentyl-7H-pyrrolo[2,3-d]pyrimidin-5-yl)-naphthalene-1-carboxylic acid cyclopropylamide (cmpd 3), 6-(4-Amino-7-isopropyl-7H-pyrrolo[2,3-d]pyrimidin-5-yl)-naphthalene-1-carboxylic acid amide (cmpd 4), 6-(4-Amino-7-isopropyl-7H-pyrrolo[2,3-d]pyrimidin-5-yl)-naphthalene-1-carboxylic acid isopropylamide (cmpd 5), 6-(4-Amino-7-isopropyl-7H-pyrrolo[2,3-d]pyrimidin-5-yl)-naphthalene-1-carboxylic acid methylamide (cmpd 6), 6-(4-Amino-7-isopropyl-7H-pyrrolo[2,3-d]pyrimidin-5-yl)-naphthalene-1-carboxylic acid (2,2,2-trifluoro-ethyl)-amide (cmpd 7), 6-[4-Amino-7-(tetrahydro-pyran-4-yl)-7H-pyrrolo[2,3-d]pyrimidin-5-yl]-naphthalene-1-carboxylic acid cyclopropylamide (cmpd 8), 6-(4-Amino-7-isopropyl-7H-pyrrolo[2,3-d]pyrimidin-5-yl)-naphthalene-1-carboxylic acid cyclopentylamide (cmpd 9), 6-(4-Amino-7-isopropyl-7H-pyrrolo[2,3-d]pyrimidin-5-yl)-naphthalene-1-carboxylic acid [4-(4-methyl-piperazin-1-ylmethyl)-3-trifluoromethyl-phenyl]-amide (cmpd 10), 6-(4-Amino-7-isopropyl-7H-pyrrolo[2,3-d]pyrimidin-5-yl)-naphthalene-1-carboxylic acid cyclobutylamide (cmpd 11), 6-(4-Amino-7-cyclobutyl-7H-pyrrolo[2,3-d]pyrimidin-5-yl)-naphthalene-1-carboxylic acid cyclopropylamide (cmpd 12), 6-(4-Amino-7-cyclopropylmethyl-7H-pyrrolo[2,3-d]pyrimidin-5-yl)-naphthalene-1-carboxylic acid cyclopropylamide (cmpd 13), 6-(4-Amino-7-cyclobutylmethyl-7H-pyrrolo[2,3-d]pyrimidin-5-yl)-naphthalene-1-carboxylic acid cyclopropylamide (cmpd 14), 6-[4-Amino-7-(2,2,2-trifluoro-ethyl)-7H-pyrrolo[2,3-d]pyrimidin-5-yl]-naphthalene-1-carboxylic acid cyclopropylamide (cmpd 15), 5-(4-Amino-7-isopropyl-7H-pyrrolo[2,3-d]pyrimidin-5-yl)-2,3-dihydro-indole-1-carboxylic acid cyclopropylamide (cmpd 16), 6-(4-Amino-7-isopropyl-7H-pyrrolo[2,3-d]pyrimidin-5-yl)-2,3-dihydro-indole-1-carboxylic acid cyclopropylamide (cmpd 17), 5-(4-Amino-7-isopropyl-7H-pyrrolo[2,3-d]pyrimidin-5-yl)-2,3-dihydro-indole-1-carboxylic acid cyclopropylmethylamide (cmpd 18), 5-(4-Amino-7-isopropyl-7H-pyrrolo[2,3-d]pyrimidin-5-yl)-2,3-dihydro-indole-1-carboxylic acid cyclobutylamide (cmpd 19), 5-(4-Amino-7-isopropyl-7H-pyrrolo[2,3-d]pyrimidin-5-yl)-2,3-dihydro-indole-1-carboxylic acid cyclohexylamide (cmpd 20), 5-(4-Amino-7-isopropyl-7H-pyrrolo[2,3-d]pyrimidin-5-yl)-2,3-dihydro-indole-1-carboxylic acid cyclohexylmethylamide (cmpd 21), 5-(4-Amino-7-isopropyl-7H-pyrrolo[2,3-d]pyrimidin-5-yl)-2,3-dihydro-indole-1-carboxylic acid cyclopentylamide (cmpd 22), 5-(4-Amino-7-isopropyl-7H-pyrrolo[2,3-d]pyrimidin-5-yl)-2,3-dihydro-indole-1-carboxylic acid (tetrahydro-pyran-4-yl)-amide (cmpd 23), 5-(4-Amino-7-isopropyl-7H-pyrrolo[2,3-d]pyrimidin-5-yl)-2,3-dihydro-indole-1-carboxylic acid (3-trifluoromethyl-phenyl)-amide (cmpd 24), 5-(4-Amino-7-isopropyl-7H-pyrrolo[2,3-d]pyrimidin-5-yl)-2,3-dihydro-indole-1-carboxylic acid isopropylamide (cmpd 25), 5-(4-Amino-7-isopropyl-7H-pyrrolo[2,3-d]pyrimidin-5-yl)-2,3-dihydro-indole-1-carboxylic acid (1-methyl-piperidin-4-yl)-amide (cmpd 26), 6-(4-Amino-7-isopropyl-7H-pyrrolo[2,3-d]pyrimidin-5-yl)-3,4-dihydro-2H-quinoline-1-carboxylic acid cyclopropylamide (cmpd 27), 6-(4-Amino-7-isopropyl-7H-pyrrolo[2,3-d]pyrimidin-5-yl)-isoquinoline-1-carboxylic acid cyclopropylamide (cmpd 27), 6-(4-Amino-7-cyclohexyl-7H-pyrrolo[2,3-d]pyrimidin-5-yl)-naphthalene-1-carboxylic acid cyclopropylamide (cmpd 28), 6-[4-Amino-7-(4,4-difluoro-cyclohexyl)-7H-pyrrolo[2,3-d]pyrimidin-5-yl]-naphthalene-1-carboxylic acid cyclopropylamide (cmpd 29), 6-[4-Amino-7-(1-methyl-piperidin-4-yl)-7H-pyrrolo[2,3-d]pyrimidin-5-yl]-naphthalene-1-carboxylic acid cyclopropylamide (cmdp 31), 6-[4-Amino-7-(1-cyclopropyl-piperidin-4-yl)-7H-pyrrolo[2,3-d]pyrimidin-5-yl]-naphthalene-1-carboxylic acid cyclopropylamide (cmpd 32), 6-{4-Amino-7-[1-(2-hydroxy-ethyl)-piperidin-4-yl]-7H-pyrrolo[2,3-d]pyrimidin-5-yl}-naphthalene-1-carboxylic acid cyclopropylamide (cmpd 33), 6-[7-(1-Acetyl-piperidin-4-yl)-4-amino-7H-pyrrolo[2,3-d]pyrimidin-5-yl]-naphthalene-1-carboxylic acid cyclopropylamide (cmpd 34), 6-[4-Amino-7-(2,2,6,6-tetramethyl-piperidin-4-yl)-7H-pyrrolo[2,3-d]pyrimidin-5-yl]-naphthalene-1-carboxylic acid cyclopropylamide (cmpd 35), 6-[4-Amino-7-(1,2,2,6,6-pentamethyl-piperidin-4-yl)-7H-pyrrolo[2,3-d]pyrimidin-5-yl]-naphthalene-1-carboxylic acid cyclopropylamide (cmpd 36), 6-[4-Amino-7-(1-methyl-piperidin-4-ylmethyl)-7H-pyrrolo[2,3-d]pyrimidin-5-yl]-naphthalene-1-carboxylic acid cyclopropylamide (cmpd 37), 6-[4-Amino-7-(1-methyl-azetidin-3-ylmethyl)-7H-pyrrolo[2,3-d]pyrimidin-5-yl]-naphthalene-1-carboxylic acid cyclopropylamide (cmpd 38), 6-[4-Amino-7-(1-cyclopropyl-azetidin-3-ylmethyl)-7H-pyrrolo[2,3-d]pyrimidin-5-yl]-naphthalene-1-carboxylic acid cyclopropylamide (cmpd 39), 6-[7-(1-Acetyl-azetidin-3-ylmethyl)-4-amino-7H-pyrrolo[2,3-d]pyrimidin-5-yl]-naphthalene-1-carboxylic acid cyclopropylamide (cmpd 40), 6-{4-Amino-7-[1-(2-hydroxy-ethyl)-azetidin-3-ylmethyl]-7H-pyrrolo[2,3-d]pyrimidin-5-yl}-naphthalene-1-carboxylic acid cyclopropylamide (cmpd 41), 2-(4-Amino-7-isopropyl-7H-pyrrolo[2,3-d]pyrimidin-5-yl)-1H-indole-5-carboxylic acid cyclopropylamide (cmpd 42), 2-(4-Amino-7-isopropyl-7H-pyrrolo[2,3-d]pyrimidin-5-yl)-1H-indole-6-carboxylic acid cyclopropylamide (cmpd 43), 6-(4-Amino-7-isopropyl-7H-pyrrolo[2,3-d]pyrimidin-5-yl)-imidazo[1,2-a]pyridine-2-carboxylic acid cyclopropylamide (cmpd 44), 6-(4-Amino-7-isopropyl-7H-pyrrolo[2,3-d]pyrimidin-5-yl)-1H-indole-3-carboxylic acid cyclopropylamide (cmpd 45), 6-(4-Amino-7-isopropyl-7H-pyrrolo[2,3-d]pyrimidin-5-yl)-benzo[b]thiophene-3-carboxylic acid cyclopropylamide (cmpd 46), 6-(4-Amino-7-isopropyl-7H-pyrrolo[2,3-d]pyrimidin-5-yl)-1H-indazole-3-carboxylic acid cyclopropylamide (cmpd 47).

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

The compounds of this invention can be prepared from readily available starting materials using the following general methods and procedures. Unless otherwise indicated, the starting materials are known compounds or may be prepared from known compounds according to well known procedures. It will be appreciated that, where typical or preferred process conditions (i.e. reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures. Additionally, as it will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

The compounds of every general formula can be further transformed in other compounds of the same general formula according to methods well known in the literature, as reported in the experimental section.

In the following Schemes the general preparation of a compound of formula (I), wherein A, B, R1, R2, R3, R4, R5, R6, X and Y are as defined above, is shown.

The general preparation of compounds of formula (I) and the salts thereof, object of the present invention, wherein A, B, R1, R2, R3, R4, R5, R6, X and Y are as defined above, is shown in the following Scheme 1.

Scheme 1

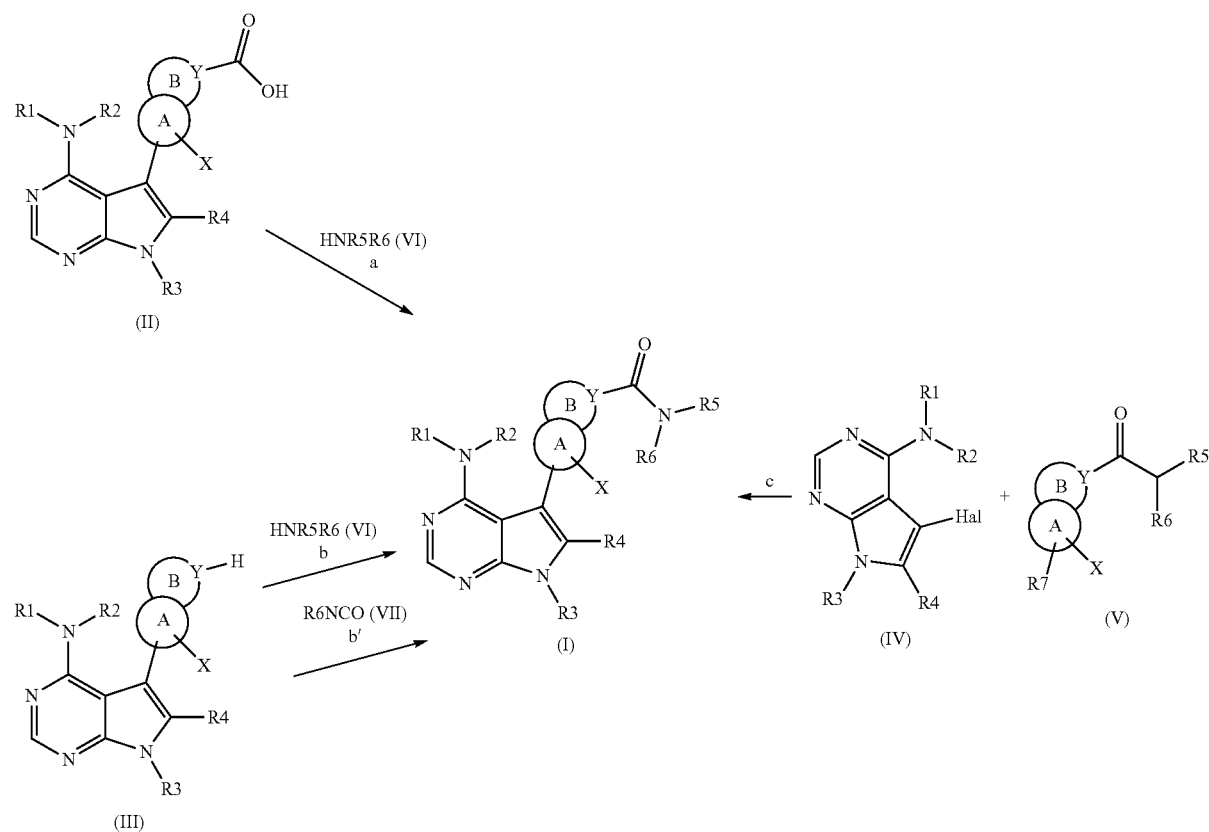

According to the above Scheme 1, a process of the present invention comprises the following steps:

Step a): reaction of an intermediate of formula (II), wherein Y is carbon and A, B, R1, R2, R3, R4 and X are as defined above, with an intermediate of formula (VI) wherein R5 and R6 are as defined above, to obtain a compound of formula (I), wherein Y is carbon, A, B, R1, R2, R3, R4, R5, R6 and X are as defined above;

alternatively

Step b): reaction of an intermediate of formula (III), wherein Y is nitrogen, B is a 5- or 6-membered heterocyclyl ring and A, R1, R2, R3, R4 and X are as defined above, with an intermediate of formula (VI), wherein R5 and R6 are as defined above, to obtain a compound of formula (I) wherein Y is nitrogen, B is a 5- or 6-membered heterocyclyl ring, A, R1, R2, R3, R4, R5, R6 and X are as defined above;
or Step b'): reaction of an intermediate of formula (III), wherein Y is nitrogen, B is a 5- or 6-membered heterocyclyl ring and A, R1, R2, R3, R4 and X are as defined above, with an intermediate of formula (VII), wherein R6 is as defined above, to obtain a compound of formula (I), wherein Y is nitrogen, B is a 5- or 6-membered heterocyclyl ring, R5 is hydrogen and A, R1, R2, R3, R4, R6 and X are as defined above;

alternatively

Step c): cross-coupling reaction of an intermediate of formula (IV), wherein R1, R2, R3, R4 are as defined above and Hal is iodine or bromine, preferably iodine, with an intermediate of formula (V), wherein R7 is a boronic acid or boronic ester and A, B, R5, R6, X and Y are as defined above, to obtain a compound of formula (I), wherein A, B, R1, R2, R3, R4, R5, R6, X and Y are as defined above;

optionally converting a compound of formula (I) into another compound of formula (I), and, if desired, converting a compound of formula (I) into a pharmaceutically acceptable salt thereof or converting a salt into the free compound (I).

According to step a) of the present invention, an intermediate of formula (II) is reacted with an intermediate of formula (VI) to obtain a compound of formula (I) in the presence of a coupling agent such as, for instance, 2-(1H-benzotriazol-1-yl)-1,1,3,3-tetramethyluronium tetrafluoroborate (TBTU), 1,3-dicyclohexylcarbodiimide (DCC), 1,3-diisopropylcarbodiimide (DIC), 1-(3-dimethylaminopropyl)-3-ethylcarbodiimide (EDCl), N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide, N,N-dimethylacetamide at a temperature ranging from about −10° C. to reflux and for a suitable time, for instance from about 30 minutes to about 96 hours. The said reaction is optionally carried out in the presence of a suitable catalyst, for instance 4-dimethylaminopyridine (DMAP), or in the presence of a further coupling reagent such as N-hydroxybenzotriazole (HOBT), or in the presence of a suitable base such as triethylamine (TEA) or N,N-diisopropyl-N-ethylamine (DIPEA).

According to step b) of the present invention, a compound of formula (I) can be prepared by reacting an intermediate of formula (VI) with triphosgene (bis(trichloromethyl) carbonate, O=C(OCCl$_3$)$_2$) or phosgene followed by the addition of the intermediate of formula (III). This reaction can be carried out in the presence of a base like diisopropylethylamine (DIPEA), triethylamine (TEA), Na$_2$CO$_3$, in solvents like dichloromethane or chloroform, at a temperature ranging from about −10° C. to reflux and for a time varying from about 30 minutes to about 96 hours.

Alternatively, according to step b') of the present invention, a compound of formula (I) can be prepared by reacting an intermediate of formula (III) with the appropriate isocyanate of formula (VII). Such a reaction is carried out in a suitable solvent such as dichloromethane or tetrahydrofuran, normally at a temperature ranging from about −10° C. to reflux and for a time varying from about 30 minutes to about 96 hours.

According to step c) of the present invention, reaction of intermediates of formula (IV) with intermediates of formula (V) can be performed under standard conditions as for Suzuki coupling using a Pd-based catalyst (PdCl$_2$dppf, PdCl$_2$(PPh$_3$)$_2$, Pd(PPh$_3$)$_4$, Pd(OAc)$_2$) with a suitable base such as sodium carbonate (Na$_2$CO$_3$), caesium carbonate (Cs$_2$CO$_3$), potassium phosphate (K$_3$PO$_4$), in the presence of ligands such as but not limited to triphenylphosphine, 3,3', 3''-phosphanetriyltris(benzenesulfonic acid) trisodium salt (TPPTS), diphenylphosphinoferrocene (dppf), in suitable organic solvents such as 1,4-dioxane, 1,2-dimethoxyethane, mixtures water/1,4-dioxane, mixtures water/1,2-dimethoxyethane, mixtures water/acetonitrile, N,N-dimethylformamide, toluene and the like at temperatures ranging from room temperature to reflux, for a time period ranging from 1 hour to 48 hours. (Ref. Med. Chem. Lett. 2014, 5, 592-597; J. Med. Chem. 2011, 54, 5498-5507; ChemMedChem 2013, 8, 832-846).

Preparation of intermediates of formula (II), wherein Y is carbon and A, B, R1, R2, R3, R4 and X are as defined above, can be carried out as described in the following Scheme 2.

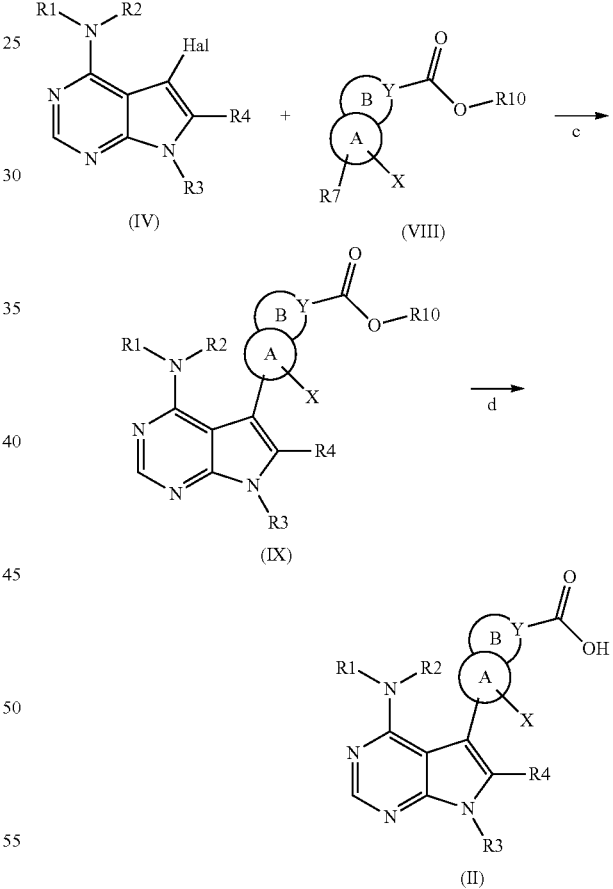

Scheme 2

According to the above Scheme 2, a process of the present invention comprises the following steps:

Step c): cross-coupling reaction of an intermediate of formula (IV), wherein R1, R2, R3, R4 are as defined above and Hal is iodine or bromine, preferably iodine, with an intermediate of formula (VIII), wherein Y is carbon, R7 is a boronic acid or boronic ester, R10 is straight or branched (C$_1$-C$_4$) alkyl, and A, B and X are as defined above, to obtain an intermediate of formula (IX), wherein Y is carbon, R10 is straight or branched ($C_1$-$C_4$) alkyl, and A, B, R1, R2, R3, R4 and X are as defined above.

Step d): hydrolysis of the resultant intermediate of formula (IX), to obtain an intermediate of formula (II), wherein Y is carbon, and A, B, R1, R2, R3, R4 and X are as defined above.

According to step c) of Scheme 2, the reaction is carried out as described for step c) of Scheme 1.

According to step d) of the present invention, hydrolysis of an intermediate of formula (IX) can be performed in the presence of a base such as LiOH, NaOH, KOH or an acid such as HCl, TFA in a suitable solvent such as methanol, ethanol, tetrahydrofuran, dichloromethane, tetrahydrofuran/water mixtures and the like at temperatures ranging from room temperature to reflux, for a time period ranging from 1 hour to 48 hours.

Alternatively an intermediate of formula (II), wherein Y is carbon, R4 is ($C_2$-$C_6$) alkenyl, aryl, heteroaryl or heterocyclyl, and A, B, R1, R2, R3, and X are as defined above, i.e. an intermediate of formula (IIa), can be carried out as described in the following Scheme 2a.

Scheme 2a

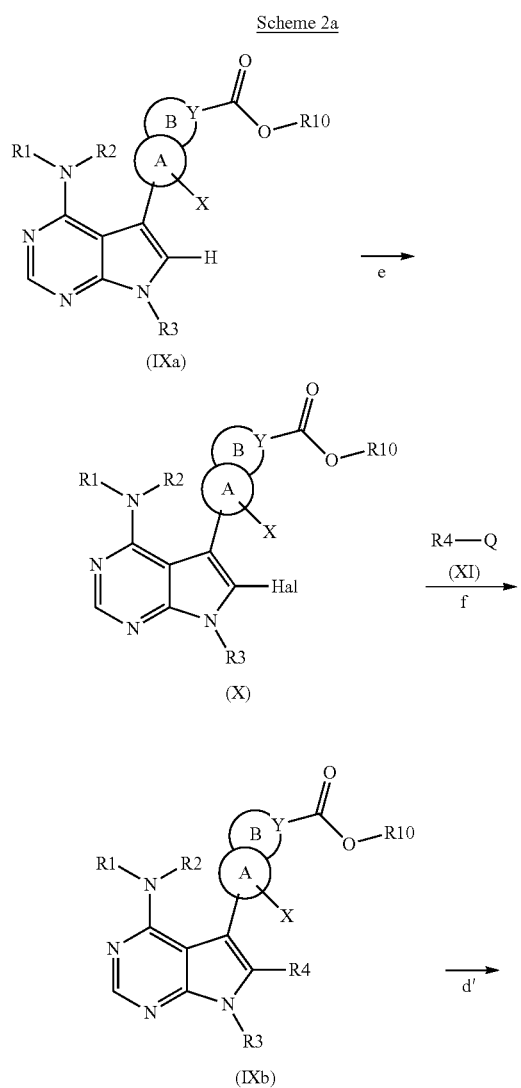

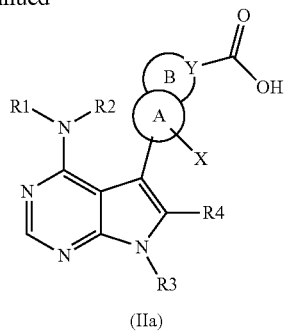

(IIa)

According to the above Scheme 2a, a process of the present invention comprises the following steps:

Step e): halogenation of an intermediate of formula (IX) wherein R4 is hydrogen, Y is carbon, R10 is straight or branched ($C_1$-$C_4$) alkyl and A, B, R1, R2, R3 and X are as defined above, i.e. an intermediate of formula (IXa), to obtain an intermediate of formula (X) wherein Hal is iodine or bromine, Y is carbon, R10 is straight or branched ($C_1$-$C_4$) alkyl, and A, B, R1, R2, R3 and X are as defined above;

Step f): reaction of the resultant intermediate of formula (X) with an intermediate of formula R4-Q (XI), wherein Q is a boronic acid or boronic ester or a stannane and R4 is ($C_2$-$C_6$) alkenyl, aryl, heteroaryl or heterocyclyl, or Q is hydrogen when R4 is ($C_2$-$C_6$) alkenyl, to obtain an intermediate of formula (IXb), wherein Y is carbon, R4 is ($C_2$-$C_6$) alkenyl, aryl, heteroaryl or heterocyclyl, R10 is straight or branched ($C_1$-$C_4$) alkyl, and A, B, R1, R2, R3 and X are as defined above;

Step d'): hydrolysis of the resultant intermediate of formula (IXb) to obtain an intermediate of formula (IIa), wherein Y is carbon, R4 is ($C_2$-$C_6$) alkenyl, aryl, heteroaryl or heterocyclyl and A, B, R1, R2, R3, and X are as defined above.

According to step e) of the present invention halogenation of an intermediate of formula (IXa), can be carried out in the presence of N-iodosuccinimide or N-bromosuccinimide to obtain an intermediate of formula (X), wherein Hal is iodine or bromine, in a suitable solvent such as dichloromethane, N,N-dimethylformamide or N,N-dimethylacetamide at room temperature for a time period ranging from 1 hour to 48 hours (ref. Bioorg. Med. Chem. Lett. 2000, 2171-2174; Chem. Commun. 1997, 695-696).

According to step f) of the present invention, when Q is a boronic acid or boronic ester, the reaction can be carried out by employing the proper aryl, heteroaryl or heterocyclyl boronic derivative in the presence of a base such as sodium carbonate ($Na_2CO_3$), potassium carbonate ($K_2CO_3$), potassium acetate (KOAc), using a Pd-based catalyst ($PdCl_2dppf$, $PdCl_2(PPh_3)_2$, $Pd(PPh_3)_4$, $Pd(OAc)_2$), with or without the presence of lithium chloride, in a suitable solvent such 1,4-dioxane, 1,2-dimethoxyethane, mixtures water/1,4-dioxane, mixtures water/1,2-dimethoxyethane, N,N-dimethylformamide, toluene and the like, at a temperature ranging from 70° C. to 160° C., in classical thermal conditions or in a microwave apparatus.

Alternatively, when Q is a stannane, the reaction can be carried out by employing the proper ($C_2$-$C_6$) alkenyl stannane derivative in the presence of tetrabutyl ammonium chloride or bromide or lithium chloride, and in the presence of a Pd-based catalyst ($PdCl_2dppf$, $PdCl_2(PPh_3)_2$, $Pd(PPh_3)_4$, $Pd(OAc)_2$), in a suitable solvent such as N,N-dimethylformamide, ethanol, toluene, at a temperature ranging from room temperature to reflux for a time period ranging from 1 hour to 48 hours (ref. Bioorg. Med. Chem. Lett. 2000, 2171-2174; Chem. Commun. 1997, 695-696). Alternatively, when Q is hydrogen and R4 is ($C_2$-$C_6$) alkenyl, the reaction can be carried out in the presence of potassium acetate, sodium carbonate, triethylamine, tetrabutyl ammonium bromide or chloride, with or without the presence of a phosphine such as triphenylphosphine or tris(o-tolyl)phosphine, and in the presence of a catalyst such as Pd(OAc)$_2$, Pd$_2$(dba)$_3$, in a suitable solvent such as N,N-dimethylformamide or acetonitrile at a temperature ranging from room temperature to reflux for a time period ranging from 1 hour to 48 hours.

According to step d') of Scheme 2a, the reaction is carried out as described for step d) of Scheme 2.

Preparation of intermediates of formula (III), wherein Y is nitrogen, B is a 5- or 6-membered heterocyclyl ring and A, R1, R2, R3, R4 and X are as defined above, can be carried out as described in the following Scheme 3.

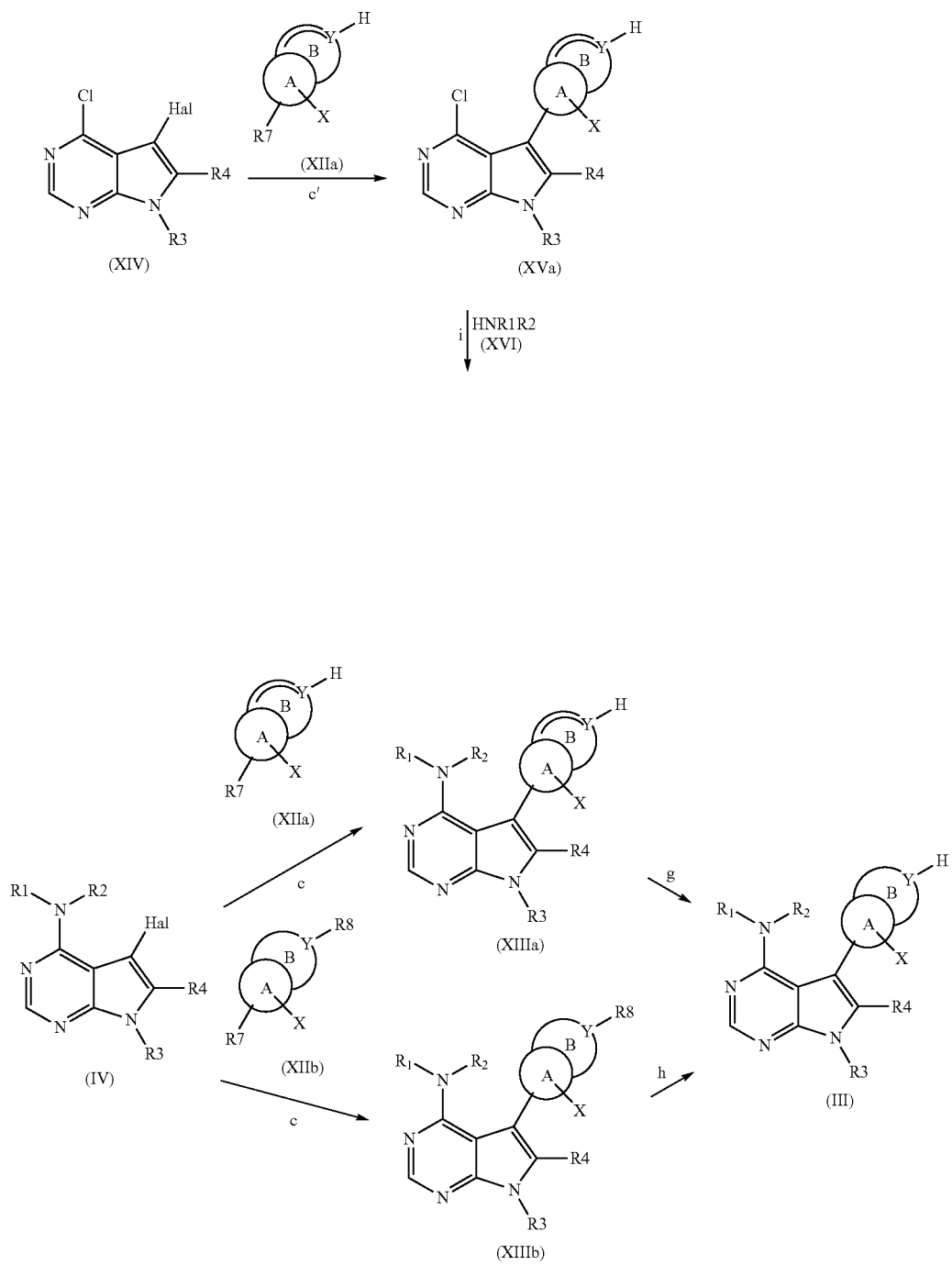

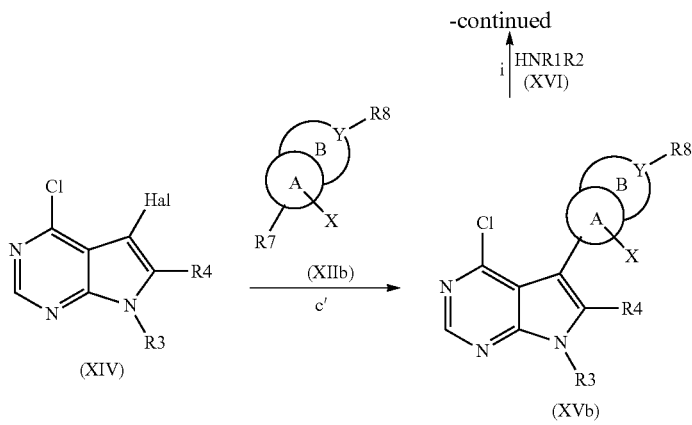

According to the above Scheme 3, a process of the present invention comprises the following steps:

Step c): cross-coupling reaction of an intermediate of formula (IV), wherein Hal is iodine or bromine, preferably iodine, and R1, R2, R3 and R4 are as defined above, alternatively:

with an intermediate of formula (XIIa), wherein Y is nitrogen, B is a 5- or 6-membered heteroaryl ring, R7 is a boronic acid or boronic ester, and A and X are as defined above, to obtain a compound of formula (XIIIa), wherein Y is nitrogen, B is a 5- or 6-membered heteroaryl ring, and A, R1, R2, R3, R4 and X are as defined above;

or with an intermediate of formula (XIIb), wherein Y is nitrogen, B is a 5- or 6-membered heterocyclyl ring, R7 is a boronic acid or boronic ester, R8 is a suitable protecting group COR10 or COOR10, wherein R10 is a straight or branched ($C_1$-$C_4$) alkyl, and A and X are as defined above, to obtain a compound of formula (XIIIb), wherein Y is nitrogen, B is a 5- or 6-membered heterocyclyl ring, R8 is a suitable protecting group COR10 or COOR10, wherein R10 is a straight or branched ($C_1$-$C_4$) alkyl, and A, R1, R2, R3, R4 and X are as defined above;

then

Step g): reduction of the resulting intermediate of formula (XIIIa) to obtain an intermediate of formula (III), wherein Y is nitrogen, B is a 5- or 6-membered heterocyclyl ring, and A, R1, R2, R3, R4 and X are as defined above; or Step h): deprotection of the resultant intermediate of formula (XIIIb) to obtain an intermediate of formula (III) as defined above.

Alternatively the intermediates of formula (XIIIa) and (XIIIb) can be prepared according to the following steps:
Steps c'): cross-coupling reaction of an intermediate of formula (XIV), wherein R4 is hydrogen or an optionally substituted straight or branched ($C_1$-$C_6$) alkyl, Hal is iodine or bromine, preferably iodine, and R3 is as defined above, with an intermediate of formula (XIIa) as defined above or (XIIb) as defined above to respectively obtain an intermediate of formula (XVa), wherein Y is nitrogen, B is a 5- or 6-membered heteroaryl ring, R4 is hydrogen or an optionally substituted straight or branched ($C_1$-$C_6$) alkyl, and R3, A and X are as defined above, or an intermediate of formula (XVb), wherein Y is nitrogen, B is a 5- or 6-membered heterocyclyl ring, R4 is hydrogen or an optionally substituted straight or branched ($C_1$-$C_6$) alkyl, R8 is a suitable protecting group COR10 or COOR10, wherein R10 is a straight or branched ($C_1$-$C_4$) alkyl, and R3, A and X are as defined above;

then

Steps i): reaction of the resultant intermediates of formula (XVa) or (XVb) as defined above with an intermediate of formula (XVI), wherein R1 and R2 are as defined above, to respectively obtain an intermediate of formula (XIIIa) or (XIIIb) as defined above. According to steps c) and c') of Scheme 3, reaction of the intermediates of formula (IV) or (XIV) with the intermediates of formula (XIIa) and (XIIb) to respectively obtain the intermediates of formula (XIIIa) and (XIIIb) or (XVa) and (XVb) can be performed as described for step c) of Scheme 1.

According to step g) of the present invention, reduction of an intermediate of general formula (XIIIa) to obtain an intermediate of formula (III) can be performed in the presence of a reducing agent such as $NaBH_4$, $NBu_4BH_4$, $NaCNBH_3$, $Et_3SiH$, $BH_3NMe_3$, with the addition of an acid like acetic acid or TFA (trifluoroacetic acid), in solvents such as methanol, ethanol, dichloromethane and the like at temperatures ranging from room temperature to reflux, for a time period ranging from 1 hour to 48 hours.

According to step h) of the present invention, reaction of an intermediate of formula (XIIIb) to obtain an intermediate of formula (III) can be performed in the presence of a base such as LiOH, NaOH, KOH or an acid such as HCl, TFA in a suitable solvent such as methanol, ethanol, tetrahydrofuran, dioxane, dichloromethane, water and the like at temperatures ranging from room temperature to reflux, for a time period ranging from 1 hour to 48 hours.

According to step i) of the present invention, the reaction of an intermediate of formula (XVa) or (XVb) with an intermediate of formula (XVI) to obtain an intermediate of formula (XIIIa) or (XIIIb) can be carried out without solvent or in a solvent such as 1,4-dioxane, N,N-dimethylformamide, N,N-dimethylacetamide or dimethylsulfoxide at a temperature ranging from 60° C. to 150° C. for a time ranging from 1 to 24 hours in classical thermal conditions or in a microwave apparatus.

Alternatively, step i) can be carried out in a suitable solvent such as tetrahydrofuran or 1,4-dioxane in the presence of a base such as sodium carbonate ($Na_2CO_3$), caesium carbonate ($Cs_2CO_3$), potassium phosphate ($K_3CO_4$), with a Pd-based catalyst ($Pd(OAc)_2$, $Pd_2dba_3$) and in the presence of a ligand such as Xantphos (4,5-bis(diphenylphosphino)-9,9-dimethylxanthene), BINAP (2,2'-bis(diphenylphosphino)-1,1'-binaphthyl), P(o-Tol)$_3$ in classical thermal conditions at reflux or in a microwave apparatus for a time ranging from 1 to 24 hours at a temperature ranging from 50° C. to 100° C.

Preparation of intermediates of formula (III) wherein Y is nitrogen, B is a 5- or 6-membered heterocyclyl ring, R4 is (C2-C6) alkenyl, aryl, heteroaryl or heterocyclyl and A, R1, R2, R3 and X are as defined above. i. e. an intermediate of formula (IIIb), can be carried out as described in the following Scheme 3a.

Scheme 3a

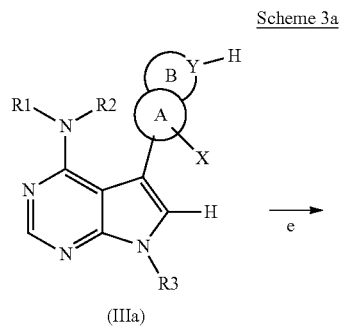

(IIIa)

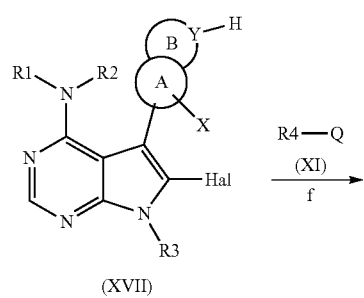

(XVII)

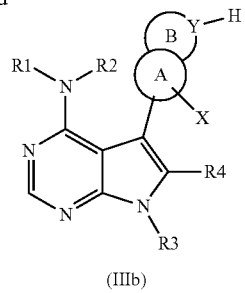

(IIIb)

Step e) halogenation of an intermediate of formula (III) wherein R4 is hydrogen, Y is nitrogen, B is a 5- or 6-membered heterocyclyl ring, A, R1, R2, R3 and X are as defined above, i.e. an intermediate of formula (IIIa), to obtain an intermediate of formula (XVII), wherein Hal is iodine or bromine, Y is nitrogen, B is a 5- or 6-membered heterocyclyl ring and A, R1, R2, R3 and X are as defined above;

Step f) reaction of the resultant intermediate of formula (XVII) with an intermediate of formula R4-Q (XI), wherein Q is a boronic acid or boronic ester or a stannane and R4 is ($C_2$-$C_6$) alkenyl, aryl, heteroaryl or heterocyclyl, or Q is hydrogen when R4 is ($C_2$-$C_6$) alkenyl, to obtain an intermediate of formula (III), wherein R4 is ($C_2$-$C_6$) alkenyl, aryl, heteroaryl or heterocyclyl, Y is nitrogen, B is a 5- or 6-membered heterocyclyl ring, and A, R1, R2, R3 and X are as defined above, i. e. an intermediate of formula (IIIb).

According to step e) of Scheme 3a, halogenation of an intermediate of formula (IIIa), wherein R4 is hydrogen, can be carried out as described for step e) of Scheme 2a (ref. Bioorg. Med. Chem. Lett. 2000, 2171-2174; Chem. Commun. 1997, 695-696).

According to step f) of Scheme 3a, the reaction is carried out as described for step f) of Scheme 2a.

Preparation of intermediates of formula (IV) wherein R4 is hydrogen or an optionally substituted straight or branched ($C_1$-$C_6$) alkyl, Hal is iodine or bromine, R1, R2 and R3 are as defined above, i.e. intermediates of formula (IVa), can be carried out as described in the following Scheme 4a.

Scheme 4a

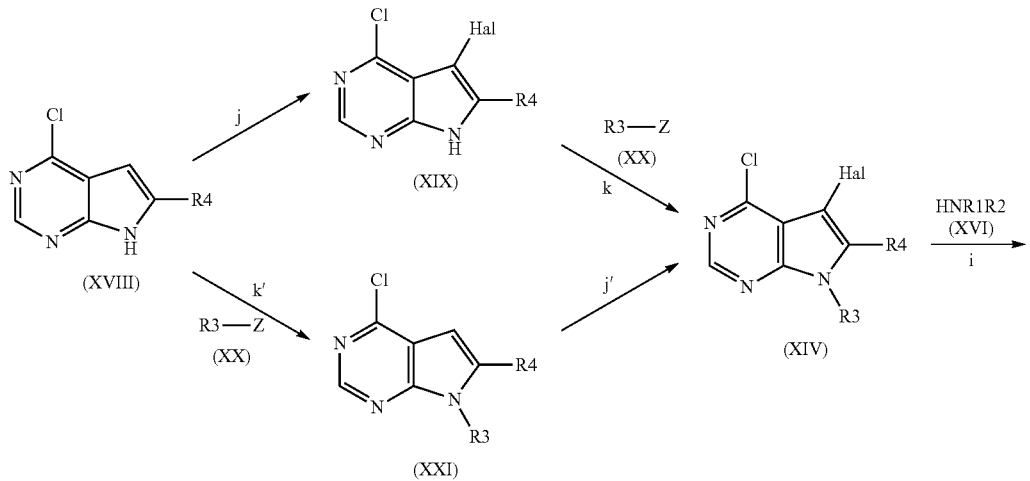

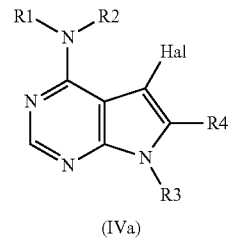

(IVa)

According to Scheme 4a, intermediates of formula (IVa) can be prepared by the following reactions:

Step j): halogenation of an intermediate of general formula (XVIII), wherein R4 is hydrogen or an optionally substituted straight or branched ($C_1$-$C_6$) alkyl, to obtain an intermediate of formula (XIX), wherein Hal is iodine or bromine and R4 is hydrogen or an optionally substituted straight or branched ($C_1$-$C_6$) alkyl;

Step k): reaction of the resultant intermediates of formula (XIX) with intermediates of formula (XX), wherein Z is iodine, bromine, mesylate, tosylate, triflate, hydroxyl, boronic acid or boronic ester and R3 is as defined above, to obtain intermediates of formula (XIV), wherein Hal is iodine or bromine, R4 is hydrogen or an optionally substituted straight or branched ($C_1$-$C_6$) alkyl and R3 is as defined above;

alternatively

Step k') reaction of intermediates of formula (XVIII), wherein R4 is hydrogen or an optionally substituted straight or branched ($C_1$-$C_6$) alkyl, with intermediates of formula (XX), wherein Z is iodine, bromine, mesylate, tosylate, triflate, hydroxyl, boronic acid or boronic ester and R3 is as defined above, to obtain intermediates of formula (XXI), wherein R4 is hydrogen or an optionally substituted straight or branched ($C_1$-$C_6$) alkyl and R3 is as defined above;

Step j') halogenation of the resultant intermediates of formula (XXI) to obtain intermediates of formula (XIV), wherein Hal is iodine or bromine, R4 is hydrogen or an optionally substituted straight or branched ($C_1$-$C_6$) alkyl and R3 is as defined above;

then

Step i) reaction of the resultant intermediates of formula (XIV), wherein Hal is iodine or bromine, R4 is hydrogen or an optionally substituted straight or branched ($C_1$-$C_6$) alkyl and R3 is as defined above, with intermediates of formula (XVI), wherein R1 and R2 are as defined above, to obtain intermediates of formula (IVa), wherein Hal is iodine or bromine, R4 is hydrogen or an optionally substituted straight or branched ($C_1$-$C_6$) alkyl, and R1, R2, and R3 are as defined above.

According to steps j) and j') of the present invention, intermediates (XVIII) and (XXI) are submitted to halogenation with N-iodosuccinimide to obtain intermediates of formula (XIX) and (XIV), wherein Hal is iodine, or with N-bromosuccinimide or pyridine hydrobromide perbromide to obtain intermediates of formula (XIX) and (XIV), wherein Hal is bromine. The reaction can be carried out in a suitable solvent such as acetonitrile, N,N-dimethylformamide, chloroform or tetrahydrofuran at a temperature ranging from room temperature to 70° C., operating in classical thermal conditions or in a microwave apparatus. Alternatively, the reaction to obtain the compounds of formula (XIX) and (XIV), wherein Hal is iodine, can be carried out with molecular iodine, with or without the presence of potassium hydrate in a suitable solvent such as N,N-dimethylformamide or mixtures water-methanol, at room temperature, or with molecular iodine with the presence of silver acetate or silver trifluoroacetate in a suitable solvent such as N,N'-dimethylformamide or dichloromethane at a temperature ranging from room temperature to 80° C. The reaction can be also carried out with iodine monochloride, with or without the presence of sodium or potassium carbonate, in a suitable solvent such as 1,4-dioxane or dichloromethane, at a temperature ranging from room temperature to reflux.

According to steps k) and k') of the present invention, the reaction can be performed in the presence of a suitable base such as caesium carbonate (052003), sodium carbonate ($Na_2CO_3$) or potassium carbonate ($K_2CO_3$) when Z is iodine, bromine, chlorine, mesylate, tosylate or triflate in a suitable solvent such as 1,4-dioxane, tetrahydrofuran, N,N-dimethylformamide at a temperature ranging from room temperature to 100° C., in classical thermal conditions or in a microwave apparatus. Alternatively, the reaction can be carried out under Mitsunobu condition when Z is hydroxyl in the presence of diethyl or diisopropyl azodicarboxylate and triphenylphosphine, in a suitable solvent such as tetrahydrofuran or dichloromethane at a temperature ranging from 0° C. to 70° C.

In a further alternative way, when Z is a boronic acid or boronic ester, the reaction can be carried out in the presence of copper acetate, 2,2'-bipyridyl and sodium carbonate in N,N-dimethylacetamide at a temperature ranging from 70° C. to 120° C. or with cuprous oxide in methanol at reflux.

Alkyl iodide, bromide, chloride, mesylate, tosylate, triflate, hydroxyl and aryl, heteroaryl or heterocyclyl boronic derivatives employed as reactants in the above mentioned steps k) and k') are commercially available compounds or can be prepared according to methods described in the literature.

According to step i) of Scheme 4a, the reaction can be carried out as described for step i) of Scheme 3.

Intermediates of formula (XVIII) wherein R4 is an optionally substituted straight or branched ($C_1$-$C_6$) alkyl can be either commercially available or can be prepared according to the procedure described in patent WO99065609.

Preparation of intermediates of formula (IV), wherein R4 is an optionally substituted straight or branched ($C_2$-$C_6$) alkenyl, aryl, heteroaryl or heterocyclyl, and R1, R2 and R3 are as defined above, i.e. intermediates of formula (IVb), can be carried out as described in the following Scheme 4b.

Scheme 4b

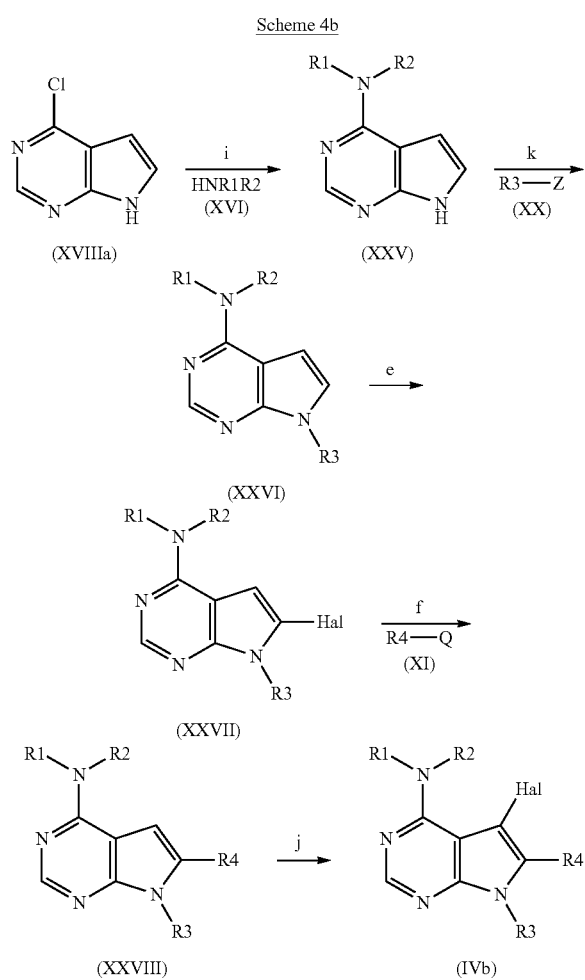

According to Scheme 4b, intermediates of formula (IVb) can be prepared by the following reactions:

Step i): reaction of an intermediate of formula (XVIIIa) with a intermediate of formula (XVI), wherein R1 and R2 are as defined above, to obtain an intermediate of formula (XXV), wherein R1 and R2 are as defined above;

Step k): reaction of the resultant intermediate of formula (XXV) with an intermediate of formula (XX), wherein Z is iodine, bromine, mesylate, tosylate, triflate, hydroxyl, boronic acid or boronic ester and R3 is as defined above, to obtain intermediates of formula (XXVI), wherein R1, R2 and R3 are as defined above;

Step e): halogenation of the resultant intermediates of formula (XXVI) to obtain intermediates of formula (XXVII), wherein Hal is iodine or bromine, R1, R2 and R3 are as defined above;

Step g): reaction of the resultant intermediates of formula (XXVII) with intermediates of formula (XI), wherein Q is a boronic acid or boronic ester or a stannane and R4 is ($C_2$-$C_6$) alkenyl, aryl, heteroaryl or heterocyclyl, or Q is hydrogen when R4 is ($C_2$-$C_6$) alkenyl, to obtain intermediates of formula (XXVIII), wherein R4 is ($C_2$-$C_6$) alkenyl, aryl, heteroaryl or heterocyclyl, and R1, R2 and R3 are as defined above;

Step j): halogenation of the resultant intermediates of formula (XXVIII) to obtain intermediates of formula (IVb), wherein Hal is iodine or bromine, R4 is ($C_2$-$C_6$) alkenyl, aryl, heteroaryl or heterocyclyl, and R1, R2 and R3 are as defined above, i.e. intermediates of formula (IVb).

According to step i) of Scheme 4b, the reaction can be carried out as described for step i) of Scheme 3.

According to step k) of Scheme 4b, the reaction can be carried out as described for steps k) and k') of Scheme 4a.

According to step e) of Scheme 4b, halogenation can be carried out as described for step e) of Scheme 2a (ref. Bioorg. Med. Chem. Lett. 2000, 2171-2174; Chem. Commun. 1997, 695-696).

According to step f) of Scheme 4b, the reaction is carried out as described for step f) of Scheme 2.

According to step j) of Scheme 4b, halogenation is carried out as described for step j) of Scheme 4a.

Preparation of intermediates of formula (V), wherein R7 is a boronic acid or boronic ester and A, B, R5, R6, X and Y are as defined above, can be carried out as described in the following Scheme 5.

Scheme 5

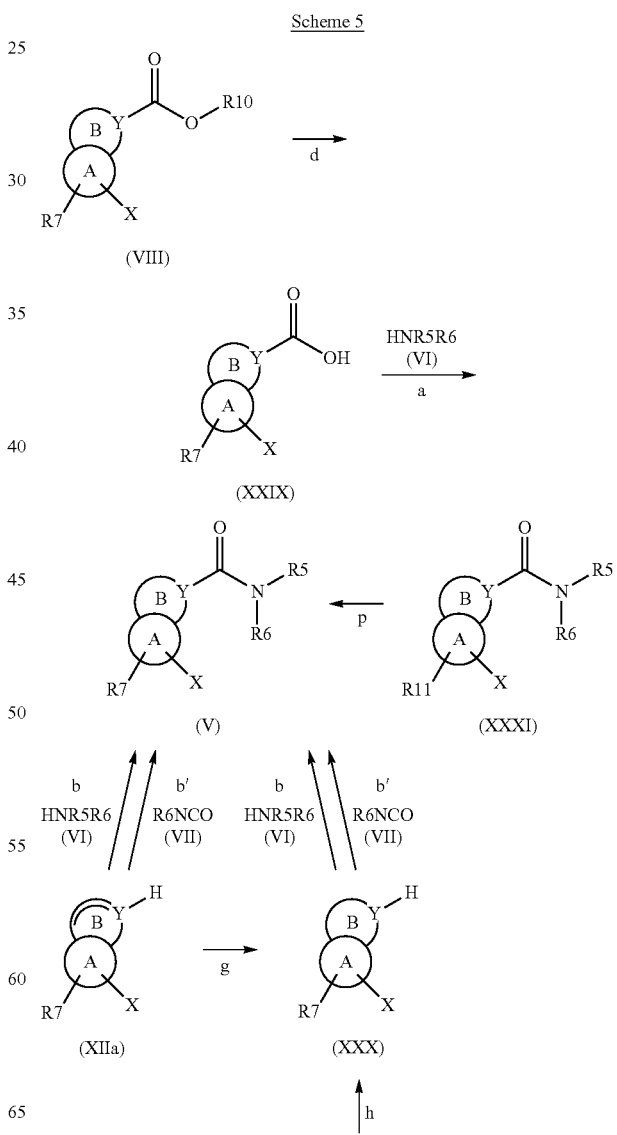

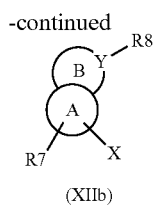

(XIIb)

According to Scheme 5, intermediates of formula (V) can be prepared by the following reactions:

Step d) reaction of an intermediate of formula (VIII), wherein Y is carbon, R7 is a boronic acid or boronic ester, R10 is straight or branched ($C_1$-$C_4$) alkyl, A, B and X are as defined above, to obtain an intermediate of formula (XXIX), wherein Y is carbon, R7 is a boronic acid or boronic ester, A, B and X are as defined above;

Step a) reaction of the resultant intermediate of formula (XXIX) with an intermediate of formula (VI), wherein R5 and R6 are as defined above, to obtain an intermediate of formula (V), wherein Y is carbon, R7 is a boronic acid or boronic ester, A, B, R5, R6 and X are as defined above;

alternatively

Step b) reaction of an intermediate of formula (XIIa), wherein Y is nitrogen, B is a 5- or 6-membered heteroaryl ring, R7 is a boronic acid or boronic ester, A and X are as defined above, with an intermediate of formula (VI), wherein R5 and R6 are as defined above, to obtain an intermediate of formula (V), wherein Y is nitrogen, B is a 5- or 6-membered heterocyclyl ring, R7 is a boronic acid or boronic ester, A, R5, R6 and X are as defined above; or Step b') reaction of an intermediate of formula (XIIa), wherein Y is nitrogen, B is a 5- or 6-membered heteroaryl ring, R7 is a boronic acid or boronic ester, A and X are as defined above, with an intermediate of formula (VII), wherein R6 is as defined above, to obtain an intermediate of formula (V), wherein Y is nitrogen, B is a 5- or 6-membered heteroaryl ring, R5 is hydrogen, R7 is a boronic acid or boronic ester, A, R6 and X are as defined above; alternatively Step g) reduction of an intermediate of formula (XIIa), wherein Y is nitrogen, B is a 5- or 6-membered heteroaryl ring, R7 is a boronic acid or boronic ester, A and X are as defined above, to obtain an intermediate of formula (XXX), wherein Y is nitrogen, B is a 5- or 6-membered heterocyclyl ring, R7 is a boronic acid or boronic ester, A and X are as defined above;

or

Step h) reaction of an intermediate of formula (XIIb), wherein Y is nitrogen, B is a 5- or 6-membered heterocyclyl ring, R7 is a boronic acid or boronic ester, R8 is a suitable protecting group COR10 or COOR10, wherein R10 is a straight or branched ($C_1$-$C_4$) alkyl, and A and X are as defined above, to obtain the intermediate of formula (XXX) as defined above;

then

Step b) reaction of the resultant intermediate of formula (XXX) with an intermediate of formula (VI), wherein R5 and R6 are as defined above, to obtain an intermediate of formula (V), wherein Y is nitrogen, B is a 5- or 6-membered heterocyclyl ring, R7 is a boronic acid or boronic ester, A, R5, R6 and X are as defined above; or Step b') reaction of the resultant intermediate of formula (XXX) with an intermediate of formula (VII), wherein R6 is as defined above, to obtain an intermediate of formula (V), wherein Y is nitrogen, B is a 5- or 6-membered heterocyclyl ring, R5 is hydrogen, R7 is a boronic acid or boronic ester, A, R6 and X are as defined above;

alternatively

Step p) reaction of an intermediate of formula (XXXI), wherein R11 is hydrogen, iodine, bromine or chlorine, A, B, R5, R6, Y and X are as defined above, to obtain an intermediate of formula (V), wherein R7 is a boronic acid or boronic ester, A, B, R5, R6, Y and X are as defined above.

According to step d) of Scheme 5, the reaction is carried out as described for step d) of Scheme 2.

According to steps a), b) and b') of Scheme 5, the reactions are carried out as described for steps a), b) and b') of Scheme 1.

According to steps g) and h) of Scheme 5, the reactions are carried out as described for steps g) and h) of Scheme 3.

According to step p) of Scheme 5, the reaction of intermediates of formula (XXXI) to obtain intermediates of formula (V) can be performed using a catalyst such as Pd(O), PdCl$_2$dppf, PdCl$_2$(CH$_3$CN)$_2$, Pd(OAc)$_2$, Pd(dba)$_2$ with a ligand such as diphenylphosphinoferrocene (dppf), bis(2-di-tert-butyl-phosphinophenyl)ether, tricyclohexyl-phosphine (PCy$_3$), 2-(biphenyl)di-cyclopentylphosphine (PCy$_2$(o-biph), 4,5-bis(diphenylphosphino)-9,9-dimethylx-anthene (Xantphos), a suitable base such as potassium acetate (AcOK), triethylamine (TEA) and in the presence of bis(pinacolato)diboron (B$_2$pin$_2$), pinacolborane (HBpin) or diboronic acid [B(OH)$_2$]$_2$, in a suitable organic solvent such as dimethylsulfoxide, N,N-dimethylformamide, 1,4-dioxane, 1,2-dimethoxyethane, ethanol, toluene and the like at temperatures ranging from room temperature to reflux, for a time period ranging from 1 hour to 48 hours.

Alternatively, when R11 is hydrogen the reaction can be also performed using catalyst such as [Ir(COD)(OMe)$_2$], [Ir(COD)Cl$_2$], with a ligand such as 2,2'-bipyridine (bpy), 4,4'-di-tert-butyl-2,2'-bipyridine (dtbpy), in solvent like 1,2-dimethoxyethane, tetrahydrofuran, benzene, hexane, octane and the like at temperatures ranging from room temperature to reflux, for a time period ranging from 1 hour to 48 hours (Angew. Chem. Int. Ed. 2002, 41, 3056-3058; Tetrahedron Lett. 2002, 43, 5649-5651).

Preparation of intermediates of formula (VIII), wherein Y is carbon, R7 is a boronic acid or boronic ester, R10 is straight or branched ($C_1$-$C_4$) alkyl, and A, B and X are as defined above, can be carried out as described in the following Scheme 6. Intermediates (VIII) can be either commercially available or prepared according to methods well known in the literature and to the skilled in the art. (Med. Chem. Lett. 2014, 5, 592-597).

Scheme 6

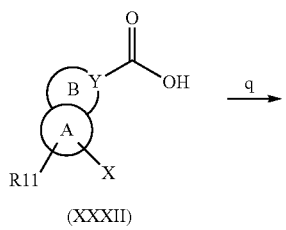

(XXXII)

-continued

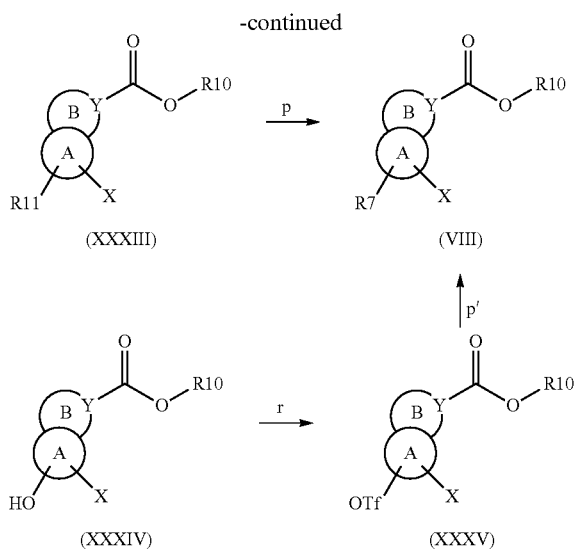

According to Scheme 6, intermediates of formula (VIII) can be prepared by the following reactions:

Step q): reaction of intermediates of formula (XXXII), wherein Y is carbon, R11 is hydrogen, iodine, bromine or chlorine and A, B and X are as defined above, to obtain intermediates of formula (XXXIII), wherein Y is carbon, R11 is hydrogen, iodine, bromine or chlorine, R10 is straight or branched ($C_1$-$C_4$) alkyl, and A, B and X are as defined above;

Step p): reaction of the resultant intermediates of formula (XXXIII) to obtain intermediates of formula (VIII), wherein Y is carbon, R7 is a boronic acid or boronic ester, R10 is straight or branched ($C_1$-$C_4$) alkyl, and A, B and X are as defined above;

alternatively

Step r): reaction of intermediates of formula (XXXIV), wherein Y is carbon, R10 is straight or branched ($C_1$-$C_4$) alkyl, A, B and X are as defined above, to obtain intermediates of formula (XXXV), wherein Y is carbon, R10 is straight or branched ($C_1$-$C_4$) alkyl, OTf is trifluoromethanesylfonate and A, B and X are as defined above;

Step p'): reaction of the resultant intermediates of formula (XXXV) to obtain intermediates of formula (VIII), wherein Y is carbon, R7 is a boronic acid or boronic ester, R10 is straight or branched ($C_1$-$C_4$) alkyl, and A, B and X are as defined above.

According to step q) of Scheme 6, intermediates of formula (XXXII) are submitted to esterification in alcohols such as methanol, ethanol, propanol and the like in the presence of an acid catalyst such as p-toluenesulfonic acid, sulfuric acid, methansulfonic acid at temperatures ranging from room temperature to reflux, for a time period ranging from 1 hour to 48 hours.

Alternatively, intermediates of formula (XXXII) can be converted into the corresponding acyl chloride in the presence of thionylchloride or oxalylchloride, with or without a catalytic amount of dimethylaminopyridine (DMAP), without a solvent or in solvents such as dichloromethane, toluene at temperatures ranging from room temperature to reflux and then treated with alcohols such as methanol, ethanol, propanol and the like.

Alternatively, the reaction can be performed with coupling reagents such as dicyclohexylcarbodiimide (DCC), in the presenze of a catalytic amount of dimethylaminopyridine (DMAP) in solvents like dichloromethane, dimethylformamide and the like at temperatures ranging from zero to room temperature, for a time period ranging from 1 hour to 48 hours.

According to step p) and p') of Scheme 6, the reaction can be performed as described for step p) of Scheme 5.

According to step r) of Scheme 6, the reaction can be performed in the presence of trifluoromethansulfonic anhydride, N-phenyl-bis(trifluoromethanesulphonimide), using a base such as diisopropylethylamine (DIPEA), triethylamine (TEA), with or without a catalytic amount of dimethylaminopyridine (DMAP) in a solvent like dichloromethane, tetrahydrofuran at temperatures ranging from −78° C. to room temperature for a time period ranging from 1 hour to 48 hours.

Preparation of intermediates of formula (XIIa), wherein Y is nitrogen, B is a 5- or 6-membered heteroaryl ring, R7 is a boronic acid or boronic ester, and A, and X are as defined above, or intermediates of formula (XIIb), wherein Y is nitrogen, B is a 5- or 6-membered heterocyclyl ring, R7 is a boronic acid or boronic ester, R8 is a suitable protecting group COR10 or COOR10 wherein R10 is straight or branched ($C_1$-$C_4$) alkyl, A and X are as defined above, can be carried out as described in the following Scheme 7. Intermediates (XIIa) and (XIIb) can be either commercially available or prepared according to methods well known in the literature and to the skilled in the art.

Scheme 7

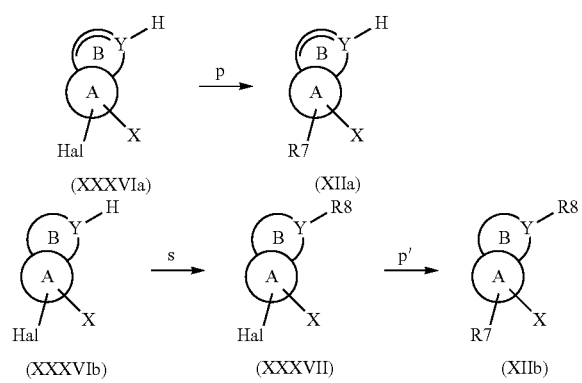

According to Scheme 7, intermediates of formula (XIIa) can be prepared by the following reactions:

Step p): reaction of an intermediate of formula (XXXVIa), wherein Y is nitrogen, B is a 5- or 6-membered heteroaryl ring, Hal is iodine or bromine, A and X are as defined above, to obtain an intermediate of formula (XIIa), wherein Y is nitrogen, B is a 5- or 6-membered heteroaryl ring, R7 is a boronic acid or boronic ester, A and X are as defined above.

According to Scheme 7, intermediates of formula (XIIb) can be prepared by the following reactions:

Step s): protection of an intermediate of formula (XXXVIb), wherein Y is nitrogen, B is a 5- or 6-membered heterocyclyl ring, Hal is iodine or bromine, A and X are as defined above, to obtain an intermediate of formula (XXXVII), wherein Y is nitrogen, B is a 5- or 6-membered heterocyclyl ring, Hal is iodine or bromine, R8 is a suitable protecting group COR10 or COOR10, wherein R10 is straight or branched ($C_1$-$C_4$) alkyl, A and X are as defined above;

Step p'): reaction of the resultant intermediate of formula (XXXVII) to obtain an intermediate of formula (XIIb), wherein Y is nitrogen, B is a 5- or 6-membered heterocyclyl ring, R7 is a boronic acid or boronic ester, R8 is a suitable protecting group COR10 or COOR10, wherein R10 is straight or branched ($C_1$-$C_4$) alkyl, A and X are as defined above.

According to steps p) and p') of Scheme 7, the reaction can be performed as described for step p) of Scheme 5.

According to step s) of Scheme 7, the protection of intermediates of formula (XXXVIb) to intermediates of formula (XXXVII) can be performed with reagents such as acyl chlorides, acetic anhydride, trifluoroacetic anhydride, di-tertbutylcarbamate or ethylchloroformate in the presence of a base such as triethylamine (TEA), diisoprylamine (DIPEA), sodium hydride (NaH), pyridine with or without catalyst such as dimethylaminopyridine (DMAP), in solvents like dichloromethane, tetrahydrofuran, toluene and the like at temperatures ranging from −78° C. to room temperature for a time period ranging from 1 hour to 48 hours.

Preparation of intermediates of formula (XXXI), wherein R11 is hydrogen, iodine, bromine or chlorine, A, B, R5, R6, X and Y are as defined above, can be carried out as described in the following Scheme 8. Intermediates (XXXVIII) and (XXXIX) can be either commercially available or prepared according to methods well known in the literature and to the skilled in the art.

nitrogen, B is a 5- or 6-membered heteroaryl ring, R11 is hydrogen, iodine, bromine or chlorine and A, R5, R6 and X are as defined above;

or

Step b'): reaction of an intermediate of formula (XXXIXa), wherein Y is nitrogen, B is a 5- or 6-membered heteroaryl ring, R11 is hydrogen, iodine, bromine or chlorine and A and X are as defined above, with intermediates of formula (VII), wherein R6 is as defined above, to obtain intermediates of formula (XXXI), wherein Y is nitrogen, B is a 5- or 6-membered heteroaryl ring, R11 is hydrogen, iodine, bromine or chlorine, R5 is hydrogen and R6, A and X are as defined above;

alternatively

Step b): reaction of an intermediate of formula (XXXIXb), wherein Y is nitrogen, B is a 5- or 6-membered heterocyclyl ring, R11 is hydrogen, iodine, bromine or chlorine, and A and X are as defined above, with intermediates of formula (VI), wherein R5 and R6 are as defined above, to obtain intermediates of formula (XXXI), wherein Y is nitrogen, B is a 5- or 6-membered heterocyclyl ring, R11 is hydrogen, iodine, bromine or chlorine and A, R5, R6 and X are as defined above;

or

Step b'): reaction of an intermediate of formula (XXXIXb), wherein Y is nitrogen, B is a 5- or 6-membered heterocyclyl ring, R11 is hydrogen, iodine, bromine or Scheme 8

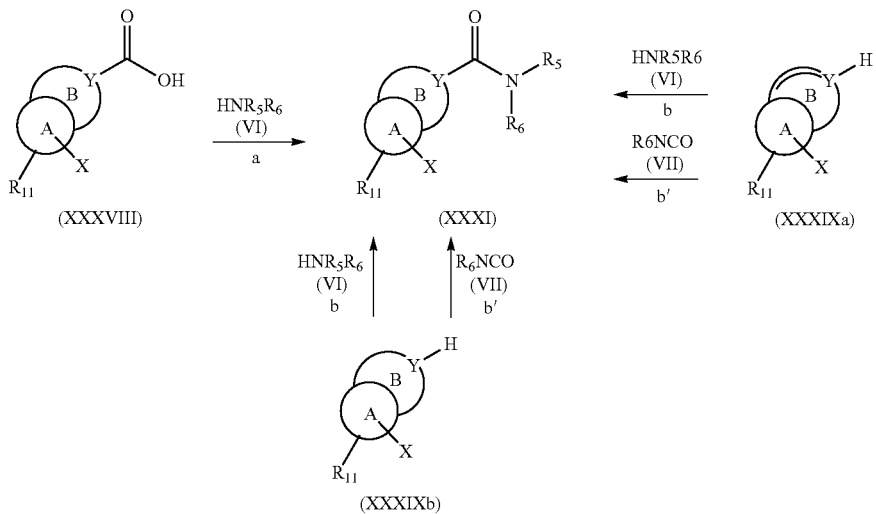

Step a): reaction of intermediates of formula (XXXVIII), wherein Y is carbon, R11 is hydrogen, iodine, bromine, or chlorine, A, B and X are as defined above, with intermediates of formula (VI), wherein R5 and R6 are as defined above, to obtain intermediates of formula (XXXI), wherein Y is carbon, R11 is hydrogen, iodine, bromine or chlorine, A, B, R5, R6 and X are as defined above;

Alternatively

Step b): reaction of an intermediate of formula (XXXIXa), wherein Y is nitrogen, B is a 5- or 6-membered heteroaryl ring, R11 is hydrogen, iodine, bromine or chlorine, and A and X are as defined above, with intermediates of formula (VI), wherein R5 and R6 are as defined above, to obtain intermediates of formula (XXXI), wherein Y is chlorine and A and X are as defined above, with intermediates of formula (VII), wherein R6 is as defined above, to obtain intermediates of formula (XXXI), wherein Y is nitrogen, B is a 5- or 6-membered heterocyclyl ring, R11 is hydrogen, iodine, bromine or chlorine, R5 is hydrogen and R6, A and X are as defined above.

According to steps a), b) and b') of Scheme 8, the reactions are carried out as described for steps a), b) and b') of Scheme 1.

The starting materials of the process object of the present invention, comprehensive of any possible variant, as well as any reactant thereof, are known compounds and if not commercially available per se may be prepared according to well-known methods or as described in the experimental part below.

Pharmacology

In Vitro Cell Proliferation Assay

To evaluate the antiproliferative activity of a compound of formula (I) the following human cell lines were used: A2780 ovarian carcinoma; TT medullary thyroid carcinoma, harboring a mutated RET-C634W receptor; LC-2/ad human lung adenocarcinoma, harboring the CCDC6-RET fusion protein. Exponentially growing cells were seeded and incubated at 37° C. in a humidified 5% $CO_2$ atmosphere using appropriate medium supplemented with 10% Fetal Bovine Serum. 24 hours following cell plating, scalar doses of the compounds dissolved in 0.1% DMSO were added to the medium and cells were exposed to drugs for either 72 hours (A2780) or 144 hours (TT and LC-2/ad), according to their different proliferation rate. At the end of treatment, cell proliferation was determined by an intracellular ATP monitoring system (CellTiterGlo—Promega), following manufacturer's instructions, and using an Envision instrument (PerkinElmer) as reader. Data obtained from compound versus vehicle treated cells were compared using Assay Explorer (Symyx Technologies Inc) software. $IC_{50}$ values were calculated using sigmoidal interpolation curve fitting. In the following Table A the antiproliferative activity of representative compounds of formula (I) on one medullary thyroid carcinoma cell line expressing the aforementioned mutated forms of RET (TT) and on one lung adenocarcinoma cell line harboring the aforementioned fusion form of RET (LC-2/ad) is reported. As control, the antiproliferative activity of the same compounds on an unrelated non RET-dependent cell line (A2780) is reported. All these compounds show remarkable activity on RET-driven cellular models with respect to the unrelated ones.

TABLE A

| Cmpd # | A2780 $IC_{50}$ (µM) | TT $IC_{50}$ (µM) | LC-2/ad $IC_{50}$ (µM) |
| --- | --- | --- | --- |
| cmpd 16 | 2.194 | 0.077 | 0.084 |
| cmpd 1 | 0.867 | 0.001 | 0.003 |
| cmpd 4 | 2.418 | 0.017 | 0.021 |
| cmpd 3 | 0.385 | 0.003 | 0.006 |
| cmpd 7 | 2.810 | 0.048 | 0.046 |
| cmpd 8 | 0.814 | 0.009 | 0.011 |
| cmpd 5 | 2.943 | 0.086 | 0.082 |
| cmpd 6 | 0.348 | 0.024 | 0.049 |
| cmpd 11 | 0.961 | 0.028 | 0.034 |
| cmpd 10 | 0.072 | 0.002 | 0.008 |
| cmpd 13 | 0.463 | 0.007 | 0.006 |
| cmpd 12 | 1.838 | 0.042 | 0.051 |
| cmpd 30 | 2.340 | 0.030 | 0.040 |

From all of the above, the novel compounds of formula (I) of the invention appear to be particularly advantageous in the therapy of diseases caused by dysregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g. to humans, can be administered by the usual routes and the dosage level depends upon the age, weight, and conditions of the patient and administration route.

For example, a suitable dosage adopted for oral administration of a compound of formula (I) may range from about 10 mg to about 1 g per dose, from 1 to 5 times daily. The compounds of the invention can be administered in a variety of dosage forms, e.g. orally, in the form tablets, capsules, sugar or film coated tablets, liquid solutions or suspensions; rectally in the form suppositories; parenterally, e.g. intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g. lactose, dextrose saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine methylcellulose, carboxymethylcellulose or polyvinyl pyrrolidone; disintegrating agents, e.g. starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g. syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g. cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| | |
|---|---|
| g (grams) | mg (milligrams) |
| mL (milliliters) | μL (microliters) |
| mM (millimolar) | mmol (millimoles) |
| μM (micromolar) | $R_t$ (retention time) |
| h (hours) | MHz (Mega-Hertz) |
| mm (millimeters) | Hz (Hertz) |
| M (molar) | min (minutes) |
| mol (moles) | TLC (thin layer chromatography) |
| r.t. (room temperature) | TEA (triethylamine) |
| DMAP (dimethylaminopyridine) | DME (dimethoxyethane) |
| $Na_2SO_4$ (sodium sulphate) | AcOEt (Ethyl acetate) |
| $Na_2CO_3$ (sodium carbonate) | $K_2CO_3$ (potassium carbonate) |
| DMF (N,N-dimethylformamide) | DCM (dichloromethane) |
| DIPEA (N,N-diisopropyl-N-ethylamine) | Hex (hexane) |
| | DMSO (dimethylsulfoxide) |
| THF (tetrahydrofuran) | ESI (electrospray ionization) |
| MeOH (methanol) | OTf (triflate group) |
| $NaHCO_3$ (sodium bicarbonate) | $NH_3$ (33% in water ammonium hydroxide solution) |
| HCl (hydrochloric acid solution) | |
| LiOH (Lithium hydroxide) | KOH (potassium hydroxide) |
| EDCl (1-ethyl-3-(3-dimethylaminopropyl)carbodiimide hydrochloride) | |
| TBTU (N,N,N',N'-tetramethyl-O-(benzotriazol-1-yl)uronium-tetrafluoroborate) | |
| HBTU (N,N,N',N'-tetramethyl-O-(1H-benzotriazol-1-yl)uronium hexafluorophosphate | |
| RP-HPLC (reverse phase high performance liquid chromatography). | |

With the aim at better illustrating the present invention, without posing any limitation to it, the following examples are now given.

As used herein the symbols and conventions used in the processes, schemes and examples are consistent with those used in the contemporary scientific literature, for example, the Journal of the American Chemical Society or the Journal of Biological Chemistry.

Unless otherwise noted, all materials were obtained from commercial suppliers, of the best grade and used without further purification. Anhydrous solvent such as DMF, THF, DCM were obtained from the Aldrich Chemical Company.

All reactions involving air- or moisture-sensitive compounds were performed under nitrogen or argon atmosphere.

General Purification and Analytical Methods

Flash Chromatography was performed on silica gel (Merck grade 9395, 60A).

HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.2 with acetic acid-acetonitrile 95:5), and Mobile phase B was water-acetonitrile (5:95). Gradient from 10 to 90% B in 8 min, hold 90% B 2 min. UV detection at 220 nm and 254 nm. Flow rate 1 mL/min. Injection volume 10 μL. Full scan, mass range from 100 to 800 amu. Capillary voltage was 2.5 KV; source temperature was 120° C.; cone was 10 V. Mass is given as m/z ratio.

When necessary, compounds were purified by preparative HPLC on a Waters Symmetry $C_{18}$ (19×50 mm, 5 μm) column or on a Waters X Terra RP 18 (30×150 mm, 5 μm) column using a Waters preparative HPLC 600 equipped with a 996 Waters PDA detector and a Micromass mod. ZQ single quadrupole mass spectrometer, electron spray ionization, positive mode. Mobile phase A was water/0.1% TFA, and mobile phase B was acetonitrile. Gradient from 10 to 90% B in 8 min, hold 90% B 2 min. Flow rate 20 mL/min. In alternative, mobile phase A was water/0.05% $NH_3$, and mobile phase B was acetonitrile. Gradient from 10 to 100% B in 8 min, hold 100% B 2 min. Flow rate 20 mL/min.

$^1$H-NMR spectra were recorded at a constant temperature of 28° C. on a Varian INOVA 400 spectrometer operating at 400.50 MHz and equipped with a 5 mm z-axis PFG Indirect Detection Probe ($^1$H{$^{15}$N-$^{31}$P}).

Chemical shifts were referenced with respect to the residual solvent signals (DMSO-d₆: 2.50 ppm for $^1$H, where not otherwise specified). Data are reported as follows: chemical shift (δ), multiplicity (s=singlet, d=doublet, t=triplet, q=quartet, quin=quintet, br. s=broad singlet, dd=doublet of doublets, ddd=doublet of doublets of doublets, dt=double triplet, td=triplet of doublets, qd=quartet of doublets, tt=triplet of triplets, m=multiplet, spt=septet), coupling constants (J, Hz) and number of protons.

As formerly reported (M. Colombo, F. R. Sirtori, V. Rizzo, Rapid Commun Mass Spectrom 2004, 18(4), 511-517), ESI(+) high-resolution mass spectra (HRMS) were obtained on a Q-Tof Ultima (Waters, Manchester, UK) mass spectrometer directly connected with an Agilent 1100 micro-HPLC system (Palo Alto, US).

Preparation 1

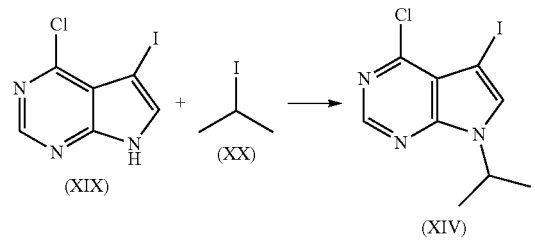

Scheme 4a, Step k

4-Chloro-5-iodo-7-isopropyl-7H-pyrrolo[2,3-d]pyrimidine

Intermediate can be prepared according to the methods described in patents WO2009114874 and WO2011044157.

Y=96%

$^1$H NMR (401 MHz, DMSO-d₆) δ ppm 1.47 (d, J=6.7 Hz, 6H) 4.92-5.15 (m, 1H) 8.16 (s, 1H) 8.63 (s, 1H)

HRMS (ESI) calculated for $C_6H_{10}ClIN_3$ [(M+H)⁺]: 321.9603; found: 321.9605.

According to this same methodology, but employing suitable commercially available reagents, the following intermediates were prepared:

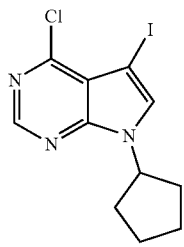

4-Chloro-7-cyclopentyl-5-iodo-7H-pyrrolo[2,3-d]pyrimidine

Y=92%

$^1$H NMR (401 MHz, DMSO-d$_6$) δ ppm 1.61-1.74 (m, 2H) 1.81-2.03 (m, 4H) 2.06-2.22 (m, 2H) 5.04-5.20 (m, 1H) 8.10 (s, 1H) 8.63 (s, 1H)

HRMS (ESI) calculated for C$_{11}$H$_{12}$ClIN$_3$ [(M+H)$^+$]: 347.9759; found: 347.9753.

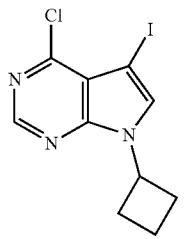 [SMILES: Clc1ncnc2c1c(I)cn2C1CCC1]

4-Chloro-7-cyclobutyl-5-iodo-7H-pyrrolo[2,3-d]pyrimidine

Y=45%

HRMS (ESI) calculated for C$_{10}$H$_{10}$ClIN$_3$ [(M+H)$^+$]: 333.9603; found: 333.9615.

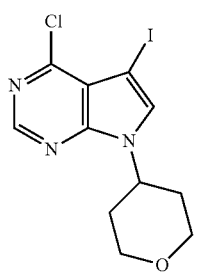 [SMILES: Clc1ncnc2c1c(I)cn2C1CCOCC1]

4-Chloro-5-iodo-7-(tetrahydro-pyran-4-yl)-7H-pyrrolo[2,3-d]pyrimidine

Y=68%

HRMS (ESI) calculated for C$_{11}$H$_{12}$ClIN$_3$O [(M+H)$^+$]: 364.9708; found: 364.9701.

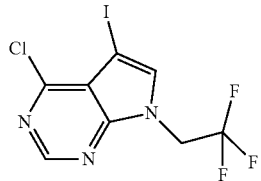 [SMILES: FC(F)(F)Cn1cc(I)c2c(Cl)ncnc21]

4-Chloro-5-iodo-7-(2,2,2-trifluoro-ethyl)-7H-pyrrolo[2,3-d]pyrimidine

Y=98%

$^1$H NMR (401 MHz, DMSO-d$_6$) δ ppm 5.23 (q, J=9.1 Hz, 2H) 8.05 (s, 1H) 8.74 (s, 1H)

HRMS (ESI) calculated for C$_8$H$_5$ClF$_3$IN$_3$ [(M+H)$^+$]: 361.9164; found: 361.9170.

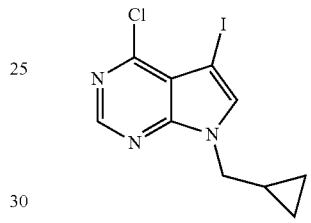

4-Chloro-7-cyclopropylmethyl-5-iodo-7H-pyrrolo[2,3-d]pyrimidine

Y=83%

$^1$H NMR (401 MHz, DMSO-d$_6$) δ ppm 0.39-0.46 (m, 2H) 0.48-0.55 (m, 2H) 1.27 (d, J=7.8 Hz, 1H) 4.12 (d, J=7.3 Hz, 2H) 8.09 (s, 1H) 8.64 (s, 1H)

HRMS (ESI) calculated for C$_{10}$H$_{10}$ClIN$_3$ [(M+H)$^+$]: 333.9603; found: 333.9604.

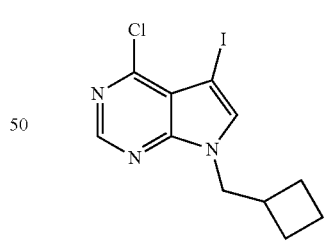

4-Chloro-7-cyclobutylmethyl-5-iodo-7H-pyrrolo[2,3-d]pyrimidine

Y=93%

$^1$H NMR (401 MHz, DMSO-d$_6$) δ ppm 1.68-1.99 (m, 6H) 2.73-2.88 (m, 1H) 4.29 (d, J=7.4 Hz, 2H) 8.02 (s, 1H) 8.63 (s, 1H)

HRMS (ESI) calculated for C$_{11}$H$_{12}$ClIN$_3$ [(M+H)$^+$]: 347.9759; found: 347.9770.

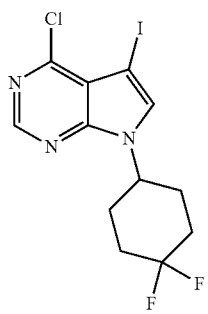 [SMILES: FC1(F)CCC(n2cc(I)c3c(Cl)ncnc32)CC1]

4-Chloro-7-(4,4-difluoro-cyclohexyl)-5-iodo-7H-pyrrolo[2,3-d]pyrimidine

Y=35%

HRMS (ESI) calculated for $C_{12}H_{12}C_1F_2IN_3$ [(M+H)$^+$]: 397.9727; found: 397.9715.

Preparation 2

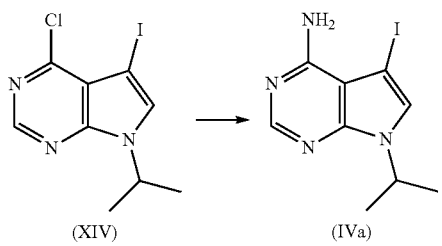

Scheme 4a, Step i

5-Iodo-7-isopropyl-7H-pyrrolo[2,3-d]pyrimidin-4-ylamine

A solution of 4-chloro-5-iodo-7-isopropyl-7H-pyrrolo[2,3-d]pyrimidine (100 mg, 0.31 mmol) in dioxane (0.47 mL) and aqueous NH$_4$OH (0.35 mL) was heated at 100° C. in a microwave apparatus for 4 hours. The solvent was removed under reduced pressure, the residue taken up with AcOEt and washed with distilled water and brine solution. The organic layer was dried over anhydrous Na$_2$SO$_4$ and evaporated to dryness. A pure white solid was obtained.

Y=95%

$^1$H NMR (401 MHz, DMSO-d$_6$) δ ppm 1.40 (d, J=6.7 Hz, 7H) 4.76-4.96 (m, 1H) 6.55 (br. s., 2H) 7.57 (s, 1H) 8.08 (s, 1H)

HRMS (ESI) calculated for $C_9H_{12}IN_4$ [(M+H)$^+$]: 303.0101; found: 303.0104.

According to this same methodology, but employing suitable intermediates, the following intermediates were prepared:

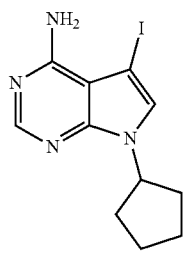 [SMILES: Nc1ncnc2c1c(I)cn2C1CCCC1]

7-Cyclopentyl-5-iodo-7H-pyrrolo[2,3-d]pyrimidin-4-ylamine

Y=73%

$^1$H NMR (401 MHz, DMSO-d$_6$) δ ppm 1.52-1.73 (m, 2H) 1.75-1.91 (m, 4H) 1.98-2.16 (m, 2H) 4.90-5.06 (m, 1H) 6.55 (br. s., 2H) 7.52 (s, 1H) 8.08 (s, 1H)

HRMS (ESI) calculated for $C_{11}H_{14}IN_4$ [(M+H)$^+$]: 329.0258; found: 329.0254.

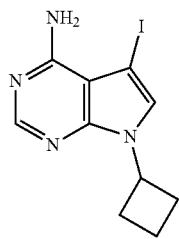 [SMILES: Nc1ncnc2c1c(I)cn2C1CCC1]

7-Cyclobutyl-5-iodo-7H-pyrrolo[2,3-d]pyrimidin-4-ylamine

Y=75%

HRMS (ESI) calculated for $C_{10}H_{12}IN_4$ [(M+H)$^+$]: 315.0101; found: 315.0104.

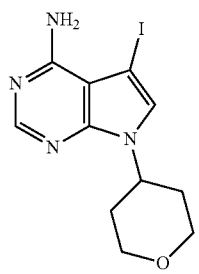 [SMILES: Nc1ncnc2c1c(I)cn2C1CCOCC1]

5-Iodo-7-(tetrahydro-pyran-4-yl)-7H-pyrrolo[2,3-d]pyrimidin-4-ylamine

Y=62%

HRMS (ESI) calculated for $C_{11}H_{14}IN_4O$ [(M+H)$^+$]: 345.0207; found: 345.0203.

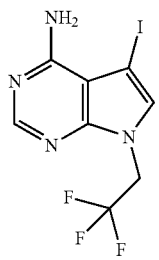

5-Iodo-7-(2,2,2-trifluoro-ethyl)-7H-pyrrolo[2,3-d]pyrimidin-4-ylamine

Y=95%

$^1$H NMR (401 MHz, DMSO-d$_6$) δ ppm 5.03 (q, J=9.3 Hz, 2H) 6.73 (br. s., 2H) 7.49 (d, J=1.1 Hz, 1H) 8.15 (s, 1H)

HRMS (ESI) calculated for C$_8$H$_7$F$_3$IN$_4$ [(M+H)$^+$]: 342.9662; found: 342.9663.

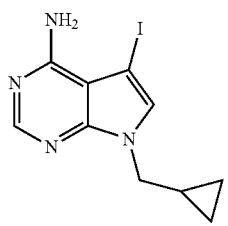 [SMILES: Nc1ncnc2c1c(I)cn2CC1CC1]

7-Cyclopropylmethyl-5-iodo-7H-pyrrolo[2,3-d]pyrimidin-4-ylamine

Y=71%

$^1$H NMR (401 MHz, DMSO-d$_6$) δ ppm 0.35-0.40 (m, 2H) 0.44-0.54 (m, 2H) 1.15-1.29 (m, 1H) 3.95 (d, J=7.1 Hz, 2H) 6.57 (br. s., 2H) 7.52 (s, 1H) 8.09 (s, 1H)

HRMS (ESI) calculated for C$_{10}$H$_{12}$IN$_4$ [(M+H)$^+$]: 315.0101; found: 315.0096.

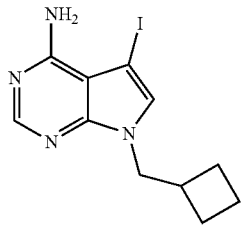 [SMILES: Nc1ncnc2c1c(I)cn2CC1CCC1]

7-Cyclobutylmethyl-5-iodo-7H-pyrrolo[2,3-d]pyrimidin-4-ylamine

Y=94%

$^1$H NMR (401 MHz, DMSO-d$_6$) δ ppm 1.59-2.02 (m, 6H) 2.73 (quin, J=7.6 Hz, 1H) 4.12 (d, J=7.4 Hz, 2H) 6.57 (br. s., 2H) 7.39-7.47 (m, 1H) 8.09 (s, 1H)

HRMS (ESI) calculated for C$_{11}$H$_{14}$IN$_4$ [(M+H)$^+$]: 329.0258; found: 329.0269.

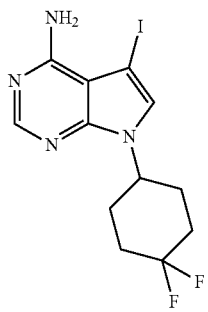 [SMILES: Nc1ncnc2c1c(I)cn2C1CCC(F)(F)CC1]

7-(4,4-Difluoro-cyclohexyl)-5-iodo-7H-pyrrolo[2,3-d]pyrimidin-4-ylamine

Y=42%

HRMS (ESI) calculated for C$_{12}$H$_{14}$F$_2$IN$_4$ [(M+H)$^+$]: 379.0226; found: 379.0229.

Preparation 3

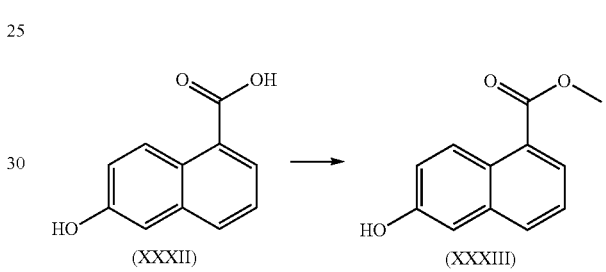

Scheme 6, Step q

6-Hydroxy-naphthalene-1-carboxylic acid methyl ester

Intermediate can be prepared according to the method described in Med. Chem. Lett. 2014, 5, 592-597.

Y=95%

HRMS (ESI) calculated for C$_{12}$H$_{11}$O$_3$ [(M+H)$^+$]: 203.0703; found: 203.0707.

According to this same methodology, but employing suitable starting material, the following intermediate was prepared:

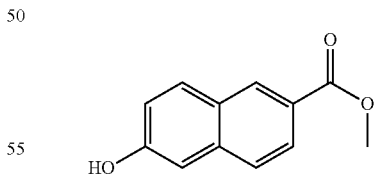

6-Hydroxy-naphthalene-2-carboxylic acid methyl ester

Y=96%

$^1$H NMR (401 MHz, DMSO-d$_6$) δ ppm 3.88 (s, 3H) 7.12-7.22 (m, 2H) 7.74-7.80 (m, 1H) 7.84-7.89 (m, 1H) 7.98 (d, J=8.7 Hz, 1H) 8.49 (s, 1H) 10.17 (s, 1H)

HRMS (ESI) calculated for C$_{12}$H$_{11}$O$_3$ [(M+H)$^+$]: 203.0703; found: 203.0699.

Preparation 4

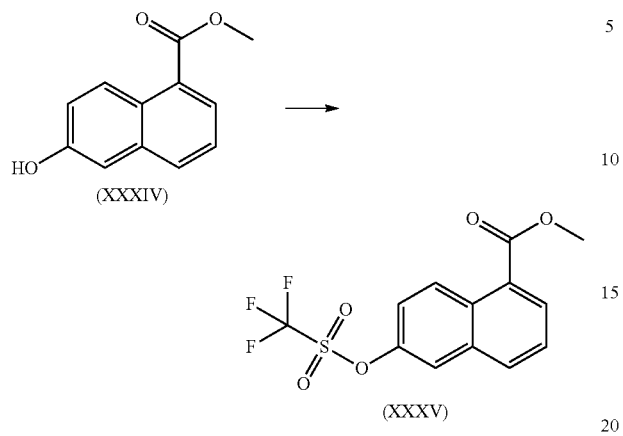

(XXXIV)

(XXXV)

Scheme 6, Step r

6-Trifluoromethanesulfonyloxy-naphthalene-1-carboxylic acid methyl ester

Intermediate can be prepared according to the method described in Med. Chem. Lett. 2014, 5, 592-597 using trifluoromethansulphonic anhydride (Y=97%) or according to the method described in patent WO/2007/104538 using N-phenyltrifluoromethanesulfonimide (Y=93%)

$^1$H NMR (401 MHz, DMSO-d$_6$) δ ppm 3.96 (s, 3H) 7.72-7.82 (m, 2H) 8.27 (dd, J=7.3, 1.3 Hz, 1H) 8.30 (d, J=2.7 Hz, 1H) 8.36 (d, J=8.3 Hz, 1H) 8.94 (d, J=9.5 Hz, 1H)

HRMS (ESI) calculated for C$_{13}$H$_{10}$F$_3$O$_5$S [(M+H)$^+$]: 335.0196; found: 335.0177.

According to these methodologies, but employing suitable starting materials, the following intermediate was prepared:

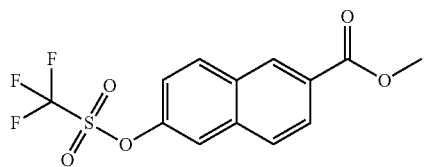 [SMILES: COC(=O)c1ccc2cc(OS(=O)(=O)C(F)(F)F)ccc2c1]

6-Trifluoromethanesulfonyloxy-naphthalene-2-carboxylic acid methyl ester

Y=97%

HRMS (ESI) calculated for C$_{13}$H$_{10}$F$_3$O$_5$S [(M+H)$^+$]: 335.0196; found: 335.0185.

Preparation 5

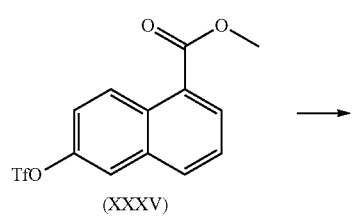

(XXXV)

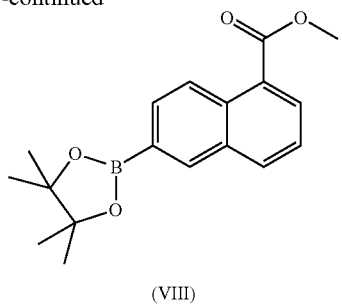

(VIII)

Scheme 6, Step p'

6-(4,4,5,5-Tetramethyl-[1,3,2]dioxaborolan-2-yl)-naphthalene-1-carboxylic acid methyl ester Intermediate can be prepared according to the method described in Med. Chem. Lett. 2014, 5, 592-597.

Y=54%

$^1$H NMR (401 MHz, DMSO-d$_6$) δ ppm 1.33-1.38 (m, 12H) 3.93-3.97 (m, 3H) 7.61-7.67 (m, 1H) 7.83-7.87 (m, 1H) 8.17-8.21 (m, 1H) 8.28-8.33 (m, 1H) 8.39-8.43 (m, 1H) 8.70-8.76 (m, 1H)

HRMS (ESI) calculated for C$_{18}$H$_{22}$BO$_4$ [(M+H)$^+$]: 312.1642; found: 312.1647.

According to this same methodology, but employing suitable starting material, the following intermediate was prepared:

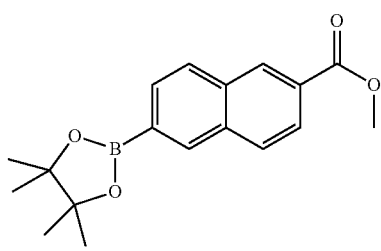

6-(4,4,5,5-Tetramethyl-[1,3,2]dioxaborolan-2-yl)-naphthalene-2-carboxylic acid methyl ester

Y=84%

$^1$H NMR (401 MHz, DMSO-d$_6$) δ ppm 1.35 (s, 12H) 3.93 (s, 3H) 7.80 (dd, J=8.3, 1.1 Hz, 1H) 7.99 (dd, J=8.6, 1.8 Hz, 1H) 8.13 (dd, J=11.0, 8.8 Hz, 2H) 8.39 (s, 1H) 8.63 (s, 1H)

HRMS (ESI) calculated for C$_{18}$H$_{22}$BO$_4$ [(M+H)$^+$]: 312.1606; found: 312.1600.

Preparation 6

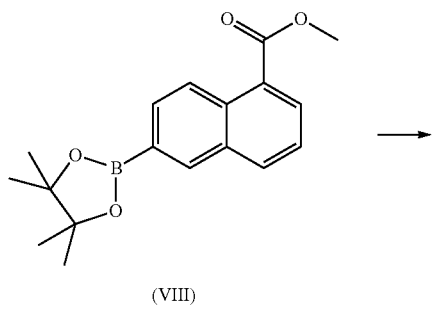

(VIII)

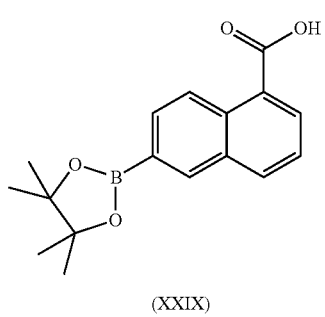

(XXIX)

Scheme 5, Step d 6-(4,4,5,5-Tetramethyl-[1,3,2]dioxaborolan-2-yl)-naphthalene-1-carboxylic acid Intermediate can be prepared according to the method described in Med. Chem. Lett. 2014, 5, 592-597.

Y=48%

HRMS (ESI) calculated for $C_{17}H_{20}BO_4$ [(M+H)$^+$]: 299.1449; found: 299.1452.

According to this same methodology, but employing suitable starting materials, the following intermediates were prepared:

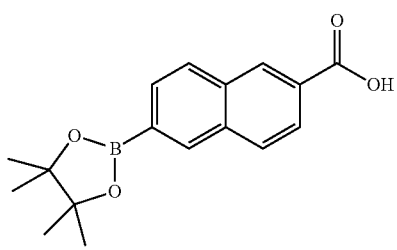 [SMILES: CC1(C)OB(c2ccc3cc(C(=O)O)ccc3c2)OC1(C)C]

6-(4,4,5,5-Tetramethyl-[1,3,2]dioxaborolan-2-yl)-naphthalene-2-carboxylic acid

Y=93%

HRMS (ESI) calculated for $C_{17}H_{20}BO_4$ [(M+H)$^+$]: 299.1449; found: 299.1447.

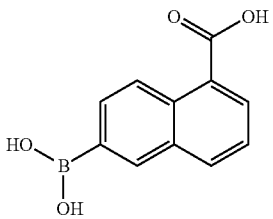 [SMILES: O=C(O)c1cccc2cc(B(O)O)ccc12]

6-(Dihydroxyboranyl)naphthalene-1-carboxylic acid

Y=49%

$^1$H NMR (401 MHz, DMSO-d$_6$) δ ppm 7.54 (t, J=7.7 Hz, 1H) 7.95 (dd, J=8.7, 1.1 Hz, 1H) 8.11 (dd, J=7.6, 3.1 Hz, 2H) 8.23 (s, 2H) 8.41 (s, 1H) 8.75 (d, J=8.8 Hz, 1H) 13.05 (br. s., 1H)

HRMS (ESI) calculated for $C_{11}H_{10}BO_4$ [(M+H)$^+$]: 217.0667; found: 217.0661.

Preparation 7

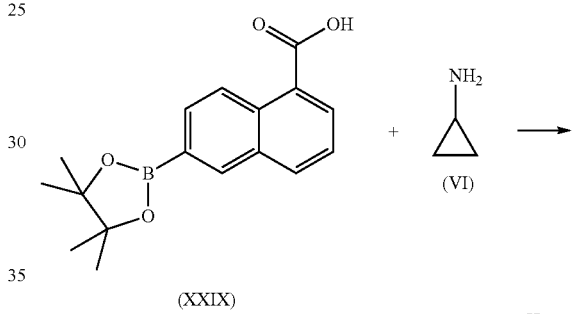

Scheme 5, Step a 6-(4,4,5,5-Tetramethyl-[1,3,2]dioxaborolan-2-yl)-naphthalene-1-carboxylic acid cyclopropylamide To a solution of 6-(4,4,5,5-Tetramethyl-[1,3,2]dioxaborolan-2-yl)-naphthalene-1-carboxylic acid (100 mg, 0.34 mmol) in dry DMF (1 mL), DIPEA (0.114 mL, 0.67 mmol), TBTU (215 mg, 0.67 mmol) and cyclopropylamine (0.046 mL, 0.67 mmol) were added. The reaction mixture was stirred at room temperature overnight. The solvent was removed under reduced pressure, the residue taken up with AcOEt and washed with acid water and brine solution. The organic layer was dried over anhydrous Na$_2$SO$_4$ and evaporated to dryness. The product was isolated as white solid.

Y=53%

HRMS (ESI) calculated for $C_{20}H_{25}BNO_3$ [(M+H)$^+$]: 338.1922; found: 338.1917.

According to this same methodology, but employing suitable starting materials, the following intermediates were prepared:

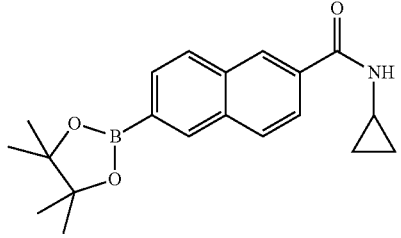 [SMILES: CC1(C)OB(c2ccc3cc(C(=O)NC4CC4)ccc3c2)OC1(C)C]

6-(4,4,5,5-Tetramethyl-[1,3,2]dioxaborolan-2-yl)-naphthalene-2-carboxylic acid cyclopropylamide

Y=63%

HRMS (ESI) calculated for $C_{20}H_{25}BNO_3$ [(M+H)$^+$]: 338.1922; found: 338.1921.

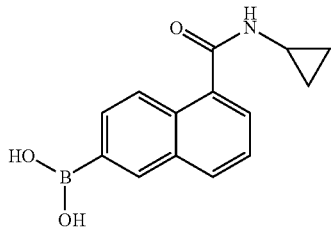 [SMILES: O=C(NC1CC1)c1cccc2cc(B(O)O)ccc12]

[5-(Cyclopropylcarbamoyl)naphtalen-2-yl]boronic acid

Y=98%

$^1$H NMR (401 MHz, DMSO-d$_6$) δ ppm 0.55-0.62 (m, 2H) 0.69-0.77 (m, 2H) 2.90-2.99 (m, 1H) 7.41 (ddd, J=8.3, 7.0, 0.9 Hz, 1H) 7.52 (t, J=8.1 Hz, 1H) 7.55 (dd, J=7.0, 1.5 Hz, 1H) 7.71 (dt, J=8.3, 1.0 Hz, 1H) 7.90 (dd, J=8.5, 1.3 Hz, 1H) 7.98 (d, J=7.8 Hz, 1H) 8.10 (d, J=8.5 Hz, 1H) 8.20 (s, 2H) 8.39 (br. s, 1H) 8.52 (d, J=4.3 Hz, 1H)

HRMS (ESI) calculated for $C_{14}H_{15}BNO_3$ [(M+H)$^+$]: 255.1176; found: 255.1175.

Preparation 8

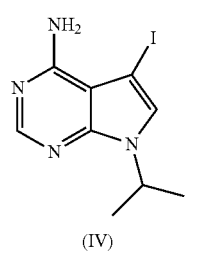

(IV)

+

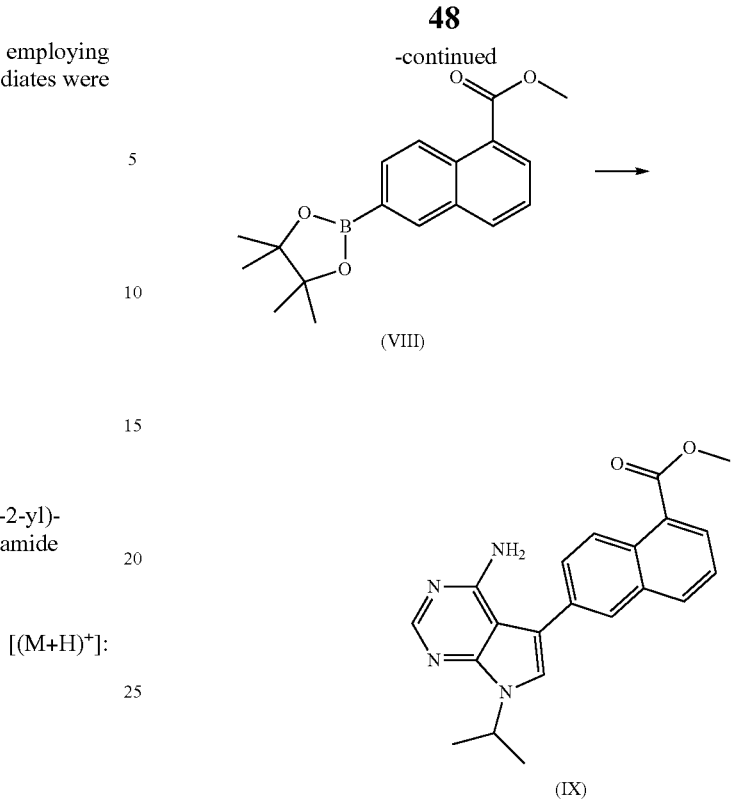

Scheme 2, Step c 6-(4-Amino-7-isopropyl-7H-pyrrolo[2,3-d]pyrimidin-5-yl)-naphthalene-1-carboxylic acid methyl ester 5-Iodo-7-isopropyl-7H-pyrrolo[2,3-d]pyrimidin-4-ylamine (100 mg, 0.33 mmol) was dissolved in a mixture of DME (2.4 mL) and distilled water (1.5 mL). Na$_2$CO$_3$ (140 mg, 1.32 mmol), 6-(4,4,5,5-tetramethyl-[1,3,2]dioxaborolan-2-yl)-naphthalene-1-carboxylic acid methyl ester (113 mg, 0.36 mmol) and tetrakis(triphenylphosphine)palladium(0) (11 mg, 0.01 mmol) were added to the reaction medium under argon atmosphere. The mixture was heated to reflux for 3 hours. The solvent was removed under reduced pressure and the residue taken up with AcOEt and washed with distilled water and brine solution. The organic layer was dried over anhydrous Na$_2$SO$_4$ and evaporated to dryness. The crude was purified by flash-chromatography (AcOEt) affording, after trituration with diethylether, the title compound.

Y=66%

$^1$H NMR (401 MHz, DMSO-d$_6$) δ ppm 1.50 (d, J=6.8 Hz, 6H) 3.97 (s, 3H) 5.01 (quin, J=6.8 Hz, 1H) 6.13 (br. s., 2H) 7.60-7.67 (m, 2H) 7.82 (dd, J=8.9, 2.0 Hz, 1H) 8.10 (d, J=2.0 Hz, 1H) 8.13 (dd, J=7.3, 1.3 Hz, 1H) 8.17 (s, 1H) 8.23 (d, J=8.3 Hz, 1H) 8.82 (d, J=8.9 Hz, 1H)

HRMS (ESI) calculated for $C_{21}H_{21}N_4O_2$ [(M+H)$^+$]: 361.1659; found: 361.1665.

According to this same methodology, but employing suitable starting materials, the following intermediates were prepared:

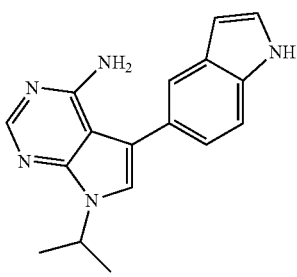 [SMILES: CC(C)n1cc(-c2ccc3[nH]ccc3c2)c2c(N)ncnc21]

5-(1H-Indol-5-yl)-7-isopropyl-7H-pyrrolo[2,3-d]pyrimidin-4-ylamine

Y=85%
$^1$H NMR (401 MHz, DMSO-d$_6$) δ ppm 1.47 (d, J=6.7 Hz, 6H) 4.97 (quin, J=6.7 Hz, 1H) 6.00 (br. s., 2H) 6.47 (ddd, J=3.0, 2.0, 0.9 Hz, 1H) 7.19 (dd, J=8.2, 1.6 Hz, 1H) 7.33-7.36 (m, 1H) 7.39 (t, J=2.7 Hz, 1H) 7.47-7.52 (m, 1H) 7.59-7.62 (m, 1H) 8.12 (s, 1H) 11.17 (br. s., 1H)
HRMS (ESI) calculated for C$_{17}$H$_{18}$N$_5$ [(M+H)$^+$]: 292.1557; found: 292.1550.

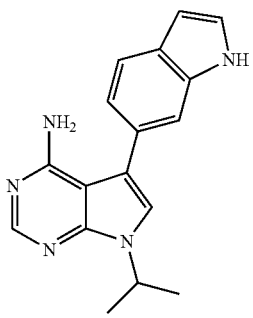 [SMILES: CC(C)n1cc(-c2ccc3cc[nH]c3c2)c2c(N)ncnc21]

5-(1H-Indol-6-yl)-7-isopropyl-7H-pyrrolo[2,3-d]pyrimidin-4-ylamine

Y=83%
$^1$H NMR (401 MHz, DMSO-d$_6$) δ ppm 1.46-1.51 (m, 6H) 4.99 (quin, J=6.8 Hz, 1H) 6.06 (br. s., 2H) 6.47 (dd, J=2.5, 1.5 Hz, 1H) 7.12 (dd, J=8.1, 1.6 Hz, 1H) 7.38 (t, J=2.7 Hz, 1H) 7.40 (s, 1H) 7.46 (s, 1H) 7.63 (d, J=8.1 Hz, 1H) 8.13 (s, 1H) 11.16 (br. s., 1H)
HRMS (ESI) calculated for C$_{17}$H$_{18}$N$_5$ [(M+H)$^+$]: 292.1557; found: 292.1547.

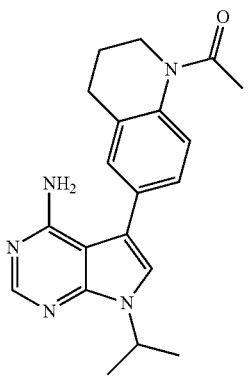 [SMILES: CC(=O)N1CCCc2cc(-c3cn(C(C)C)c4ncnc(N)c34)ccc21]

1-[6-(4-Amino-7-isopropyl-7H-pyrrolo[2,3-d]pyrimidin-5-yl)-3,4-dihydro-2H-quinolin-1-yl]-ethanone Y=78%
$^1$H NMR (401 MHz, DMSO-d$_6$) δ ppm 1.39-1.50 (m, 6H) 1.91 (quin, J=6.4 Hz, 3H) 2.21 (s, 3H) 2.76 (t, J=6.5 Hz, 2H) 3.71 (t, J=6.3 Hz, 2H) 4.97 (quin, J=6.8 Hz, 1H) 6.06 (br. s., 2H) 7.16-7.32 (m, 2H) 7.34-7.78 (m, 3H) 8.13 (s, 1H)
HRMS (ESI) calculated for C$_{20}$H$_{24}$N$_5$O [(M+H)$^+$]: 350.1976; found: 350.1980.

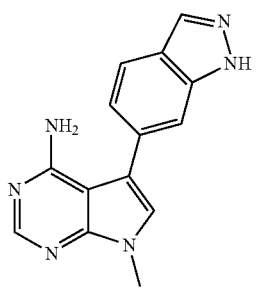 [SMILES: Cn1cc(-c2ccc3cn[nH]c3c2)c2c(N)ncnc21]

5-(1H-Indazol-6-yl)-7-methyl-7H-pyrrolo[2,3-d]pyrimidin-4-ylamine $^1$H NMR (600 MHz, DMSO-d$_6$) δ ppm 3.76 (s, 3H) 6.13 (br. s., 2H) 7.23 (dd, J=8.2, 1.3 Hz, 1H) 7.38 (s, 1H) 7.53 (s, 1H) 7.84 (d, J=8.2 Hz, 1H) 8.09 (s, 1H) 8.17 (s, 1H) 13.08 (s, 1H)
HRMS (ESI) calculated for C$_{14}$H$_{13}$N$_6$ [(M+H)$^+$]: 265.1196; found: 265.1205.

Preparation 9

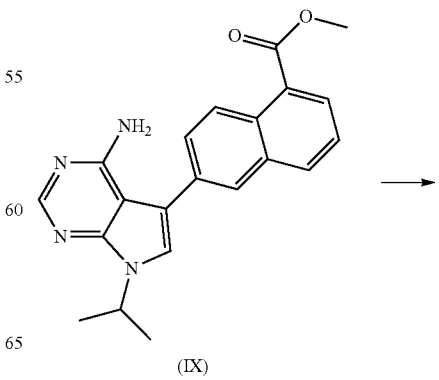

(IX)

-continued

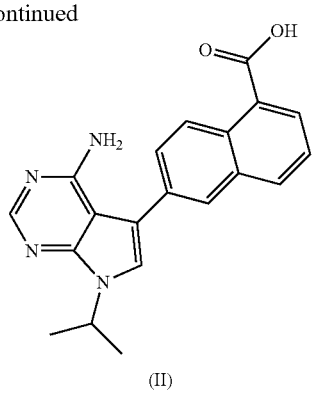

(II)

Scheme 2, Step d 6-(4-Amino-7-isopropyl-7H-pyrrolo[2,3-d]pyrimidin-5-yl)-naphthalene-1-carboxylic acid To a solution of 6-(4-amino-7-isopropyl-7H-pyrrolo[2,3-d]pyrimidin-5-yl)-naphthalene-1-carboxylic acid methyl ester (100 mg, 0.28 mmol) in THF (0.9 mL) and distilled water (0.9 mL), LiOH was added (20 mg, 0.83 mmol). The mixture was stirred overnight at room temperature. Solvent was removed under reduced pressure and the basic aqueous phase was washed twice with AcOEt to remove organic impurities. Then the aqueous layer was acidified with 2 N HCl in order to afford the title compound as a crystalline precipitate.

Y=91%

$^1$H NMR (401 MHz, DMSO-d$_6$) δ ppm 1.53 (d, J=6.8 Hz, 6H) 5.08 (quin, J=6.7 Hz, 1H) 7.64 (dd, J=8.2, 7.3 Hz, 1H) 7.79 (dd, J=8.9, 2.0 Hz, 1H) 7.95 (s, 1H) 8.11 (d, J=1.8 Hz, 1H) 8.18 (dd, J=7.3, 1.3 Hz, 1H) 8.21 (d, J=8.2 Hz, 1H) 8.47 (s, 1H) 8.98 (d, J=8.9 Hz, 1H) 13.20 (br. s., 1H)

HRMS (ESI) calculated for C$_{20}$H$_{19}$N$_4$O$_2$ [(M+H)$^+$]: 347.1503; found: 347.1506.

Preparation 10

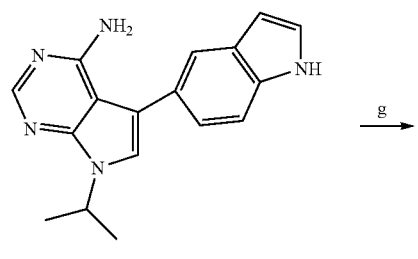

(XIIIa)

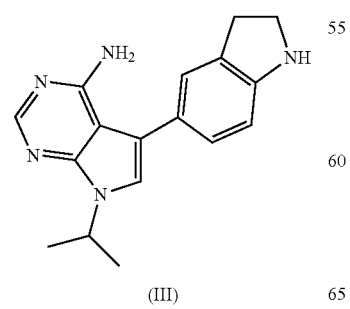

(III)

Scheme 3, Step g 5-(2,3-Dihydro-1H-indol-5-yl)-7-isopropyl-7H-pyrrolo[2,3-d]pyrimidin-4-ylamine Intermediate can be prepared according to the method described in patent WO2014/072220.

Y=72%

$^1$H NMR (401 MHz, DMSO-d$_6$) δ ppm 1.44 (d, J=6.71 Hz, 6H) 2.96 (t, J=8.5 Hz, 2H) 3.46 (td, J=8.5, 1.8 Hz, 2H) 4.94 (quin, J=6.7 Hz, 1H) 5.57 (s, 1H) 5.96 (br. s., 2H) 6.58 (d, J=7.9 Hz, 1H) 6.99 (dd, J=7.9, 1.8 Hz, 1H) 7.12 (s, 1H) 7.17-7.36 (m, 1H) 8.09 (s, 1H)

HRMS (ESI) calculated for C$_{17}$H$_{20}$N$_5$ [(M+H)$^+$]: 294.1713; found: 294.1712.

According to this same methodology, but employing suitable starting materials, the following intermediate was prepared:

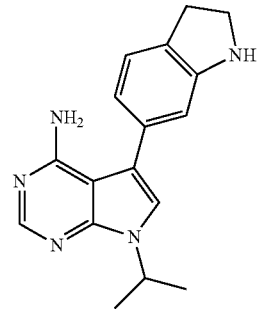 [SMILES: CC(C)n1cc(-c2ccc3c(c2)NCC3)c2c(N)ncnc21]

5-(2,3-Dihydro-1H-indol-6-yl)-7-isopropyl-7H-pyrrolo[2,3-d]pyrimidin-4-ylamine

Y=65%

$^1$H NMR (401 MHz, DMSO-d$_6$) δ ppm 1.45 (d, J=6.7 Hz, 6H) 2.94 (t, J=8.4 Hz, 2H) 3.46 (t, J=8.5 Hz, 2H) 4.94 (quin, J=6.8 Hz, 1H) 5.62 (s, 1H) 6.08 (br. s., 2H) 6.56 (d, J=1.2 Hz, 1H) 6.59 (dd, J=7.3, 1.5 Hz, 1H) 7.09 (d, J=7.2 Hz, 1H) 7.31 (s, 1H) 8.11 (s, 1H)

HRMS (ESI) calculated for C$_{17}$H$_{20}$N$_5$ [(M+H)$^+$]: 294.1713; found: 294.1709.

Preparation 11

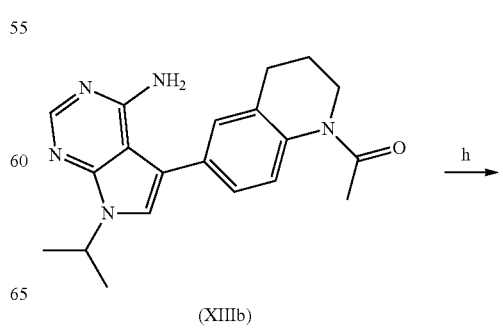

(XIIIb)

53

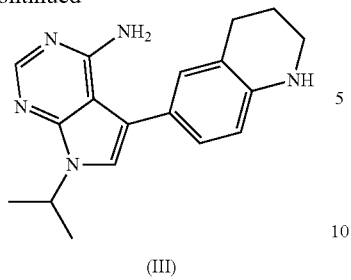

(III)

Scheme 3, Step h

7-Isopropyl-5-(1,2,3,4-tetrahydro-quinolin-6-yl)-7H-pyrrolo[2,3-d]pyrimidin-4-ylamine To a solution of 1-[6-(4-amino-7-isopropyl-7H-pyrrolo[2,3-d]pyrimidin-5-yl)-3,4-dihydro-2H-quinolin-1-yl]-ethanone (100 mg, 0.29 mmol) in MeOH (9.4 mL) and distilled water (4.8 mL), KOH (321 mg, 5.73 mmol) was added. The mixture was heated to reflux for 19 hours. The solvent was removed under reduced pressure and the residue taken up with DCM and washed with distilled water and brine solution. The organic layer was dried over anhydrous Na$_2$SO$_4$ and evaporated to dryness. The crude was purified by flash-chromatography (AcOEt/Hex 8/2-9/1) affording the title compound (63 mg) as yellow oil.

Y=65%

$^1$H NMR (401 MHz, DMSO-d$_6$) δ ppm 1.43 (d, J=6.6 Hz, 6H) 1.82 (quin, J=5.9 Hz, 2H) 2.68-2.73 (m, 2H) 3.17-3.24 (m, 2H) 4.93 (quin, J=6.8 Hz, 1H) 5.74 (s, 1H) 6.06 (br. s., 2H) 6.51 (d, J=9.15 Hz, 1H) 6.87-7.00 (m, 2H) 7.20 (s, 1H) 7.23 (br. s., 1H) 8.08 (s, 1H).

HRMS (ESI) calculated for C$_{18}$H$_{22}$N$_5$ [(M+H)$^+$]: 308.1870; found: 308.1873.

Example 1

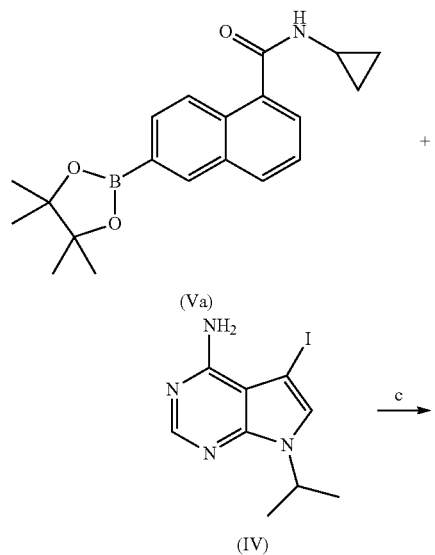

54

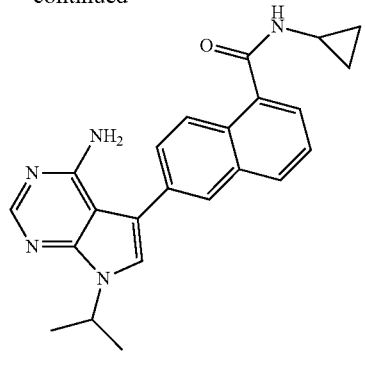

(I)

Scheme 1, Step c 6-(4-Amino-7-isopropyl-7H-pyrrolo[2,3-d]pyrimidin-5-yl)-naphthalene-1-carboxylic acid cyclopropylamide (cmpd 1)

Compound can be prepared according to the method described in Preparation 8

Y=69%

$^1$H NMR (401 MHz, DMSO-d$_6$) δ ppm 0.58-0.63 (m, 2H) 0.71-0.78 (m, 2H) 1.50 (d, J=6.71 Hz, 6H) 2.96 (td, J=7.48, 3.72 Hz, 1H) 5.01 (quin, J=6.80 Hz, 1H) 6.09 (br. s., 2H) 7.51-7.57 (m, 2H) 7.60 (s, 1H) 7.72 (dd, J=8.73, 1.77 Hz, 1H) 7.98-8.07 (m, 2H) 8.17 (s, 1H) 8.29 (d, J=8.67 Hz, 1H) 8.56 (d, J=4.52 Hz, 1H)

HRMS (ESI) calculated for C$_{23}$H$_{24}$N$_5$O [(M+H)$^+$]: 386.1976; found: 386.1972.

According to this same methodology, but employing suitable intermediates, the following compounds were prepared:

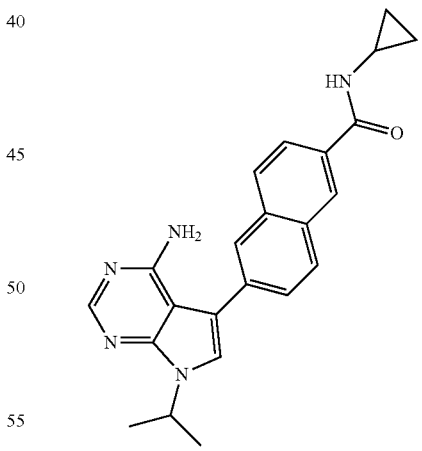

6-(4-Amino-7-isopropyl-7H-pyrrolo[2,3-d]pyrimidin-5-yl)-naphthalene-2-carboxylic acid cyclopropylamide (cmpd 2)

Y=49%

$^1$H NMR (401 MHz, DMSO-d$_6$) δ ppm 0.53-0.64 (m, 2H) 0.67-0.76 (m, 2H) 1.47 (d, J=6.84 Hz, 6H) 2.89 (td, J=7.45, 3.78 Hz, 1H) 4.98 (quin, J=6.71 Hz, 1H) 6.11 (br. s., 2H) 7.61 (s, 1H) 7.70 (dd, J=8.36, 1.65 Hz, 1H) 7.85-7.92 (m, 1H) 7.94-7.98 (m, 1H) 7.99 (s, 1H) 8.06 (d, J=8.54 Hz, 1H) 8.14 (s, 1H) 8.41 (s, 1H) 8.56 (d, J=4.15 Hz, 1H)

HRMS (ESI) calculated for $C_{23}H_{24}N_5O$ [(M+H)$^+$]: 386.1976; found: 386.1971.

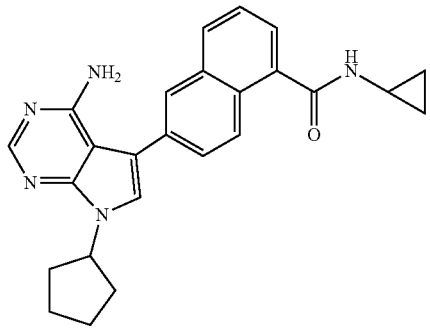 [SMILES: Nc1ncnc2c1c(-c1ccc3c(C(=O)NC4CC4)cccc3c1)cn2C1CCCC1]

6-(4-Amino-7-cyclopentyl-7H-pyrrolo[2,3-d]pyrimidin-5-yl)-naphthalene-1-carboxylic acid cyclopropylamide (cmpd 3)

Y=25%

$^1$H NMR (401 MHz, DMSO-d$_6$) δ ppm 0.53-0.65 (m, 2H) 0.70-0.79 (m, 2H) 1.61-1.77 (m, 2H) 1.80-2.04 (m, 4H) 2.08-2.24 (m, 2H) 2.96 (td, J=11.47, 3.97, 3.36 Hz, 1H) 5.02-5.25 (m, 1H) 6.09 (br. s., 2H) 7.51-7.61 (m, 3H) 7.72 (dd, J=8.67, 1.83 Hz, 1H) 7.95-8.08 (m, 2H) 8.17 (s, 1H) 8.28 (d, J=8.79 Hz, 1H) 8.56 (d, J=4.39 Hz, 1H)

HRMS (ESI) calculated for $C_{25}H_{26}N_5O$ [(M+H)$^+$]: 412.2132; found: 412.2133.

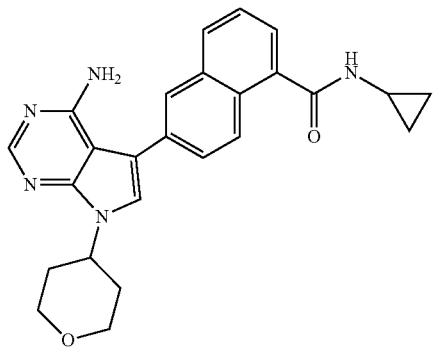 [SMILES: Nc1ncnc2c1c(-c1ccc3c(C(=O)NC4CC4)cccc3c1)cn2C1CCOCC1]

6-[4-Amino-7-(tetrahydro-pyran-4-yl)-7H-pyrrolo[2,3-d]pyrimidin-5-yl]-naphthalene-1-carboxylic acid cyclopropylamide (cmpd 8)

Y=20%

$^1$H NMR (401 MHz, DMSO-d$_6$) δ ppm 0.59-0.64 (m, 2H) 0.71-0.78 (m, 2H) 1.91 (dd, J=12.14, 2.62 Hz, 2H) 2.15 (qd, J=12.25, 4.39 Hz, 2H) 2.92-3.01 (m, 1H) 3.51-3.59 (m, 2H) 4.02 (dd, J=11.11, 4.15 Hz, 2H) 4.87 (tt, J=11.95, 4.04 Hz, 1H) 6.13 (br. s., 2H) 7.52-7.58 (m, 2H) 7.63 (s, 1H) 7.72 (dd, J=8.79, 1.83 Hz, 1H) 7.98-8.06 (m, 2H) 8.18 (s, 1H) 8.29 (d, J=8.79 Hz, 1H) 8.57 (d, J=4.39 Hz, 1H)

HRMS (ESI) calculated for $C_{25}H_{26}N_5O_2$ [(M+H)$^+$]: 428.2081; found: 428.2091.

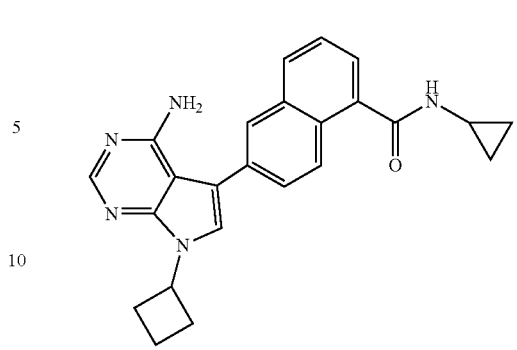

6-(4-Amino-7-cyclobutyl-7H-pyrrolo[2,3-d]pyrimidin-5-yl)-naphthalene-1-carboxylic acid cyclopropylamide (cmpd 12)

Y=15%

HRMS (ESI) calculated for $C_{24}H_{25}N_5O$ [(M+H)$^+$]: 398.1976; found: 398.1979.

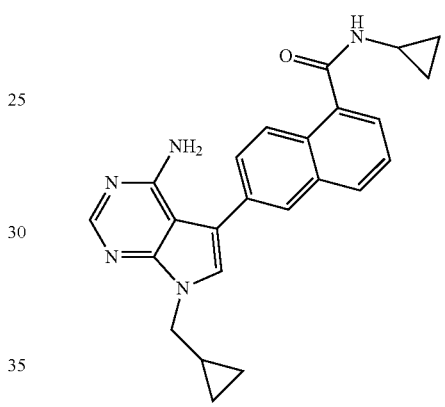

6-(4-Amino-7-cyclopropylmethyl-7H-pyrrolo[2,3-d]pyrimidin-5-yl)-naphthalene-1-carboxylic acid cyclopropylamide (cmpd 13)

Y=47%

$^1$H NMR (401 MHz, DMSO-d$_6$) δ ppm 0.42-0.48 (m, 2H) 0.48-0.56 (m, 2H) 0.58-0.64 (m, 2H) 0.71-0.78 (m, 2H) 1.26-1.38 (m, 1H) 2.92-3.01 (m, 1H) 4.07 (d, J=7.20 Hz, 2H) 6.11 (br. s., 2H) 7.54-7.56 (m, 2H) 7.56 (s, 1H) 7.71 (dd, J=8.73, 1.89 Hz, 1H) 7.99-8.07 (m, 2H) 8.17 (s, 1H) 8.29 (d, J=8.79 Hz, 1H) 8.57 (d, J=4.39 Hz, 1H)

HRMS (ESI) calculated for $C_{24}H_{24}N_5O$ [(M+H)$^+$]: 398.1976; found: 398.1974.

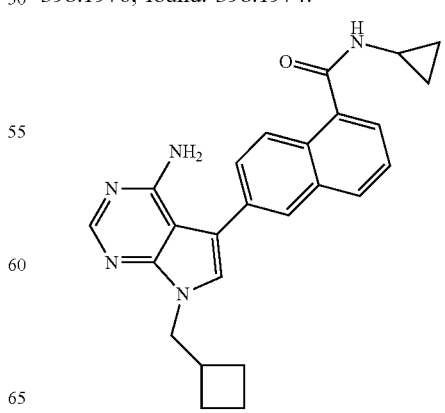

6-(4-Amino-7-cyclobutylmethyl-7H-pyrrolo[2,3-d]pyrimidin-5-yl)-naphthalene-1-carboxylic acid cyclopropylamide (cmpd 14)

Y=46%

¹H NMR (401 MHz, DMSO-d₆) δ ppm 0.58-0.64 (m, 2H) 0.71-0.78 (m, 2H) 1.74-2.06 (m, 6H) 2.84 (quin, J=7.63 Hz, 1H) 2.92-3.01 (m, 1H) 4.23 (d, J=7.45 Hz, 2H) 6.10 (br. s., 2H) 7.47 (s, 1H) 7.52-7.57 (m, 2H) 7.69 (dd, J=8.79, 1.83 Hz, 1H) 8.00 (d, J=1.83 Hz, 1H) 8.01-8.06 (m, 1H) 8.17 (s, 1H) 8.28 (d, J=8.79 Hz, 1H) 8.56 (d, J=4.39 Hz, 1H)

HRMS (ESI) calculated for $C_{25}H_{26}N_5O$ [(M+H)⁺]: 412.2132; found: 412.2134.

6-[4-Amino-7-(4,4-difluoro-cyclohexyl)-7H-pyrrolo[2,3-d]pyrimidin-5-yl]-naphthalene-1-carboxylic acid cyclopropylamide (cmpd 30)

Y=30%

¹H NMR (401 MHz, DMSO-d₆) δ ppm 0.56-0.62 (m, 2H) 0.71-0.77 (m, 2H) 2.02-2.21 (m, 8H) 2.95 (td, J=7.29, 4.09 Hz, 1H) 4.83 (m, 1H) 6.16 (br. s., 2H) 7.54-7.55 (m, 2H) 7.64 (s, 1H) 7.71 (dd, J=8.69, 1.68 Hz, 1H) 8.01-8.03 (m, 2H) 8.18 (s, 1H) 8.28 (d, J=8.85 Hz, 1H) 8.60 (d, J=4.12 Hz, 1H)

HRMS (ESI) calculated for $C_{26}H_{26}F_2N_5O$ [(M+H)⁺]: 462.21; found: 462.2112.

Example 2

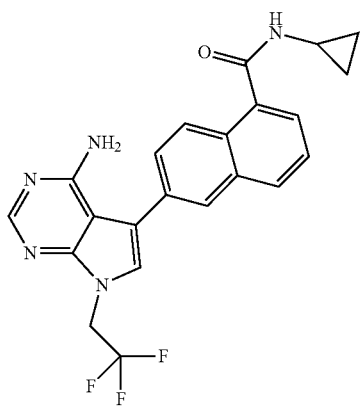 [SMILES: Nc1ncnc2c1c(-c1ccc3c(C(=O)NC4CC4)cccc3c1)cn2CC(F)(F)F]

6-[4-Amino-7-(2,2,2-trifluoro-ethyl)-7H-pyrrolo[2,3-d]pyrimidin-5-yl]-naphthalene-1-carboxylic acid cyclopropylamide (cmpd 15)

Y=56%

¹H NMR (401 MHz, DMSO-d₆) δ ppm 0.58-0.65 (m, 2H) 0.71-0.77 (m, 2H) 2.97 (td, J=7.29, 4.09 Hz, 1H) 5.14 (q, J=9.28 Hz, 2H) 6.28 (br. s., 2H) 7.49-7.52 (m, 1H) 7.55-7.59 (m, 2H) 7.70 (dd, J=8.73, 1.89 Hz, 1H) 8.02-8.10 (m, 2H) 8.24 (s, 1H) 8.31 (d, J=8.79 Hz, 1H) 8.58 (d, J=4.39 Hz, 1H)

HRMS (ESI) calculated for $C_{22}H_{19}F_3N_5O$ [(M+H)⁺]: 426.1536; found: 426.1537.

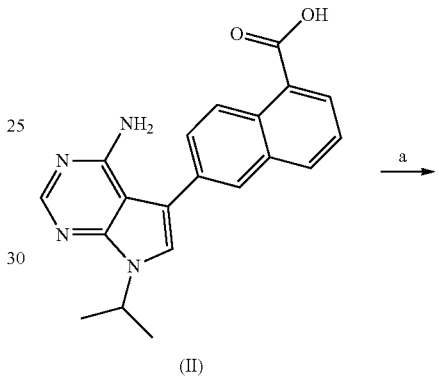

(II)

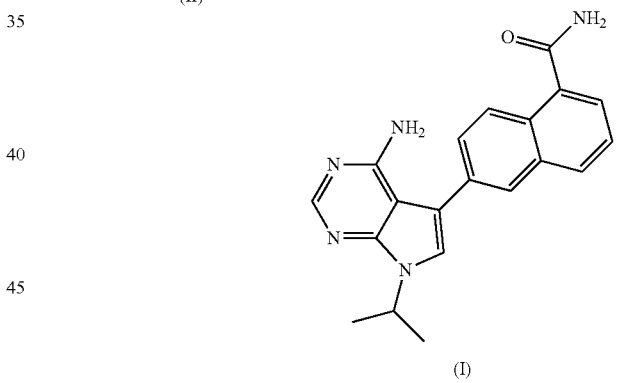

(I)

Scheme 1, Step a

6-(4-Amino-7-isopropyl-7H-pyrrolo[2,3-d]pyrimidin-5-yl)-naphthalene-1-carboxylic acid amide (cmpd 4)

To a solution of 6-(4-amino-7-isopropyl-7H-pyrrolo[2,3-d]pyrimidin-5-yl)-naphthalene-1-carboxylic acid (100 mg, 0.29 mmol) in dry DMF (3.3 mL), DIPEA (0.198 mL, 1.16 mmol), EDCl (90 mg, 0.58 mmol) and 1-hydroxy-1H-benzotriazole ammonium salt (88 mg, 0.58 mmol) were added. The reaction mixture was stirred at room temperature for 4 hours. The solvent was removed under reduced pressure, the residue taken up with AcOEt and washed with a saturated solution of NaHCO₃, HCl 0.5 M and brine. The organic layer was dried over anhydrous Na₂SO₄ and evapo-

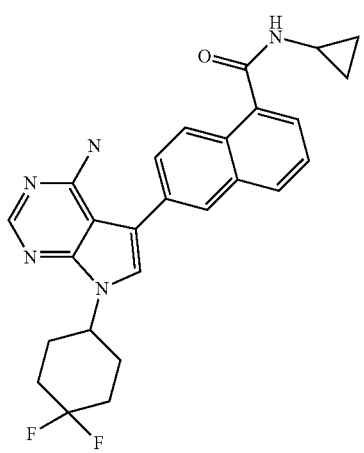 [SMILES: Nc1ncnc2c1c(-c1ccc3c(C(=O)NC4CC4)cccc3c1)cn2C1CCC(F)(F)CC1]

rated to dryness. The crude was purified by flash-chromatography (AcOEt/MeOH 95/5) affording, after trituration with diethylether, the title compound.

Y=57%

¹H NMR (401 MHz, DMSO-d₆) δ ppm 1.50 (d, J=6.71 Hz, 6H) 5.01 (quin, J=6.80 Hz, 1H) 6.10 (br. s., 2H) 7.55 (dd, J=8.18, 7.08 Hz, 1H) 7.58 (br. s., 1H) 7.61 (s, 1H) 7.63-7.66 (m, 1H) 7.72 (dd, J=8.79, 1.83 Hz, 1H) 7.95-8.08 (m, 3H) 8.17 (s, 1H) 8.41 (d, J=8.79 Hz, 1H)

HRMS (ESI) calculated for C₂₀H₂₀N₅O [(M+H)⁺]: 346.1663; found: 346.1669.

Example 3

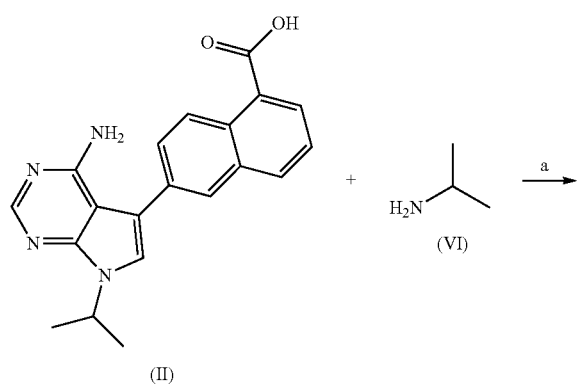

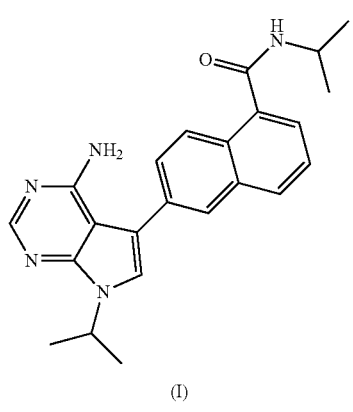

Scheme 1, Step a 6-(4-Amino-7-isopropyl-7H-pyrrolo[2,3-d]pyrimidin-5-yl)-naphthalene-1-carboxylic acid isopropylamide (cmpd 5)

To a solution of 6-(4-amino-7-isopropyl-7H-pyrrolo[2,3-d]pyrimidin-5-yl)-naphthalene-1-carboxylic acid (100 mg, 0.29 mmol) in DMF dry (3.3 mL), DIPEA (0.198 mL, 1.16 mmol), HBTU (220 mg, 0.58 mmol) and isopropylamine (0.05 mL, 0.58 mmol) were added. The reaction mixture was stirred at room temperature for 2 hours. The solvent was removed under reduced pressure, the residue taken up with AcOEt and washed with a saturated solution of NaHCO₃, water and brine. The organic layer was dried over anhydrous Na₂SO₄ and evaporated to dryness. The crude was purified by flash-chromatography (AcOEt/MeOH 99/1) affording, after trituration with diethylether, the title compound.

Y=76%

¹H NMR (401 MHz, DMSO-d₆) δ ppm 1.22 (d, J=6.59 Hz, 6H) 1.50 (d, J=6.84 Hz, 6H) 4.14-4.25 (m, 1H) 4.93-5.09 (quin, J=6.77 Hz, 1H) 6.09 (br. s., 2H) 7.52-7.58 (m, 2H) 7.60 (s, 1H) 7.72 (dd, J=8.79, 1.83 Hz, 1H) 7.97-8.06 (m, 2H) 8.17 (s, 1H) 8.27 (d, J=8.67 Hz, 1H) 8.39 (d, J=7.93 Hz, 1H)

HRMS (ESI) calculated for C₂₃H₂₆N₅O [(M+H)⁺]: 388.2132; found: 388.2130.

According to this same methodology, but employing suitable intermediates, the following compounds were prepared:

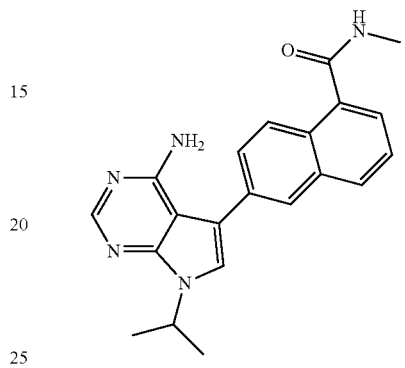

6-(4-Amino-7-isopropyl-7H-pyrrolo[2,3-d]pyrimidin-5-yl)-naphthalene-1-carboxylic acid methylamide (cmpd 6)

Y=65%

¹H NMR (401 MHz, DMSO-d₆) δ ppm 1.50 (d, J=6.84 Hz, 6H) 2.87 (d, J=4.64 Hz, 3H) 5.01 (quin, J=6.71 Hz, 1H) 6.09 (br. s., 2H) 7.53-7.57 (m, 1H) 7.58-7.60 (m, 1H) 7.60 (s, 1H) 7.71 (dd, J=8.79, 1.83 Hz, 1H) 7.97-8.06 (m, 2H) 8.17 (s, 1H) 8.31 (d, J=8.67 Hz, 1H) 8.46 (q, J=4.35 Hz, 1H)

HRMS (ESI) calculated for C₂₁H₂₂N₅O [(M+H)⁺]: 360.1819; found: 360.1831.

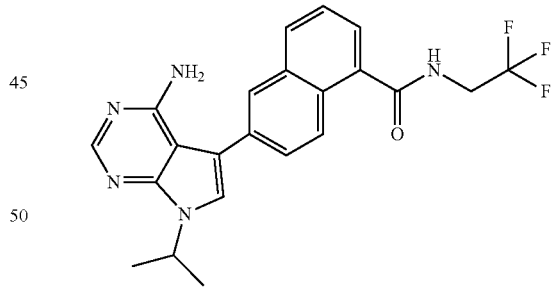

6-(4-Amino-7-isopropyl-7H-pyrrolo[2,3-d]pyrimidin-5-yl)-naphthalene-1-carboxylic acid (2,2,2-trifluoro-ethyl)-amide (cmpd 7)

Y=45%

¹H NMR (401 MHz, DMSO-d₆) δ ppm 1.50 (d, J=6.71 Hz, 6H) 4.18 (qd, J=9.70, 6.41 Hz, 2H) 5.01 (quin, J=6.74 Hz, 1H) 6.11 (br. s., 2H) 7.57-7.64 (m, 3H) 7.75 (dd, J=8.79, 1.95 Hz, 1H) 8.06 (d, J=1.71 Hz, 1H) 8.08-8.12 (m, 1H) 8.17 (s, 1H) 8.24 (d, J=8.79 Hz, 1H) 9.24 (t, J=6.35 Hz, 1H)

HRMS (ESI) calculated for C₂₂H₂₁F₃N₅O [(M+H)⁺]: 428.1693; found: 428.1698.

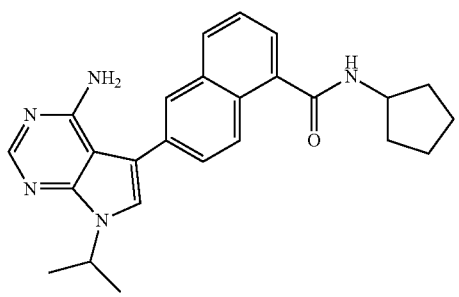 [SMILES: CC(C)n1cc(-c2ccc3c(C(=O)NC4CCCC4)cccc3c2)c2c(N)ncnc21]
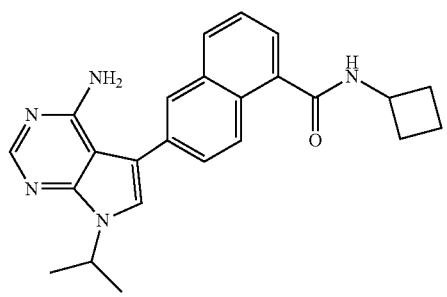 [SMILES: CC(C)n1cc(-c2ccc3c(C(=O)NC4CCC4)cccc3c2)c2c(N)ncnc21]

6-(4-Amino-7-isopropyl-7H-pyrrolo[2,3-d]pyrimidin-5-yl)-naphthalene-1-carboxylic acid cyclopentylamide (cmpd 9)

Y=53%

¹H NMR (401 MHz, DMSO-d$_6$) δ ppm 1.50 (d, J=6.84 Hz, 6H) 1.52-1.76 (m, 6H) 1.87-2.03 (m, 2H) 4.28-4.39 (m, 1H) 4.97-5.06 (m, 1H) 6.09 (br. s., 2H) 7.52-7.59 (m, 2H) 7.61 (s, 1H) 7.71 (dd, J=8.73, 1.89 Hz, 1H) 7.98-8.07 (m, 2H) 8.17 (s, 1H) 8.25 (d, J=8.67 Hz, 1H) 8.48 (d, J=7.32 Hz, 1H)

HRMS (ESI) calculated for C$_{25}$H$_{28}$N$_5$O [(M+H)$^+$]: 414.2289; found: 414.2297.

6-(4-Amino-7-isopropyl-7H-pyrrolo[2,3-d]pyrimidin-5-yl)-naphthalene-1-carboxylic acid cyclobutylamide (cmpd 11)

Y=30%

¹H NMR (401 MHz, DMSO-d$_6$) δ ppm 1.50 (d, J=6.71 Hz, 6H) 1.65-1.77 (m, 2H) 1.98-2.16 (m, 2H) 2.23-2.37 (m, 2H) 4.44-4.62 (m, 1H) 4.94-5.08 (m, 1H) 6.09 (br. s., 2H) 7.52-7.64 (m, 3H) 7.68-7.74 (dd, J=8.79, 2.2 Hz, 1H) 7.99-8.07 (m, 2H) 8.17 (s, 1H) 8.24-8.28 (d, J=8.79 Hz, 1H) 8.72-8.83 (d, J=7.81 Hz, 1H)

HRMS (ESI) calculated for C$_{24}$H$_{26}$N$_5$O [(M+H)$^+$]: 400.2132; found: 400.2128.

Example 4

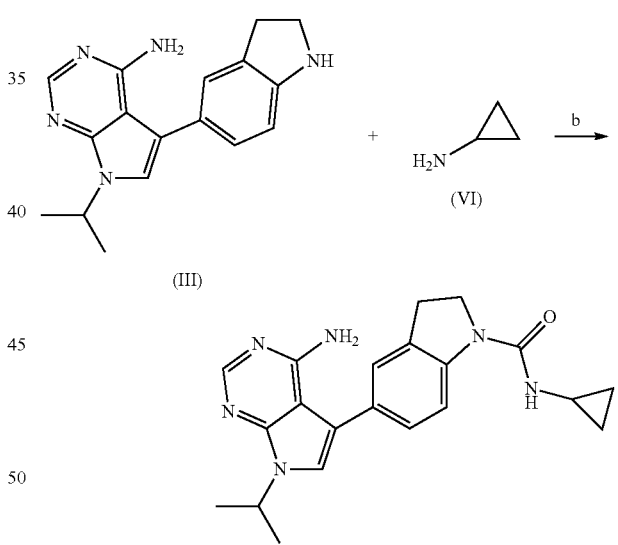

6-(4-Amino-7-isopropyl-7H-pyrrolo[2,3-d]pyrimidin-5-yl)-naphthalene-1-carboxylic acid [4-(4-methyl-piperazin-1-ylmethyl)-3-trifluoromethyl-phenyl]-amide (cmpd 10)

Y=25%

¹H NMR (401 MHz, DMSO-d$_6$) δ ppm 1.47 (d, J=6.71 Hz, 6H) 2.14 (s, 3H) 2.24-2.45 (m, 8H) 3.56 (s, 2H) 4.88-5.14 (m, 1H) 6.08 (br. s., 2H) 7.55-7.66 (m, 2H) 7.68-7.79 (m, 3H) 8.00 (d, J=7.45 Hz, 1H) 8.06 (d, J=1.46 Hz, 1H) 8.11 (d, J=8.18 Hz, 1H) 8.15 (s, 1H) 8.21-8.33 (m, 2H) 10.82 (s, 1H)

HRMS (ESI) calculated for C$_{33}$H$_{35}$F$_3$N$_7$O [(M+H)$^+$]: 602.2850; found: 602.2867.

Scheme 1, Step b

5-(4-Amino-7-isopropyl-7H-pyrrolo[2,3-d]pyrimidin-5-yl)-2,3-dihydro-indole-1-carboxylic acid cyclopropylamide (cmpd 16)

To a suspension of triphosgene (124 mg, 0.42 mmol) and Na$_2$CO$_3$ (106 mg, 2.52 mmol) in DCM (20 mL) kept at 0° C. under argon, cyclopropylamine (0.087 mL, 1.26 mmol) was added. The reaction was monitored by HPLC (following the formation of 1-cyclopropyl-3-(3-methylphenyl)urea by treating a sample of the reaction mixture with 3-methylaniline). After 1 h, 5-(2,3-dihydro-1H-indol-5-yl)-7-isopropyl-7H-pyrrolo[2,3-d]pyrimidin-4-ylamine was added at 0° C. and the reaction was let under stirring 2.5 h at room temperature. The mixture was diluted with DCM, washed with water (3×10 mL) and brine, dried over anhydrous $Na_2SO_4$ and concentrated under vacuum. Purification by flash column chromatography (AcOEt-AcOEt/MeOH 95/5) afforded the product as yellow solid.

Y=66%

$^1$H NMR (401 MHz, DMSO-$d_6$) δ ppm 0.44-0.54 (m, 2H) 0.60-0.66 (m, 2H) 1.45 (d, J=6.71 Hz, 7H) 2.57-2.66 (m, 1H) 3.14 (t, J=8.73 Hz, 3H) 3.87 (t, J=8.79 Hz, 2H) 4.95 (quin, J=6.77 Hz, 1H) 6.02 (br. s., 2H) 6.72 (d, J=2.93 Hz, 1H) 7.17 (dd, J=8.24, 1.89 Hz, 1H) 7.23 (d, J=1.34 Hz, 1H) 7.35 (s, 1H) 7.90 (d, J=8.30 Hz, 1H) 8.11 (s, 1H)

HRMS (ESI) calculated for $C_{21}H_{25}N_6O$ [(M+H)$^+$]: 377.2085; found: 377.2093.

According to this same methodology, but employing suitable intermediates (III and VI), the following compounds were prepared:

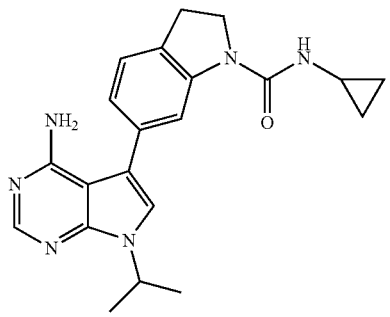 [SMILES: CC(C)n1cc(-c2ccc3c(c2)N(C(=O)NC2CC2)CC3)c2c(N)ncnc21]

6-(4-Amino-7-isopropyl-7H-pyrrolo[2,3-d]pyrimidin-5-yl)-2,3-dihydro-indole-1-carboxylic acid cyclopropylamide (cmpd 17)

Y=49%

$^1$H NMR (401 MHz, DMSO-$d_6$) δ ppm 0.45-0.51 (m, 2H) 0.59-0.64 (m, 2H) 1.46 (d, J=6.71 Hz, 6H) 2.57-2.64 (m, 1H) 3.12 (t, J=8.61 Hz, 2H) 3.88 (t, J=8.73 Hz, 2H) 4.97 (quin, J=6.71 Hz, 1H) 6.08 (br. s., 1H) 6.74 (d, J=2.69 Hz, 1H) 6.92 (dd, J=7.51, 1.65 Hz, 1H) 7.22 (d, J=7.57 Hz, 1H) 7.35 (s, 1H) 7.97 (d, J=1.46 Hz, 1H) 8.12 (s, 1H)

HRMS (ESI) calculated for $C_{21}H_{25}N_6O$ [(M+H)$^+$]: 377.2085; found: 377.2086.

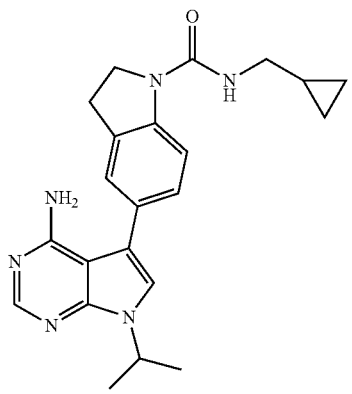 [SMILES: CC(C)n1cc(-c2ccc3c(c2)CCN3C(=O)NCC2CC2)c2c(N)ncnc21]

5-(4-Amino-7-isopropyl-7H-pyrrolo[2,3-d]pyrimidin-5-yl)-2,3-dihydro-indole-1-carboxylic acid cyclopropylmethyl-amide (cmpd 18)

Y=44%

$^1$H NMR (401 MHz, DMSO-$d_6$) δ ppm 0.20-0.24 (m, 2H) 0.36-0.44 (m, 2H) 0.96-1.06 (m, 1H) 1.42-1.48 (d, J=6.71 Hz, 6H) 3.02 (t, J=6.10 Hz, 2H) 3.17 (t, J=8.54 Hz, 2H) 3.93 (t, J=8.73 Hz, 2H) 4.95 (quin, J=6.77 Hz, 1H) 5.99 (br. s., 2H) 6.72 (t, J=5.68 Hz, 1H) 7.16 (dd, J=8.18, 1.83 Hz, 1H) 7.24 (s, 1H) 7.34 (s, 1H) 7.90 (d, J=8.30 Hz, 1H) 8.11 (s, 1H)

HRMS (ESI) calculated for $C_{22}H_{27}N_6O$ [(M+H)$^+$]: 391.2241; found: 391.2249.

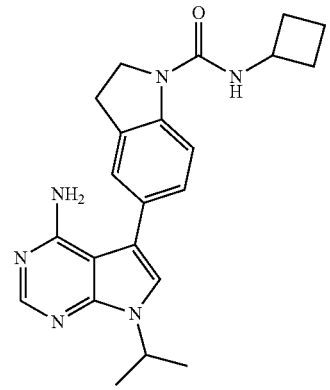 [SMILES: CC(C)n1cc(-c2ccc3c(c2)CCN3C(=O)NC2CCC2)c2c(N)ncnc21]

5-(4-Amino-7-isopropyl-7H-pyrrolo[2,3-d]pyrimidin-5-yl)-2,3-dihydro-indole-1-carboxylic acid cyclobutylamide (cmpd 19)

Y=40%

$^1$H NMR (401 MHz, DMSO-$d_6$) δ ppm 1.45 (d, J=6.84 Hz, 6H) 1.53-1.70 (m, 2H) 1.99-2.11 (m, 2H) 2.13-2.23 (m, 2H) 3.15 (t, J=8.61 Hz, 2H) 3.94 (t, J=8.79 Hz, 2H) 4.14-4.28 (m, 1H) 4.95 (quin, J=6.74 Hz, 1H) 6.00 (br. s., 2H) 6.74 (d, J=7.57 Hz, 1H) 7.15 (dd, J=8.24, 1.89 Hz, 1H) 7.24 (d, J=1.22 Hz, 1H) 7.32-7.37 (m, 1H) 7.88 (d, J=8.18 Hz, 1H) 8.10-8.13 (m, 1H)

HRMS (ESI) calculated for $C_{22}H_{27}N_6O$ [(M+H)$^+$]: 391.2241; found: 391.2252.

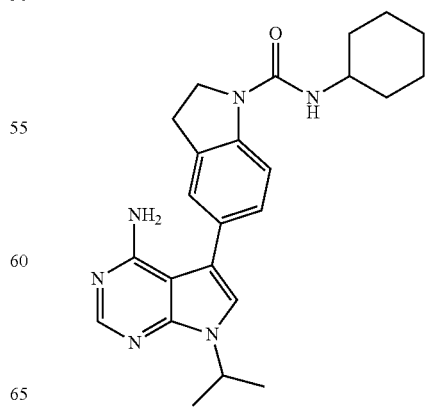

5-(4-Amino-7-isopropyl-7H-pyrrolo[2,3-d]pyrimidin-5-yl)-2,3-dihydro-indole-1-carboxylic acid cyclohexylamide (cmpd 20)

Y=65%

$^1$H NMR (401 MHz, DMSO-d$_6$) δ ppm 1.10 (d, J=12.08 Hz, 1H) 1.21-1.34 (m, 4H) 1.39-1.49 (d, J=6.71 Hz, 6H) 1.60 (d, J=11.84 Hz, 1H) 1.66-1.95 (m, 4H) 3.15 (t, J=8.67 Hz, 2H) 3.47-3.62 (m, 1H) 3.92 (t, J=8.67 Hz, 2H) 4.95 (quin, J=6.68 Hz, 1H) 5.99 (br. s., 2H) 6.25 (d, J=7.81 Hz, 1H) 7.15 (dd, J=8.24, 1.89 Hz, 1H) 7.23 (s, 1H) 7.34 (s, 1H) 7.88 (d, J=8.30 Hz, 1H) 8.11 (s, 1H)

HRMS (ESI) calculated for C$_{24}$H$_{31}$N$_6$O [(M+H)$^+$]: 419.2554; found: 419.2555.

5-(4-Amino-7-isopropyl-7H-pyrrolo[2,3-d]pyrimidin-5-yl)-2,3-dihydro-indole-1-carboxylic acid cyclopentylamide (cmpd 22)

Y=29%

$^1$H NMR (401 MHz, DMSO-d$_6$) δ ppm 1.41-1.47 (m, 7H) 1.51 (td, J=7.35, 4.09 Hz, 4H) 1.59-1.76 (m, 3H) 1.80-1.90 (m, 2H) 3.15 (t, J=8.61 Hz, 2H) 3.93 (t, J=8.73 Hz, 2H) 3.98-4.10 (m, 1H) 4.96 (quin, J=6.74 Hz, 1H) 6.04 (br. s., 2H) 6.33 (d, J=7.20 Hz, 1H) 7.16 (dd, J=8.30, 1.83 Hz, 1H) 7.23 (s, 1H) 7.35 (s, 1H) 7.89 (d, J=8.30 Hz, 1H) 8.12 (s, 1H)

HRMS (ESI) calculated for C$_{23}$H$_{29}$N$_6$O [(M+H)$^+$]: 405.2398; found: 405.2397.

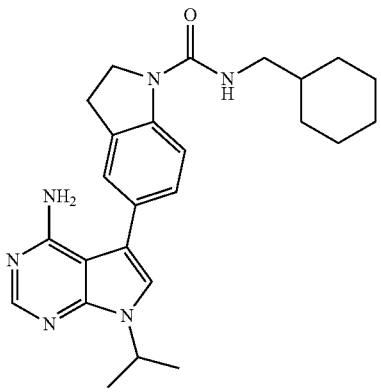 [SMILES: CC(C)n1cc(-c2ccc3c(c2)CCN3C(=O)NCC2CCCCC2)c2c(N)ncnc21]

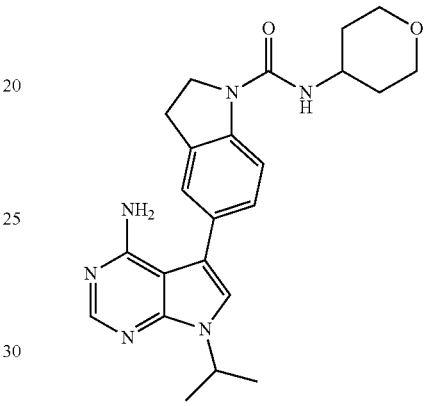

5-(4-Amino-7-isopropyl-7H-pyrrolo[2,3-d]pyrimidin-5-yl)-2,3-dihydro-indole-1-carboxylic acid cyclohexylmethyl-amide (cmpd 21)

Y=18%

$^1$H NMR (401 MHz, DMSO-d$_6$) δ ppm 0.79-0.95 (m, 2H) 1.09-1.26 (m, 3H) 1.45 (d, J=6.96 Hz, 6H) 1.43-1.55 (m, 1H) 1.56-1.77 (m, 4H) 2.98 (t, J=6.29 Hz, 2H) 3.16 (t, J=8.48 Hz, 2H) 3.93 (t, J=8.73 Hz, 2H) 4.96 (quin, J=6.71 Hz, 1H) 6.08 (br. s., 2H) 6.61 (t, J=5.74 Hz, 1H) 7.15 (dd, J=8.36, 1.77 Hz, 1H) 7.23 (s, 1H) 7.36 (s, 1H) 7.89 (d, J=8.30 Hz, 1H) 8.13 (s, 1H)

HRMS (ESI) calculated for C$_{25}$H$_{33}$N$_6$O [(M+H)$^+$]: 433.2711; found: 433.2718.

5-(4-Amino-7-isopropyl-7H-pyrrolo[2,3-d]pyrimidin-5-yl)-2,3-dihydro-indole-1-carboxylic acid (tetrahydro-pyran-4-yl)-amide (cmpd 23)

$^1$H NMR (401 MHz, DMSO-d$_6$) δ ppm 1.45 (d, J=6.71 Hz, 6H) 1.51-1.64 (m, 2H) 1.75 (dd, J=12.51, 2.26 Hz, 2H) 3.16 (t, J=8.61 Hz, 2H) 3.35-3.40 (m, 2H) 3.71-3.82 (m, 1H) 3.87 (dd, J=11.53, 2.75 Hz, 2H) 3.94 (t, J=8.73 Hz, 2H) 4.95 (quin, J=6.77 Hz, 1H) 5.99 (br. s., 2H) 6.40 (d, J=7.69 Hz, 1H) 7.16 (dd, J=8.30, 1.71 Hz, 1H) 7.24 (s, 1H) 7.34 (s, 1H) 7.89 (d, J=8.18 Hz, 1H) 8.11 (s, 1H)

HRMS (ESI) calculated for C$_{23}$H$_{29}$N$_6$O$_2$ [(M+H)$^+$]: 421.2347; found: 421.2357.

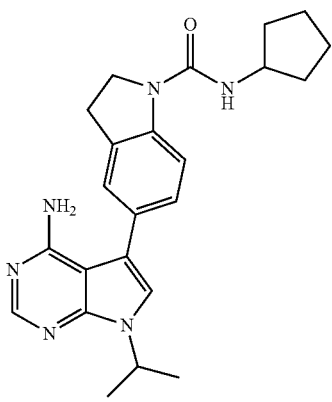 [SMILES: CC(C)n1cc(-c2ccc3c(c2)CCN3C(=O)NC2CCCC2)c2c(N)ncnc21]

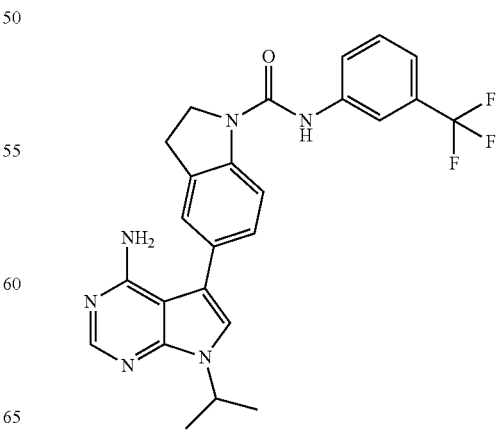

5-(4-Amino-7-isopropyl-7H-pyrrolo[2,3-d]pyrimidin-5-yl)-2,3-dihydro-indole-1-carboxylic acid (3-trifluoromethyl-phenyl)-amide (cmpd 24)

Y=47%

$^1$H NMR (401 MHz, DMSO-$d_6$) δ ppm 1.46 (d, J=6.71 Hz, 6H) 3.22-3.29 (m, 2H) 4.21 (t, J=8.67 Hz, 2H) 4.97 (quin, J=6.74 Hz, 1H) 6.03 (br. s., 2H) 7.24 (dd, J=8.36, 1.77 Hz, 1H) 7.32 (s, 1H) 7.35 (d, J=7.69 Hz, 1H) 7.39 (s, 1H) 7.54 (t, J=7.87 Hz, 1H) 7.89 (d, J=8.79 Hz, 1H) 7.96 (d, J=8.18 Hz, 1H) 8.05 (s, 1H) 8.12 (s, 1H) 8.87 (s, 1H)

HRMS (ESI) calculated for $C_{25}H_{24}F_3N_6O$ [(M+H)$^+$]: 481.1958; found: 481.1965.

5-(4-Amino-7-isopropyl-7H-pyrrolo[2,3-d]pyrimidin-5-yl)-2,3-dihydro-indole-1-carboxylic acid (1-methyl-piperidin-4-yl)-amide (cmpd 26)

Y=25%

$^1$H NMR (401 MHz, DMSO-$d_6$) δ ppm 1.45 (d, J=6.71 Hz, 6H) 1.55 (qd, J=12.00, 3.78 Hz, 2H) 1.74 (d, J=9.76 Hz, 2H) 1.87-1.96 (m, 2H) 2.15 (s, 3H) 2.75 (d, J=11.84 Hz, 2H) 3.15 (t, J=8.61 Hz, 2H) 3.43-3.59 (m, 1H) 3.93 (t, J=8.73 Hz, 2H) 4.95 (quin, J=6.77 Hz, 1H) 5.99 (br. s., 2H) 6.31 (d, J=7.57 Hz, 1H) 7.16 (dd, J=8.24, 1.77 Hz, 1H) 7.23 (s, 1H) 7.34 (s, 1H) 7.88 (d, J=8.18 Hz, 1H) 8.11 (s, 1H)

HRMS (ESI) calculated for $C_{24}H_{32}N_7O$ [(M+H)$^+$]: 434.2663; found: 434.2660.

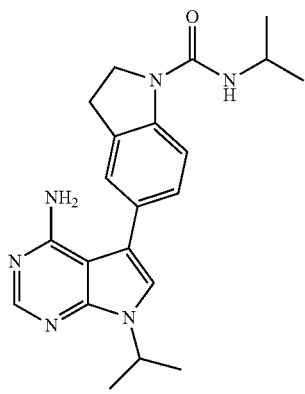 [SMILES: CC(C)NC(=O)N1CCc2cc(-c3cn(C(C)C)c4ncnc(N)c34)ccc21]

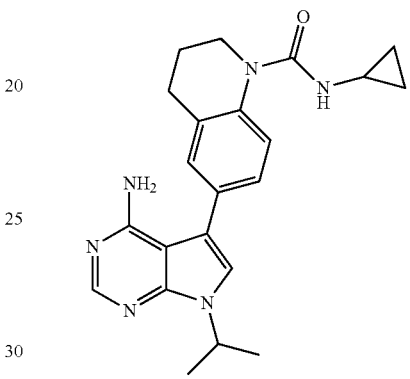

5-(4-Amino-7-isopropyl-7H-pyrrolo[2,3-d]pyrimidin-5-yl)-2,3-dihydro-indole-1-carboxylic acid isopropylamide (cmpd 25)

Y=62%

$^1$H NMR (401 MHz, DMSO-$d_6$) δ ppm 1.12 (d, J=6.59 Hz, 6H) 1.42 (d, J=6.71 Hz, 6H) 3.12 (t, J=8.61 Hz, 2H) 3.80-3.93 (m, 3H) 4.92 (quin, J=6.74 Hz, 1H) 5.96 (br. s., 2H) 6.25 (d, J=7.81 Hz, 1H) 7.13 (dd, J=8.24, 1.77 Hz, 1H) 7.20 (s, 1H) 7.31 (s, 1H) 7.87 (d, J=8.18 Hz, 1H) 8.08 (s, 1H)

HRMS (ESI) calculated for $C_{21}H_{27}N_6O$ [(M+H)$^+$]: 379.2241; found: 379.2257.

6-(4-Amino-7-isopropyl-7H-pyrrolo[2,3-d]pyrimidin-5-yl)-3,4-dihydro-2H-quinoline-1-carboxylic acid cyclopropylamide (cmpd 27)

Y=20%

$^1$H NMR (401 MHz, DMSO-$d_6$) δ ppm 0.44-0.51 (m, 2H) 0.56-0.63 (m, 2H) 1.45 (d, J=6.71 Hz, 6H) 1.84 (quin, J=6.29 Hz, 2H) 2.56-2.64 (m, 1H) 2.73 (t, J=6.41 Hz, 2H) 3.57 (t, J=6.23 Hz, 2H) 4.96 (quin, J=6.80 Hz, 1H) 6.08 (br. s., 2H) 6.84 (d, J=2.93 Hz, 1H) 7.15 (dd, J=8.42, 2.20 Hz, 1H) 7.19 (d, J=2.07 Hz, 1H) 7.37 (s, 1H) 7.47 (d, J=8.42 Hz, 1H) 8.11 (s, 1H)

HRMS (ESI) calculated for $C_{22}H_{27}N_6O$ [(M+H)$^+$]: 391.2241; found: 391.2241.

The invention claimed is:

1. A compound of formula (I):

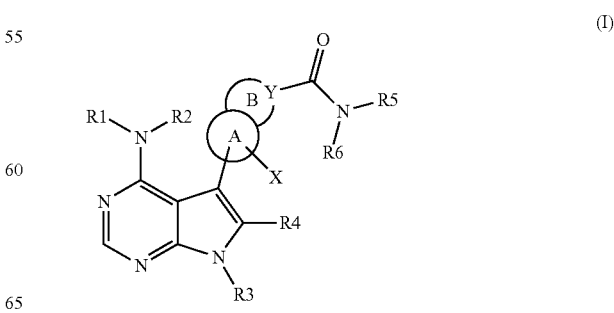

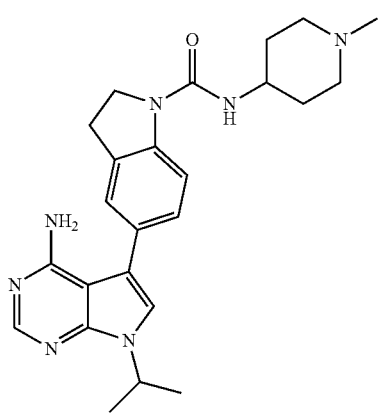

wherein
R1 and R2 are each hydrogen;
R3 is:
hydrogen,
an optionally substituted straight or branched ($C_1$-$C_6$) alkyl group,
an optionally substituted ($C_2$-$C_6$) alkenyl group,
an optionally substituted ($C_2$-$C_6$) alkynyl group,
an optionally substituted ($C_3$-$C_6$) cycloalkyl group,
an optionally substituted aryl group,
an optionally substituted heteroaryl ring, or
an optionally substituted 3- to 7-membered heterocyclyl ring;
R4 is:
hydrogen;
ring A and ring B are fused together to form a bicyclic system comprising Y, which may be carbon or nitrogen, and when Y is carbon, said bicyclic system is selected from the group consisting of naphthalene, indole, isoquinoline, quinoline, benzothiophene, indazole, imidazo[1,2-a]pyridine, benzisothiazole, and benzisoxazole, or
when Y is nitrogen, said bicyclic system is selected from the group consisting of 2,3-dihydroindole, 3,4-dihydroquinoline, and 1,2-dihydroisoquinoline;
X is:
hydrogen,
an optionally substituted straight or branched ($C_1$-$C_6$) alkyl group, or
an optionally substituted ($C_1$-$C_6$) alkoxyl group;
R5 is hydrogen and R6 is:
hydrogen,
an optionally substituted straight or branched ($C_1$-$C_6$) alkyl group,
an optionally substituted ($C_3$-$C_6$) cycloalkyl group,
an optionally substituted heterocyclyl ring,
an optionally substituted aryl group, or
an optionally substituted heteroaryl ring;
or a pharmaceutically acceptable salt thereof.

2. A compound, which is selected from the group consisting of:
6-(4-Amino-7-isopropyl-7H-pyrrolo[2,3-d]pyrimidin-5-yl)-naphthalene-1-carboxylic acid cyclopropylamide,
6-(4-Amino-7-isopropyl-7H-pyrrolo[2,3-d]pyrimidin-5-yl)-naphthalene-2-carboxylic acid cyclopropylamide,
6-(4-Amino-7-cyclopentyl-7H-pyrrolo[2,3-d]pyrimidin-5-yl)-naphthalene-1-carboxylic acid cyclopropylamide,
6-(4-Amino-7-isopropyl-7H-pyrrolo[2,3-d]pyrimidin-5-yl)-naphtalene-1-carboxylic acid amide,
6-(4-Amino-7-isopropyl-7H-pyrrolo[2,3-d]pyrimidin-5-yl)-naphthalene-1-carboxylic acid isopropylamide,
6-(4-Amino-7-isopropyl-7H-pyrrolo[2,3-d]pyrimidin-5-yl)-naphthalene-1-carboxylic acid methylamide,
6-(4-Amino-7-isopropyl-7H-pyrrolo[2,3-d]pyrimidin-5-yl)-naphthalene-1-carboxylic acid (2,2,2-trifluoro-ethyl)-amide,
6-[4-Amino-7-(tetrahydro-pyran-4-yl)-7H-pyrrolo[2,3-d]pyrimidin-5-yl]-naphthalene-1-carboxylic acid cyclopropylamide,
6-(4-Amino-7-isopropyl-7H-pyrrolo[2,3-d]pyrimidin-5-yl)-naphthalene-1-carboxylic acid cyclopentylamide,
6-(4-Amino-7-isopropyl-7H-pyrrolo[2,3-d]pyrimidin-5-yl)-naphthalene-1-carboxylic acid [4-(4-methyl-piperazin-1-ylmethyl)-3-trifluoromethyl-phenyl]-amide,
6-(4-Amino-7-isopropyl-7H-pyrrolo[2,3-d]pyrimidin-5-yl)-naphthalene-1-carboxylic acid cyclobutylamide,
6-(4-Amino-7-cyclobutyl-7H-pyrrolo[2,3-d]pyrimidin-5-yl)-naphthalene-1-carboxylic acid cyclopropylamide,
6-(4-Amino-7-cyclopropylmethyl-7H-pyrrolo[2,3-d]pyrimidin-5-yl)-naphthalene-1-carboxylic acid cyclopropylamide,
6-(4-Amino-7-cyclobutylmethyl-7H-pyrrolo[2,3-d]pyrimidin-5-yl)-naphthalene-1-carboxylic acid cyclopropylamide,
6-[4-Amino-7-(2,2,2-trifluoro-ethyl)-7H-pyrrolo[2,3-d]pyrimidin-5-yl]-naphthalene-1-carboxylic acid cyclopropylamide,
5-(4-Amino-7-isopropyl-7H-pyrrolo[2,3-d]pyrimidin-5-yl)-2,3-dihydro-indole-1-carboxylic acid cyclopropylamide,
6-(4-Amino-7-isopropyl-7H-pyrrolo[2,3-d]pyrimidin-5-yl)-2,3-dihydro-indole-1-carboxylic acid cyclopropylamide,
5-(4-Amino-7-isopropyl-7H-pyrrolo[2,3-d]pyrimidin-5-yl)-2,3-dihydro-indole-1-carboxylic acid cyclopropylmethyl-amide,
5-(4-Amino-7-isopropyl-7H-pyrrolo[2,3-d]pyrimidin-5-yl)-2,3-dihydro-indole-1-carboxylic acid cyclobutylamide,
5-(4-Amino-7-isopropyl-7H-pyrrolo[2,3-d]pyrimidin-5-yl)-2,3-dihydro-indole-1-carboxylic acid cyclohexylamide,
5-(4-Amino-7-isopropyl-7H-pyrrolo[2,3-d]pyrimidin-5-yl)-2,3-dihydro-indole-1-carboxylic acid cyclohexylmethyl-amide,
5-(4-Amino-7-isopropyl-7H-pyrrolo[2,3-d]pyrimidin-5-yl)-2,3-dihydro-indole-1-carboxylic acid cyclopentylamide,
5-(4-Amino-7-isopropyl-7H-pyrrolo[2,3-d]pyrimidin-5-yl)-2,3-dihydro-indole-1-carboxylic acid (tetrahydro-pyran-4-yl)-amide,
5-(4-Amino-7-isopropyl-7H-pyrrolo[2,3-d]pyrimidin-5-yl)-2,3-dihydro-indole-1-carboxylic acid (3-trifluoromethyl-phenyl)-amide,
5-(4-Amino-7-isopropyl-7H-pyrrolo[2,3-d]pyrimidin-5-yl)-2,3-dihydro-indole-1-carboxylic acid isopropylamide,
5-(4-Amino-7-isopropyl-7H-pyrrolo[2,3-d]pyrimidin-5-yl)-2,3-dihydro-indole-1-carboxylic acid (1-methyl-piperidin-4-yl)-amide,
6-(4-Amino-7-isopropyl-7H-pyrrolo[2,3-d]pyrimidin-5-yl)-3,4-dihydro-2H-quinoline-1-carboxylic acid cyclopropylamide,
6-(4-Amino-7-isopropyl-7H-pyrrolo[2,3-d]pyrimidin-5-yl)-isoquinoline-1-carboxylic acid cyclopropylamide,
6-(4-Amino-7-cyclohexyl-7H-pyrrolo[2,3-d]pyrimidin-5-yl)-naphthalene-1-carboxylic acid cyclopropylamide,
6-[4-Amino-7-(4,4-difluoro-cyclohexyl)-7H-pyrrolo[2,3-d]pyrimidin-5-yl]-naphthalene-1-carboxylic acid cyclopropylamide,
6-{4-Amino-7-[1-methyl-piperidin-4-yl]-7H-pyrrolo[2,3-d]pyrimidin-5-yl}-naphthalene-1-carboxylic acid cyclopropylamide,
6-[4-Amino-7-(1-cyclopropyl-piperidin-4-yl)-7H-pyrrolo[2,3-d]pyrimidin-5-yl]-naphthalene-1-carboxylic acid cyclopropylamide,
6-{4-Amino-7-[1-(2-hydroxy-ethyl)-piperidin-4-yl]-7H-pyrrolo[2,3-d]pyrimidin-5-yl}-naphthalene-1-carboxylic acid cyclopropylamide,
6-[7-(1-Acetyl-piperidin-4-yl)-4-amino-7H-pyrrolo[2,3-d]pyrimidin-5-yl]-naphthalene-1-carboxylic acid cyclopropylamide, 6-[4-Amino-7-(2,2,6,6-tetramethyl-piperidin-4-yl)-7H-pyrrolo[2,3-d]pyrimidin-5-yl]-naphthalene-1-carboxylic acid cyclopropylamide, 6-[4-Amino-7-(1,2,2,6,6-pentamethyl-piperidin-4-yl)-7H-pyrrolo[2,3-d]pyrimidin-5-yl]-naphthalene-1-carboxylic acid cyclopropylamide, 6-[4-Amino-7-(1-methyl-piperidin-4-ylmethyl)-7H-pyrrolo[2,3-d]pyrimidin-5-yl]-naphthalene-1-carboxylic acid cyclopropylamide, 6-[4-Amino-7-(1-methyl-azetidin-3-ylmethyl)-7H-pyrrolo[2,3-d]pyrimidin-5-yl]-naphthalene-1-carboxylic acid cyclopropylamide, 6-[4-Amino-7-(1-cyclopropyl-azetidin-3-ylmethyl)-7H-pyrrolo[2,3-d]pyrimidin-5-yl]-naphthalene-1-carboxylic acid cyclopropylamide, 6-[7-(1-Acetyl-azetidin-3-ylmethyl)-4-amino-7H-pyrrolo[2,3-d]pyrimidin-5-yl]-naphthalene-1-carboxylic acid cyclopropylamide, 6-{4-Amino-7-[1-(2-hydroxy-ethyl)-azetidin-3-ylmethyl]-7H-pyrrolo[2,3-d]pyrimidin-5-yl}-naphthalene-1-carboxylic acid cyclopropylamide, 2-(4-Amino-7-isopropyl-7H-pyrrolo[2,3-d]pyrimidin-5-yl)-1H-indole-5-carboxylic acid cyclopropylamide, 2-(4-Amino-7-isopropyl-7H-pyrrolo[2,3-d]pyrimidin-5-yl)-1H-indole-6-carboxylic acid cyclopropylamide, 6-(4-Amino-7-isopropyl-7H-pyrrolo[2,3-d]pyrimidin-5-yl)-imidazo[1,2-a]pyridine-2-carboxylic acid cyclopropylamide, 6-(4-Amino-7-isopropyl-7H-pyrrolo[2,3-d]pyrimidin-5-yl)-1H-indole-3-carboxylic acid cyclopropylamide, 6-(4-Amino-7-isopropyl-7H-pyrrolo[2,3-d]pyrimidin-5-yl)-benzo[b]thiophene-3-carboxylic acid cyclopropylamide, and 6-(4-Amino-7-isopropyl-7H-pyrrolo[2,3-d]pyrimidin-5-yl)-1H-indazole-3-carboxylic acid cyclopropylamide, or a pharmaceutically acceptable salt of said compound.

3. A process for preparing a compound or pharmaceutically acceptable salt according to claim 1, which comprises either:

(A) reacting an intermediate of formula (II):

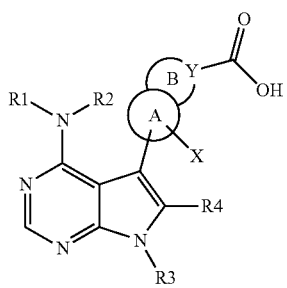

(II)

wherein Y is carbon with an intermediate of formula (VI):

HNR5R6      (VI)

to obtain a compound of formula (I), wherein Y is carbon;

(B) reacting an intermediate of formula (III):

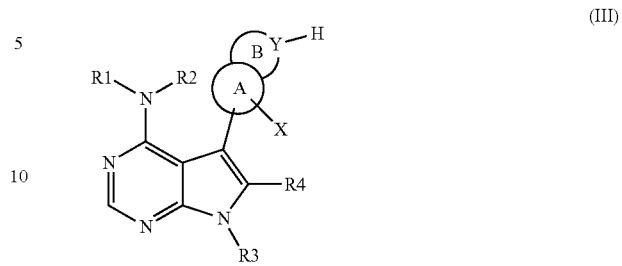

(III)

wherein Y is nitrogen and B is a 5- or 6-membered heterocyclyl ring with an intermediate of formula (VI):

HNR5R6      (VI)

to obtain a compound of formula (I) wherein Y is nitrogen and B is a 5- or 6-membered heterocyclyl ring;

(C) reacting an intermediate of formula (III), wherein Y is nitrogen and B is a 5- or 6-membered heterocyclyl ring with an intermediate of formula (VII):

R6NCO      (VII)

to obtain a compound of formula (I), wherein Y is nitrogen and B is a 5- or 6-membered heterocyclyl ring; or (D) cross-coupling reaction of an intermediate of formula (IV):

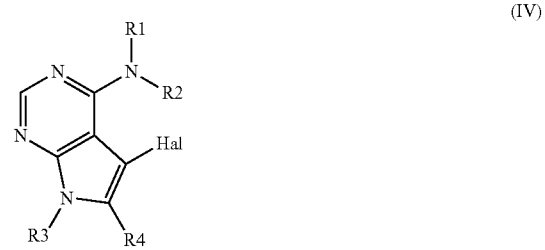

(IV)

wherein Hal is iodine or bromine, with an intermediate of formula (V):

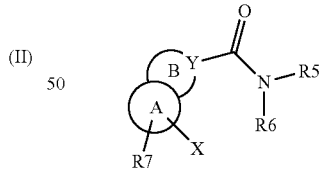

(V)

wherein R7 is a boronic acid or boronic ester, to obtain a compound of formula (I); and optionally converting said compound of formula (I) into another compound of formula (I), converting said compound of formula (I) into a pharmaceutically acceptable salt thereof, or converting said salt into a free compound (I).

4. A method for treating a disease caused by and/or associated with a dysregulated RET kinase activity, which comprises administering to a mammal in need thereof an effective amount of a compound or pharmaceutically acceptable salt according to claim 1, wherein said disease is a tumor.

5. The method according to claim 4, wherein said mammal in need thereof is a human.

6. The method according to claim 4, wherein said tumor is selected from the group consisting of carcinoma; hematopoietic tumors of lymphoid lineage; hematopoietic tumors of myeloid lineage; tumors of mesenchymal origin; tumors of the central and peripheral nervous system; melanoma; seminoma; teratocarcinoma; osteosarcoma; xeroderma pigmentosum; keratoxanthoma; thyroid cancer; and Kaposi's sarcoma.

7. The method according to claim 4, which provides tumor angiogenesis and metastasis inhibition.

8. The method according to claim 4, further comprising subjecting said mammal in need thereof to a radiation therapy or chemotherapy regimen in combination with at least one cytostatic or cytotoxic agent.

9. A pharmaceutical composition, comprising a therapeutically effective amount of a compound or pharmaceutically acceptable salt according to claim 1, and at least one pharmaceutically acceptable excipient, carrier and/or diluent.

10. A pharmaceutical composition according to claim 9, further comprising one or more chemotherapeutic agents.

11. The method according to claim 4, wherein said tumor is associated with a cancer selected from the group consisting of bladder cancer, breast cancer, colon cancer, kidney cancer, liver cancer, lung cancer, esophagus cancer, gallbladder cancer, ovary cancer, pancreas cancer, stomach cancer, cervix cancer, thyroid cancer, prostate cancer, skin cancer, leukaemia, acute lymphocitic leukaemia, acute lymphoblastic leukaemia, B-cell lymphoma, T-cell lymphoma, Hodgkin's lymphoma, non-Hodgkin's lymphoma, hairy cell lymphoma, Burkett's lymphoma, acute myelogenous leukemia, chronic myelogenous leukemia, myelodysplastic syndrome, promyelocytic leukaemia, fibrosarcoma, rhabdomyosarcoma; astrocytoma neuroblastoma, glioma, schwannomas, papillary thyroid carcinoma, and medullary thyroid carcinoma.

* * * * *